(12) United States Patent
Brayman et al.

(10) Patent No.: US 9,874,566 B2
(45) Date of Patent: Jan. 23, 2018

(54) COMPOSITIONS AND METHODS FOR MAKING AND USING OXYGEN SENSING NANOFIBERS AND SCAFFOLDS

(71) Applicant: University of Virginia Patent Foundation, Charlottesville, VA (US)

(72) Inventors: Kenneth Brayman, Charlottesville, VA (US); Daniel Bowers, Chadds Ford, PA (US); Cassandra L. Fraser, Charlottesville, VA (US); Edward A. Botchwey, III, Atlanta, GA (US)

(73) Assignee: University of Virginia Patent Foundation, Charlottesville, VA (US)

( * ) Notice: Subject to any disclaimer, the term of this patent is extended or adjusted under 35 U.S.C. 154(b) by 28 days.

(21) Appl. No.: 14/818,980

(22) Filed: Aug. 5, 2015

(65) Prior Publication Data
US 2016/0041177 A1   Feb. 11, 2016

Related U.S. Application Data

(60) Provisional application No. 62/033,901, filed on Aug. 6, 2014.

(51) Int. Cl.
| *A61K 8/00* | (2006.01) |
| *G01N 33/58* | (2006.01) |
| *A61K 49/00* | (2006.01) |
| *G01N 33/84* | (2006.01) |

(52) U.S. Cl.
CPC ....... *G01N 33/582* (2013.01); *A61K 49/0015* (2013.01); *A61K 49/0021* (2013.01); *A61K 49/0054* (2013.01); *A61K 49/0095* (2013.01); *G01N 33/583* (2013.01); *G01N 33/84* (2013.01); *G01N 2800/7038* (2013.01)

(58) Field of Classification Search
None
See application file for complete search history.

(56) References Cited

U.S. PATENT DOCUMENTS

| 7,955,861 B2 | 6/2011 | Fraser et al. | |
| 8,728,817 B2 | 5/2014 | Ogle et al. | |
| 9,074,129 B2 | 7/2015 | Fraser et al. | |
| 2009/0137057 A1* | 5/2009 | Fraser | C09B 57/10 436/127 |

OTHER PUBLICATIONS

Wang et al. "Biomimetic electrospun nanofibrous structures for tissue engineering", Materials Today, vol. 16, No. 6, Jun. 2013.*
Del Gaudio "Assessment of poly(ε-caprolactone)/poly(3-hydroxybutyrate-co-3-hydroxyvalerate) blends processed by solvent casting and electrospinning", Materials Science and Engineering A 528 (2011) 1764-1772.*
Semenza, G. L. Oxygen Sensing, Homeostasis, and Disease. N. Engl. J. Med. 2011, 365, 537-547.
Ratcliffe, P. J. Oxygen Sensing and Hypoxia Signalling Pathways in Animals: The Implications of Physiology for Cancer. J. Physiol. (Oxford, U. K.) 2013, 591, 2027-2042.
Xu, H.; Aylott, J. W.; Kopelman, R.; Miller, T. J.; Philbert, M. A. A Real-Time Ratiometric Method for the Determination of Molecular Oxygen Inside Living Cells Using Sol-Gel-Based Spherical Optical Nanosensors with Applications to Rat C6 Glioma. Anal. Chem. 2001, 73, 4124-4133.
Koo, Y.-E. L.; Cao, Y.; Kopelman, R.; Koo, S. M.; Brasuel, M.; Philbert, M. A. Real-Time Measurements of Dissolved Oxygen Inside Live Cells by Organically Modified Silicate Fluorescent Nanosensors. Anal. Chem. 2004, 76, 2498-2505.
Pfister, A.; Zhang, G.; Zareno, J.; Horwitz, A. F.; Fraser, C. L. Boron Polylactide Nanoparticles Exhibiting Fluorescence and Phosphorescence in Aqueous Medium. ACS Nano 2008, 2, 1252-1258.
Kersey, F. R.; Zhang, G.; Palmer, G. M.; Dewhirst, M. W.; Fraser, C. L. Stereocomplexed Poly(lactic Acid)-Poly (ethylene Glycol) Nanoparticles with Dual-Emissive Boron Dyes for Tumor Accumulation. ACS Nano 2010, 4, 4989-4996.
Zhang, H.; Lei, B.; Dong, H.; Liu, Y. Oxygen Sensing Properties of Cu(I) Complex/Polystyrene Composite Nanofibers Prepared by Electrospinning. J. Nanosci. Nanotechnol. 2011, 11, 9840-9845.
Hong, H.; Zhu, L.; Wang, A.; Lu, H. Re(I) Complex Doped Nanofibers for Oxygen Optical Sensing. Spectrochim. Acta, Part A 2012, 98, 466-473.
Xue, R.; Behera, P.; Viapiano, M. S.; Lannutti, J. J. Rapid Response Oxygen-Sensing Nanofibers. Mater. Sci. Eng., C 2013, 33, 3450-3457.
Neal, R. A.; Tholpady, S. S.; Foley, P. L.; Swami, N.; Ogle, R. C.; Botchwey, E. A. Alignment and Composition of Laminin-Polycaprolactone Nanofiber Blends Enhance Peripheral Nerve Regeneration. J. Biomed. Mater. Res., Part A 2011, 100A, 406-423.
Kumbar, S. G.; Nukavarapu, S. P.; James, R.; Nair, L. S.; Laurencin, C. T. Electrospun Poly(lactic Acid-Co-Glycolic Acid) Scaffolds for Skin Tissue Engineering. Biomaterials 2008, 29, 4100-4107.

(Continued)

*Primary Examiner* — James W Rogers
(74) *Attorney, Agent, or Firm* — Rodney L. Sparks

(57) ABSTRACT

To address the need for scaffold-based oxygen concentration monitoring, a single-component, self-referenced oxygen sensor was made into nanofibers. Electrospinning process parameters were tuned to produce a biomaterial scaffold with specific morphological features. The ratio of an oxygen sensitive phosphorescence signal to an oxygen insensitive fluorescence signal was calculated at each image pixel to determine an oxygenation value. A single component boron dye-polymer conjugate was chosen for additional investigation due to improved resistance to degradation in aqueous media compared to a dye polymer blend. Standardization curves show that in fully supplemented media, the fibers are responsive to dissolved oxygen concentrations less than 15 parts per million. Spatial and temporal ratiometric gradients were observed in vitro radiating outward from the center of a dense adherent cell grouping. Sensor activation in ischemia and cell transplant models in vivo show oxygenation decreases on the scale of minutes.

15 Claims, 21 Drawing Sheets
(14 of 21 Drawing Sheet(s) Filed in Color)

(56) References Cited

OTHER PUBLICATIONS

Murray, R. A.; Zhang, G.; Harmata, D.; Neal, R. A.; Botchwey, E. A.; Fraser, C. L. Fabrication and Degradation of Nanofibers Based on Luminescent Boron Dye-PLGA Blends. In Biomaterials; American Chemical Society: Washington D.C., 2010; pp. 33-42.

Zhang, G.; Palmer, G. M.; Dewhirst, M. W.; Fraser, C. L. A Dual-Emissive-Materials Design Concept Enables Tumour Hypoxia Imaging. Nat. Mater. 2009, 8, 747-751.

Zhang, G.; Kooi, S. E.; Demas, J. N.; Fraser, C. L. Emission Color Tuning with Polymer Molecular Weight for Difluoroboron Dibenzoylmethane-Polylactide. Adv. Mater. (Weinheim, Ger.) 2008, 20, 2099-2104.

* cited by examiner

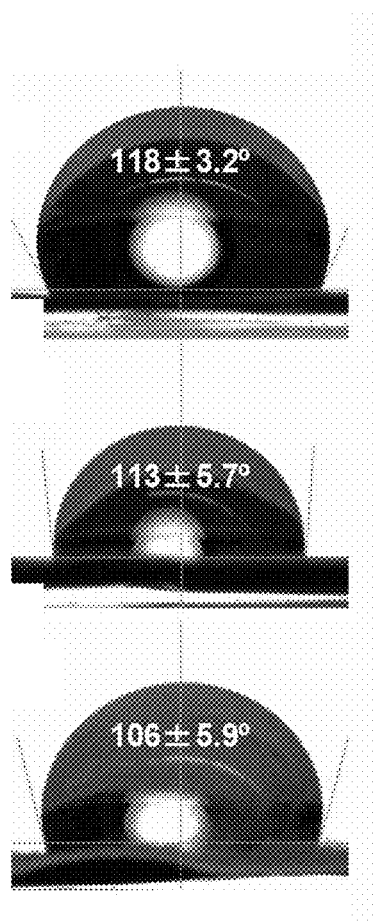
FIG. 2C
FIG. 2D
FIG. 2E
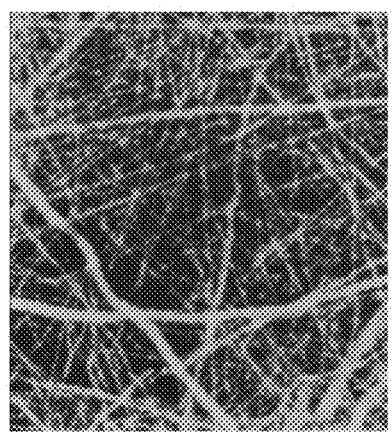
FIG. 2F

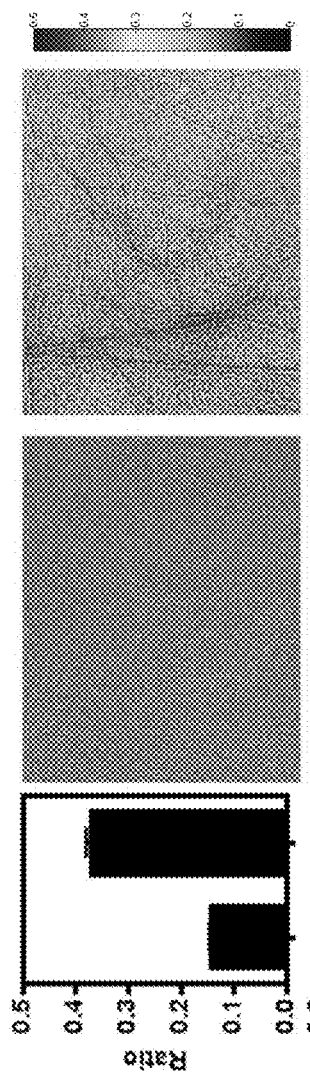
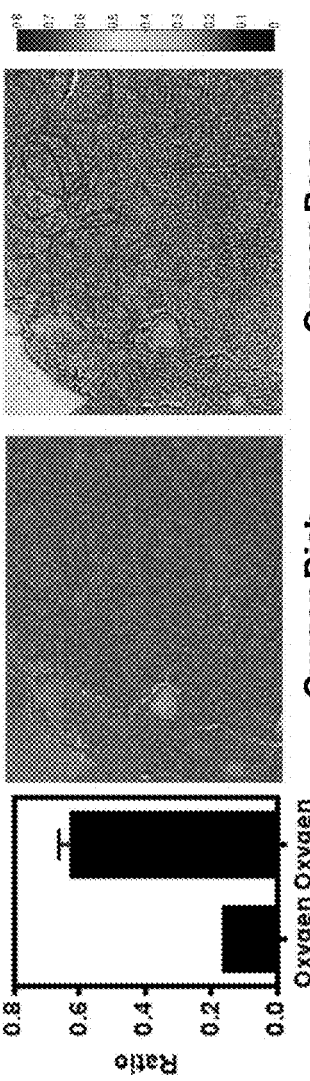
FIG. 3A
FIG. 3B
FIG. 3C

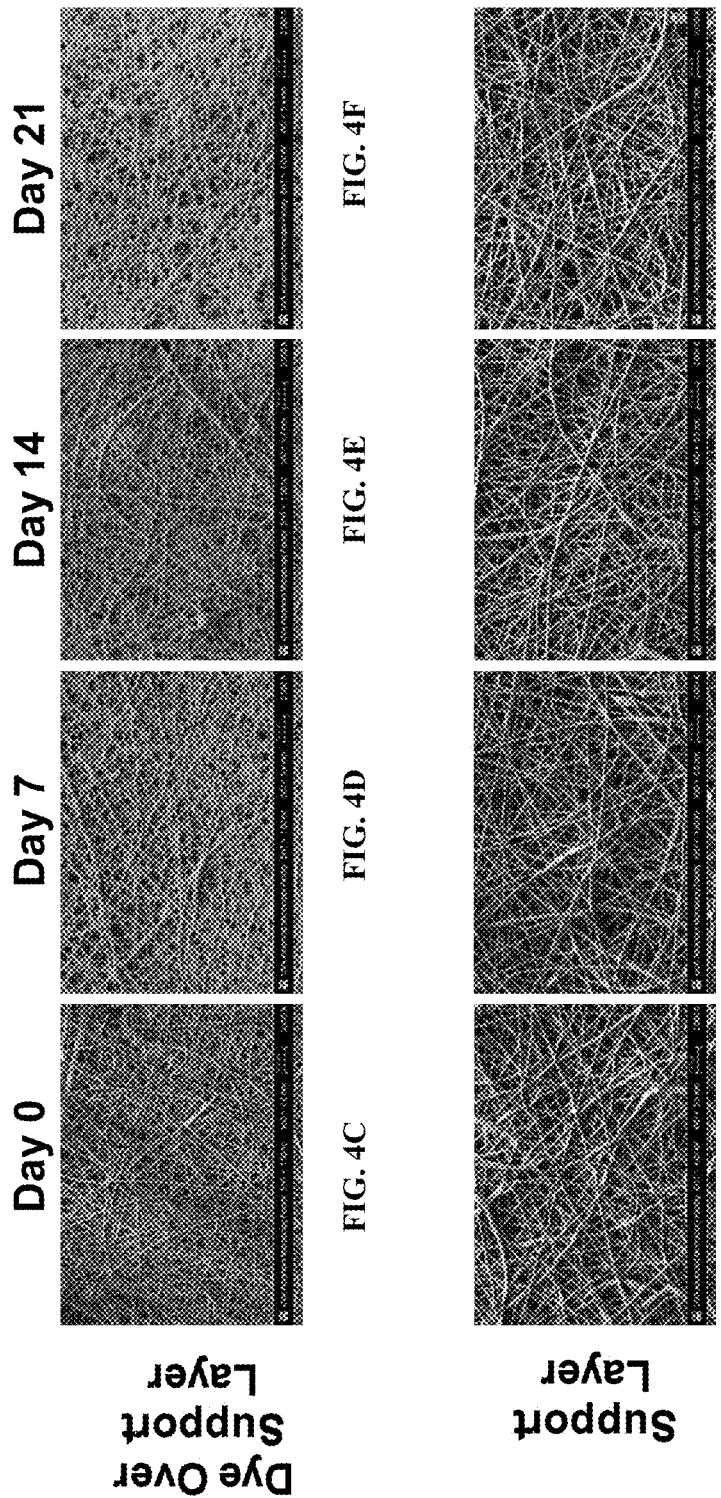

FIG. 6A  FIG. 6B  FIG. 6C
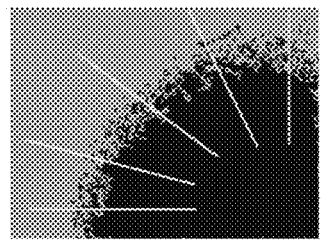 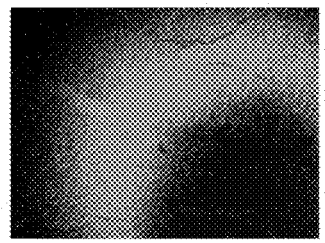
■ cell covered scaffold   ■ 0 min   ▨ 10 min
▨ scaffold only           ▨ 5 min   ■ 15 min
FIG. 6D  FIG. 6E
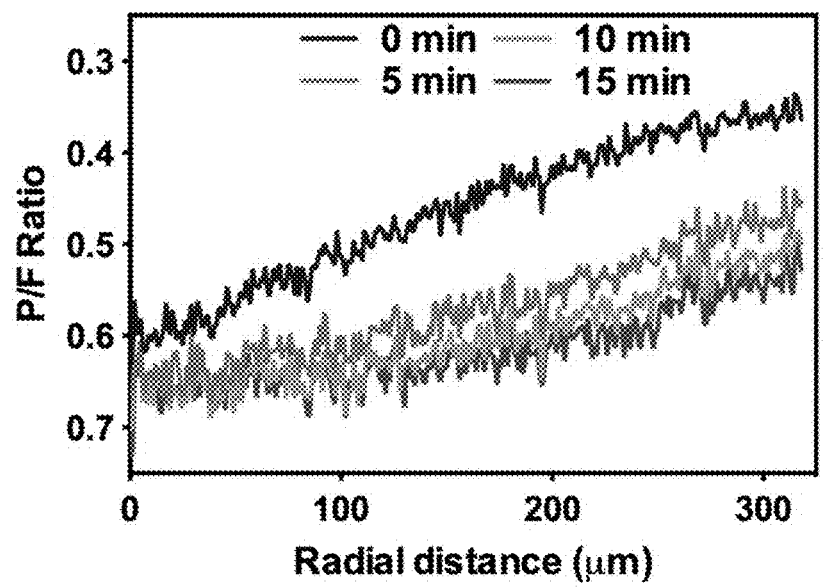
FIG. 6F

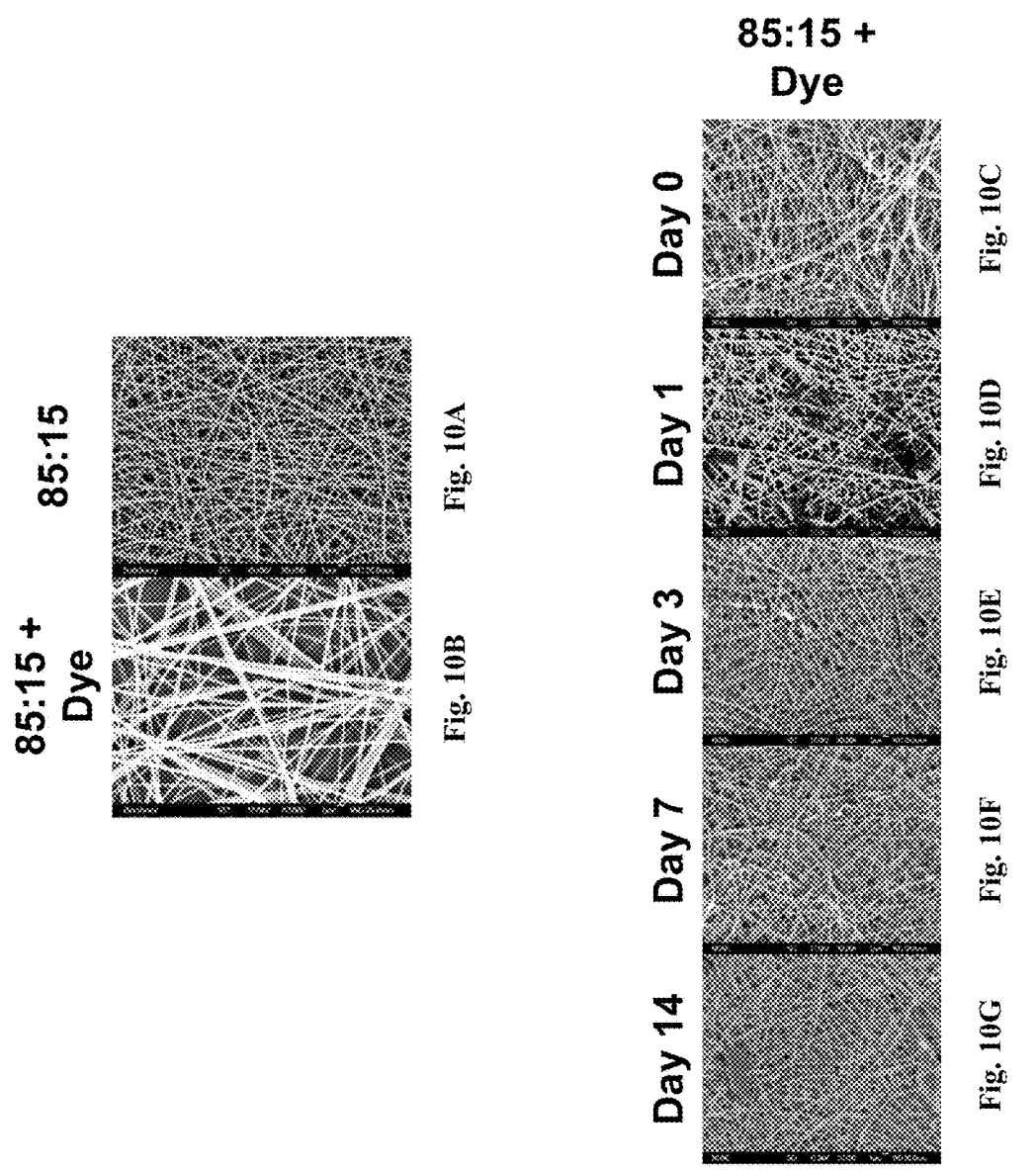

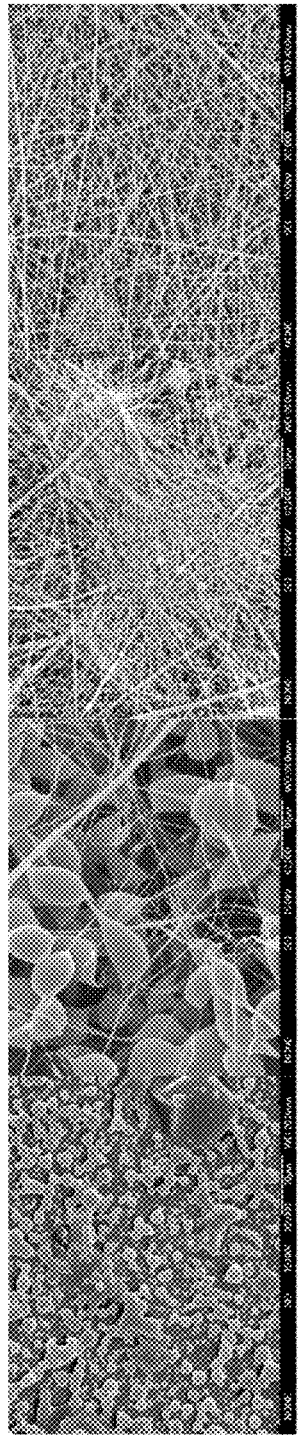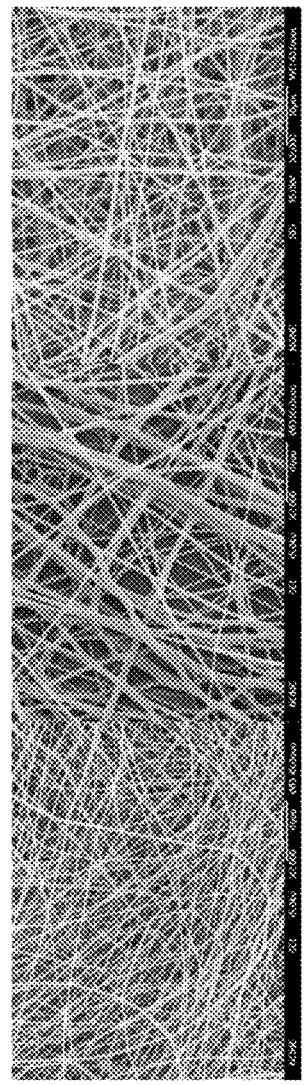
Fig. 11A  Fig. 11B  Fig. 11C  Fig. 11D  Fig. 11E  Fig. 11F  Fig. 11G

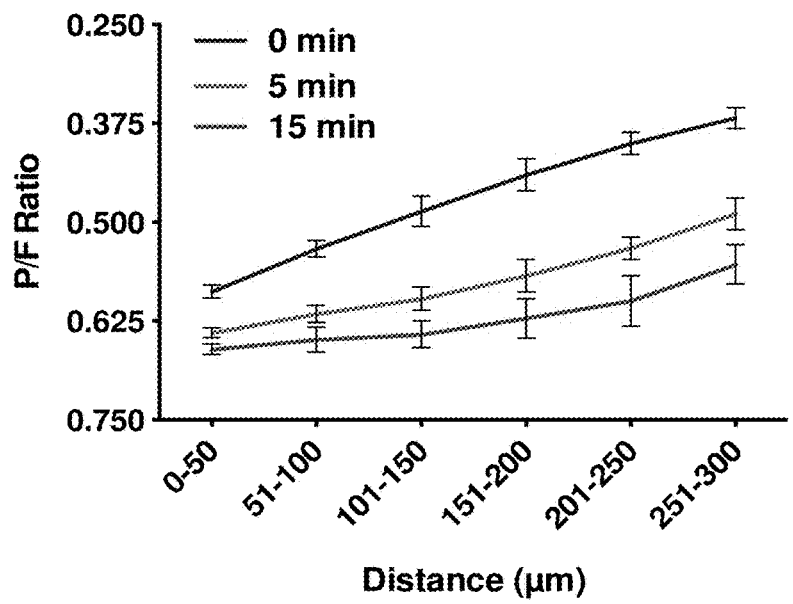
Fig. 12A
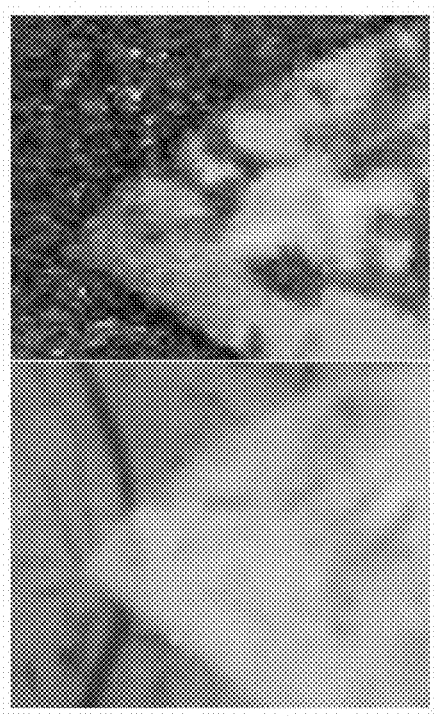
Fig. 12B
Fig. 12C

COMPOSITIONS AND METHODS FOR MAKING AND USING OXYGEN SENSING NANOFIBERS AND SCAFFOLDS

CROSS REFERENCE TO RELATED APPLICATIONS

This application is entitled to priority pursuant to 35 U.S.C. § 119(e) to U.S. provisional patent application No. 62/033,901, filed on Aug. 6, 2014. The entire disclosure of the afore-mentioned patent application is incorporated herein by reference.

STATEMENT REGARDING FEDERALLY SPONSORED RESEARCH OR DEVELOPMENT

This invention was made with government support under CBET0933643, CHE0718879 and EFMA0902969, awarded by The National Science Foundation and AR056445, DE019935, and CA167250 awarded by the National Institutes of Health. The government has certain rights in the invention.

BACKGROUND

Spatial oxygen gradients drive many cellular functions including cell migration, signaling, and differentiation. Sustained low oxygen tensions in tissue can impair the regenerative capacity and survival of tissue-engineered grafts. Therefore, the measurement of local oxygen concentration within a three-dimensional cell adherent scaffold is valuable in studying and tuning the dynamics of engineered graft success and integration.

Islet transplant will be a curative treatment for insulin dependent diabetes, not only increasing quality of life through reduced complications, but also decreasing the burden of self-management. In order for islet transplant to reach more patients with the benefits of normoglycemia, a number of challenges must be overcome. Encapsulation technology is rapidly developing, promising to be a part of the solution. From open porous scaffolds to diffusion barrier hydrogels, scaffolding and encapsulation materials can provide many desirable properties, including acting as a vehicle for therapeutic agents. The combination of multiple factors delivered in a temporally controlled fashion is likely to improve the long-term function of transplanted islets, defining a path toward greater future clinical success.

The Diabetes Control and Complications Trial (DCCT) established glucose control as an important factor in the progression of diabetic complications. Advances in insulin formulations and delivery methods since the discovery of insulin have made diabetes a chronic disease, with some patients having lived with the disease free of major complications for more than 50 years. However, the number of patients that can achieve complication preventative control despite using the best insulin self-management techniques and equipment available is limited and may be related to residual endogenous insulin production. The promise of tighter control by allowing pancreatic islets to perform their function has been the focus of intense research ever since the discovery that a transplant can cure a diabetic animal or human. Islet transplant is expected to be the major advance in clinical diabetes care following adoption of the closed loop artificial pancreas.

There is a long felt need in the art for compositions and methods useful for monitoring oxygen in tissue scaffolds and in transplants. The present invention satisfies these needs.

SUMMARY OF THE INVENTION

It is disclosed herein that a much stronger and better tissue engineering scaffold for sensing and measuring oxygen levels results when combining a boron-dye polymer nanofiber scaffold in with another polymer scaffold. The present invention therefore provides a multiple layered scaffold comprising at least one layer of nanofibers comprising a boron dye useful for sensing and determining oxygen levels and at least one layer of polymer nanofibers for structural support.

The present application explores the nanofabrication and material properties of a blended and conjugated formulation of boron dye and polymer electrospun into nanofibers for their application in biological research and in monitoring cells and tissues. Tissue engineering scaffolds must function in aqueous environments for periods of time from hours to weeks depending on the application. Spectrophotometric characterization of the blended dye and poly(lactic-co-glycolic acid) (PLAGA) formulation revealed low phosphorescence signal before and after exposure to aqueous media. The present application discloses the use of a poly(lactic acid) (i.e., polylactide) conjugated form of the boron dye as a method to improve performance of the tissue engineering scaffold. The polymer conjugated form of the dye was validated by calibration against various levels of hypoxia. Then the scaffold was utilized to detect oxygen variation in vitro and using hypoxia models in vivo. This material presents a useful tool in the real-time detection of localized oxygen gradients that could provide valuable information in the context of tissue engineering applications. The present application further discloses using two or more layers to form a scaffold and that each layer can comprise different components.

The present application discloses a dual emissive boron dye was used as a ratiometric oxygen sensor to enable understanding of the dynamic aspects of oxygen gradient responses in a non-invasive manner. While other oxygen sensing dyes have been utilized for real-time cell imaging, many require separate fluorophore standards that can be subject to differential degradation and photobleaching which may compromise their longevity and dynamic precision in vivo. The boron dyes of the invention emit an oxygen-sensitive phosphorescence signal and an oxygen-independent fluorescence signal. The ratio of the phosphorescence to the fluorescence (P/F ratio) produces an internally standardized ratiometric detection of molecular oxygen.

Several oxygen sensors have been blended with polyurethane, polystyrene, and polycaprolactone (PCL), to make micron and nanoscale biomaterials. As an additional example, we blended the oxygen sensitive boron-dye with poly(lactic-co-glycolic acid) (PLAGA) to electrospin nanofibers. While other material types have been made with this family of boron dyes, such as nanoparticles, nanofibers offer extracellular matrix (ECM) mimetic morphology. This is beneficial for the culture and control of many cell types such as Schwann cells, oligodendrocytes, neural progenitors, cardiomyocytes, osteoblasts, human skin fibroblasts, smooth muscle cells or endothelial cells, hepatocytes, mesenchymal stem cells, embryonic stem cells and induced pluripotent stem cells. Electrospinning is an ideal method for synthetic tissue engineering scaffold production because it allows tuning of the process parameters to create scaffolds of controlled morphology. The small diameter and large surface to volume ratio of nanofibers reduces the distance oxygen needs to diffuse within the polymer matrix to reach an embedded molecular sensor.

The molecular sensor of the invention can be covalently attached to polymers that degrade in aqueous environments. Disclosed herein are results using poly(lactic acid) (i.e., polylactide) conjugated form of the boron dye electrospun into nanofibers as a method to improve performance of the tissue engineering scaffold.

The present invention provides compositions and methods useful for scaffold-based oxygen concentration monitoring for cells and tissues.

In one embodiment, the present invention encompasses biodegradable electrospun polymer fibers, wherein an oxygen sensitive boron dye is included as part of a multiple layer scaffold. In one aspect, there are dual layers. In one aspect, the boron dye is conjugated to a polymer. In one aspect, the polymer to which the boron dye is conjugated is a PLA polymer. In one aspect, the boron dye layer is supported by a structural support layer, forming a dual layer scaffold. In one aspect, the structural support layer consists of blended poly(3-hydroxybutyrate-co-3-hydroxyvalerate) and polycaprolactone (PHBV and PCL) nanofibers. In one aspect, the dual layer scaffold has a mean nanofiber diameter that is intermediate to the nanofiber diameter of the support layer alone or the boron dye polymer layer alone. In one aspect, the tensile strength of the dual layer scaffold is greater than the tensile strength of the support layer alone.

In one embodiment, a self-referencing oxygen sensor is provided. In one aspect, the sensor is incorporated into nanofibers.

In one embodiment, a sensor of the invention is responsive to oxygen concentrations of less than 15 parts per million (ppm).

In one embodiment, nanofibers with controlled morphology comprising a conjugated oxygen sensitive dye are provided. In one aspect, the dye is a boron dye. In one aspect, the boron dye is a "difluoroboron dibenzoylmethane" ($BF_2dbmOH$) (see U.S. Pat. No. 7,955,861, the entirety of which is incorporated by reference herein).

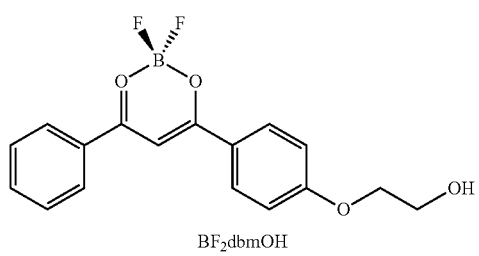

$BF_2dbmOH$ (1)

In another aspect, the present invention provides an iodinated version of $BF_2dmbOH$ for use in preparing a boron dye-polymer conjugate, that boron dye being $BF_2dbm$(I)OH. A useful dye-polymer conjugate using an iodinated version, that is, the dual-emissive, iodide-substituted difluoroboron dibenzoylmethane-poly(lactic acid) ($BF_2dbm(I)$PLA), a solid state sensor material (see "Embodiments" below and Zhang et al., 2009).

In one aspect, the boron dye is dual emissive. In one aspect, the dye emits an oxygen-sensitive signal and in one aspect it emits an oxygen-independent signal. In one aspect, one signal is phosphorescent. In one aspect, one signal is fluorescent. In one aspect, the two signals are not the same.

In one aspect, the present invention provides compositions and methods for preparation and use of an oxygen-sensing scaffold. In one aspect, the scaffold is useful as a transplant scaffold. In one aspect, it is useful for islet cell transplants. In one aspect, the scaffold comprises two layers.

Nanofibers of the invention can be prepared by electrospinning. In one aspect, the nanofibers are spun using a polymer and a dye. In one aspect, the polymer is a poly(lactic acid) (PLA) polymer. In one aspect, the polymer and dye are conjugated prior to electrospinning. In one aspect, the polymer is poly(lactic-co-glycolic acid (PLAGA).

In one aspect, a scaffold can be prepared with multiple layers of polymer nanofibers. In one aspect, two or more polymers can be combined for a base or structural support layer. In one aspect, two layers are used. Poly(3-hydroxybutyrate-co-3-hydroxyvalerate (PHBV) is a polyhydroxyalkanoate-type polymer. It is biodegradable, nontoxic, biocompatible plastic produced naturally by bacteria and a good alternative for many non-biodegradable synthetic polymers. It is a thermoplastic linear aliphatic polyester. Polycaprolactone (PCL) is a biodegradable polyester with a low melting point of around 60° C. and a glass transition temperature of about −60° C. In one aspect, at least one of these two polymers is used to make a base scaffold support layer upon which a boron dye-polymer conjugate containing nanofiber layer can be added.

In one embodiment, the boron dye containing nanofiber layer is fragile and is combined with a different polymer layer for better strength of the scaffold being used.

In one aspect, a scaffold of the invention can be prepared with or without the transplant tissue or cells and placed into a subject for preconditioning prior to the transplant being performed. In one aspect, the scaffold is placed at the site of the intended location of the transplant. In one aspect, the scaffold is placed subcutaneously into the subject. In one aspect, preconditioning can be done to ensure that the vascularization process begins. In one aspect, the preconditioning can be done ex vivo. In one aspect, once preconditioning occurs the scaffold can be moved. In one aspect, once preconditioning has occurred, the cells or tissue of the transplant are incorporated into the scaffold.

In one aspect, the scaffold of the invention is a sensor. In one aspect, the sensor of the invention activates quickly in vivo.

The oxygen sensing scaffold of the invention is also useful as a research tool to study oxygen-sensing once a transplant occurs or it can be used in vitro to monitor cells, tissues, or implanted tissues.

In one embodiment, additional agents can be prepared with/added to the nanofibers or to the scaffold.

In one embodiment, when a subject in which cells or tissues are in contact with a multilayered scaffold for measuring oxygen levels of said cells or tissues, the subject is administered a gas (a carbogen) and then oxygen levels of the cells or tissues are detected and measured. Standards or comparisons can include the use of air, $O_2$, or $N_2$.

The methods of the invention are useful for detecting oxygen level gradients across tissues or groups of cells being examined.

In one aspect, a time-dependent scaling factor is applied to the oxygen measurements when necessary to correct for reduction in phosphorescence intensity with time.

In one aspect, standard curves for relating P/F determinations to known oxygen concentrations can be prepared.

In one aspect, the scaffold of the invention is useful for determining dynamic changes in oxygen levels.

In one aspect, the scaffold of the invention is useful for detecting oxygen gradients in tissues or in monolayers of cells.

In one aspect, the scaffold of the invention is useful for determining a wide range of oxygen levels in cell culture and in vivo models, including detecting and determining hypoxic conditions.

The methods of the invention are useful for monitoring changes in oxygen levels during treatment of cells or tissues or during the course of a disease or disorder. It is disclosed herein that the composition of the invention provides enough stability that multiple measurements can be made for periods of time from minutes up to weeks. To ensure accurate measurements, accuracy standards can be prepared and used and the present invention also provides methods for use of a time-dependent scaling factor for application to the oxygen measurements when necessary to correct for any possible reduction in phosphorescence intensity with time. Tissues where oxygen levels can be determined include, but are not limited to, ischemic tissue, transplanted tissue, diseased tissue, and injured tissue. Transplanted tissue includes, but is not limited to, pancreatic islet tissue. The present invention is also useful for detecting hypoxia.

Various aspects and embodiments of the invention are described in further detail below.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

FIG. 2A-H. Nanofiber diameter for the three materials (FIG. 2A, mean±standard deviation). The water contact angle measurements of the three materials (FIG. 2B, n=3 for each group, mean±standard error, *p<0.05 compared to PHBV and PCL fibers), images (FIG. 2C, PHBV and PCL fibers; FIG. 2D, PHBV and PCL Boron Dye dual layer scaffold; FIG. 2E, boron dye PLA Fibers, mean±standard deviation). Confocal microscopy shows the boron dye layer (light green) over the PHBV and PCL layer (deep red) (FIG. 2F). Young's modulus (FIG. 2G) and ultimate tensile strength (FIG. 2H) suggest the boron dye layer attaches to the PHBV and PCL layer (n=3 for each group, mean±standard error, *p<0.05).

FIG. 3A-C. Ratiometric imaging of the dual layer scaffold with the support layer opposite the dye layer from the microscope objective (FIG. 3A), with the support layer between the objective and the dye layer (FIG. 3B) was found to be similar. Submersion in PBS with the dye layer closest to the microscope objective (FIG. 3C) demonstrates that the dye is still functional in a buffered media (n=5, standard error of the mean shown, *p<0.05, two-tailed independent means t-test).

FIG. 4A-J. Boron-dye sensor spectral response to low oxygen in dye-polymer conjugate nanofibers after incubation in aqueous media (FIG. 4A) (n=6 per time point) for 0, 7, 14, and 21 days (samples were lyophilized after indicated time in aqueous media and read in a nitrogen purged environment). Regression calculated exponential decay of polymer conjugate scaffold sensor maximum ratio after aqueous incubation for 7, 14, and 21 days (FIG. 4B). Under scanning electron microscopy the boron dye sensor layer swelled with time in aqueous media (FIG. 4C-F) while the support fibers maintained their structure (FIG. 4G-J). Scale bar 500 μm.

FIG. 6A-F. NIH3T3 cells were viable on the boron dye fibers (FIG. 6A, viable (fluorescein diacetate (FDA)); FIG. 6B, non-viable (propidium iodide (PI)); FIG. 6C, overlay). The mean P/F ratio of 5 radial traces (FIG. 6D) from the center of the cell mass (1 μm resolution) indicate the ability of the nanofibers to detect a gradient from the cell-containing to the cell-devoid regions and the change in signal with time after the chamber is closed to environmental oxygen (FIG. 6E-F). (FIG. 6E, colors indicate the scaffold area where the measured P/F ratio was greater than 0.5; FIG. 6F, average of the 5 traces at indicated time point).

Supporting FIGS. 1A-B, 2A-G, 3A-G, 4A-C, and 5 (can also be referred to as FIGS. 9A-B, 10A-G, 11A-G, 12A-C, and 13, respectively)

Figure 1A:
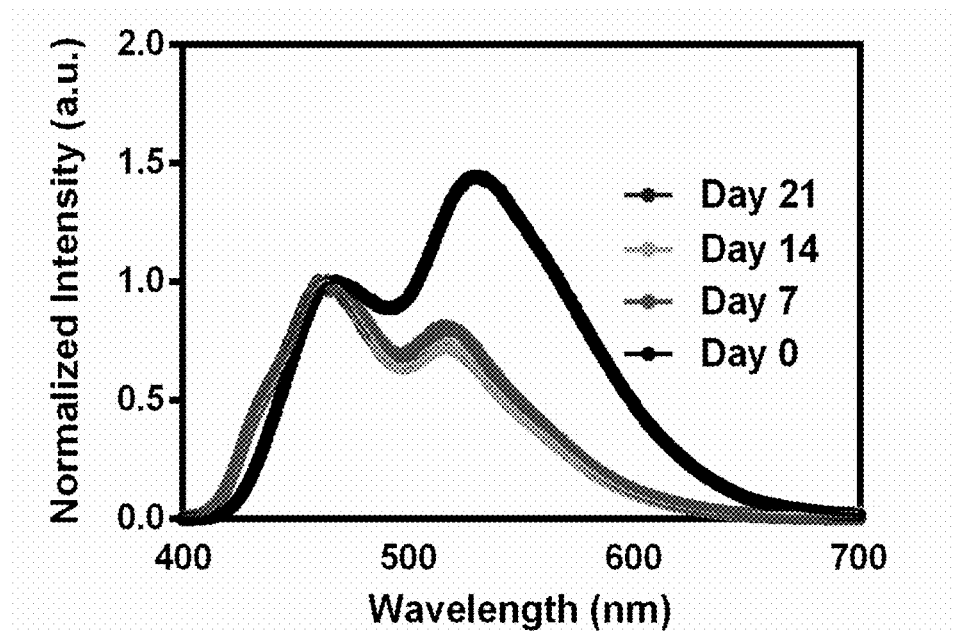
FIG. 1A-B. Boron-dye sensor spectral response to low oxygen after incubation in aqueous media in polymer blend nanofibers of 50:50 PLAGA at 0, 7, 14 and 21 days (FIG. 1A, samples were lyophilized after indicated time in aqueous media and read in a nitrogen purged environment). Fiber morphology of the 85:15 PLAGA nanofibers was maintained over a 14 day degradation study (FIG. 1B). Sensor spectral response to low oxygen environment (85:15 PLAGA blend at 0, 7 and 14 days) (FIG. 1C).
Figure 1B:
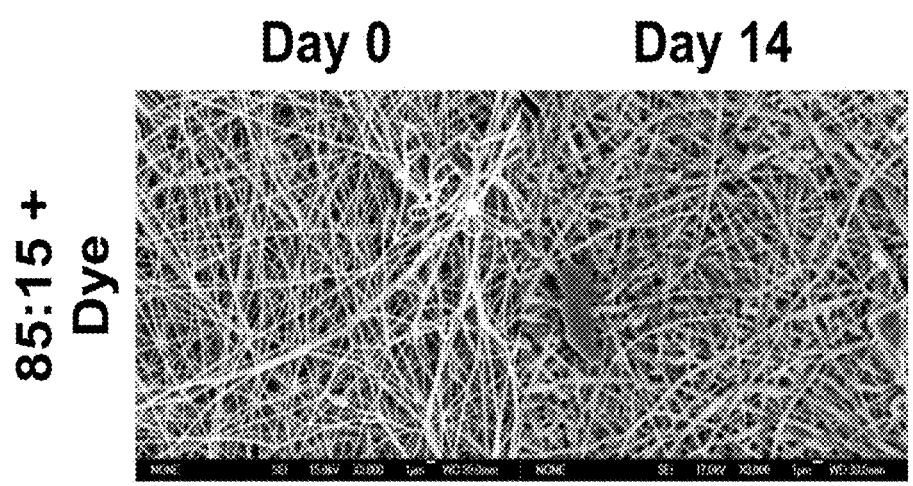

Supporting FIG. 1A-B (FIG. 9A-B): Blend normalized fluoroscopy characterization. Only on Day 0 is there a shoulder in the phosphorescence wavelength range under an air environment for the 50:50 blend (Supporting FIG. 1A). The delayed normalized phosphorescent peak of the 85:15 blend displayed a blue shift following increasing duration of polymer matrix degradation for 7 and 14 days (Supporting FIG. 1B).

Supporting FIG. 2A-G (FIG. 10A-G): Characterization following aqueous degradation. Adding the dye to a solution of PLGA (85:15 LA:GA subunit ratio) does not result in a loss of cylindrical fiber morphology (Supporting FIG. 2B) compared to the polymer alone (Supporting FIG. 2A) when the weight of the mixture was kept constant. The fiber morphology did not change noticeably over a 14 day degradation study as expected since the 85:15 polymer is known to be slow degrading (Supporting FIG. 2C, day 0; Supporting FIG. 2D, day 1; Supporting FIG. 2E, day 3; f Supporting FIG. 2F, day 7; Supporting FIG. 2G, day 14).

Supporting FIG. 3A-G (FIG. 11A-G): (Supporting FIG. 3A) The THF to DMF ratio was varied (30% w/v DMF:THF (3:1) shown) followed by (Supporting FIG. 3B) exploration of dichloromethane as a solvent (45% (w/v) PLA at 15 kV, at 14.5 cm at 1 mL/hr shown). (Supporting FIG. 3C) The addition of pyridinium formate improved the size and shape of the fibers dramatically, while (Supporting FIG. 3D) the addition of ethanol reduced beading and dripping. (Supporting FIG. 3E) The final parameters (see methods) were then applied to the boron dye conjugated PLA. The boron dye fibers were electrospun on a base of PHBV & PCL fibers (Supporting FIG. 3F) shown in the layered form under SEM (Supporting FIG. 3G).

Figure 4A:
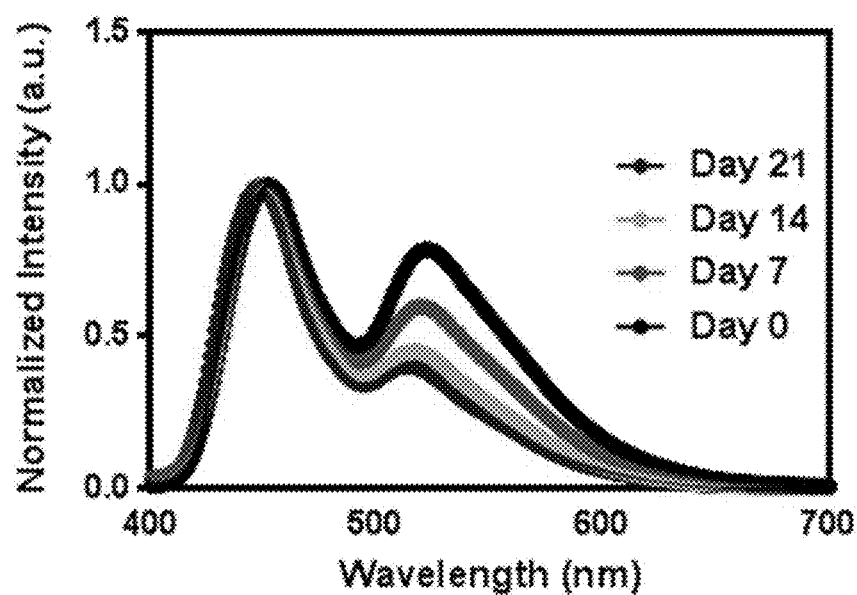
Figure 4B:
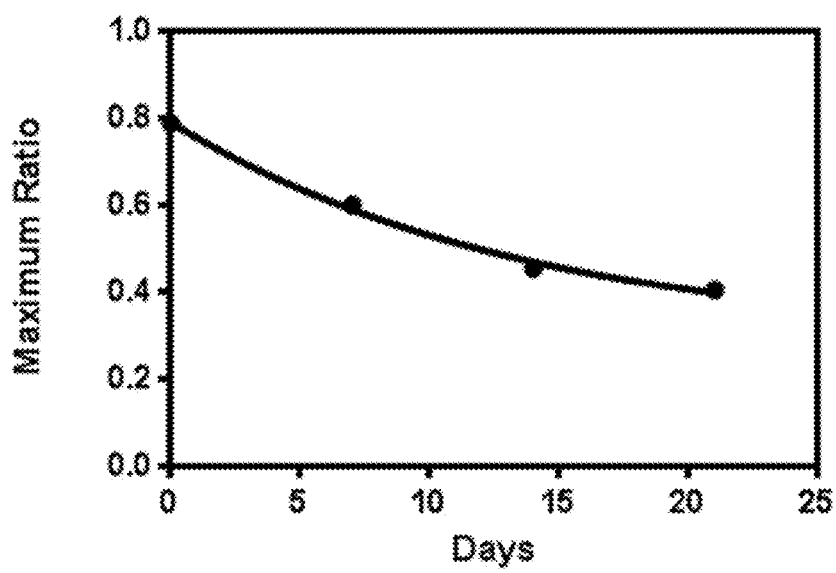

Supporting FIG. 4A-C (FIG. 12A-C): Scaffold gradients. Radial P/F measurements from one representative scaffold with a high density adherent cell cluster were binned in 50 μm increments (mean, SD). Ratio values were significantly different for all time points and distances (two-way ANOVA). (Supporting FIG. 4A). Nanofibers showed an oxygen gradient with radial distance from an arteriovenous pair of micro vessels. Ratiometric image (Supporting FIG. 4B) and corresponding brightfield image (Supporting FIG. 4C).

Supporting FIG. 5 (FIG. 13): Diagram of apparatus for controlling oxygen percentage. Curved arrows indicate the flow of gas through tubing in the apparatus.

DETAILED DESCRIPTION

Abbreviations and Acronyms

BF$_2$dbm(I)OH—Difluoroboron iodo-dibenzoylmethane
BNP—boron nanoparticle
DCCT—Diabetes Control and Complications Trial
DMEM—Dulbecco's Modified Eagle's Medium
DMF—dimethylformamide
E—Young's modulus
ECM—extracellular matrix
FDA—fluorescein diacetate
FBS—fetal bovine serum
GPC—gel permeation chromatography
HBSS—Hank's Balanced Salt Solution
P/F ratio—phosphorescence to fluorescence ratio
PF—pyridinium formate
PCL—polycaprolactone
PHBV—poly(hydroxylbutyrate-co-valerate)
PI—propidium iodide
PLA—poly(lactic acid)
PLAGA—poly(lactic-co-glycolic acid)
PLGA—polylactide-coglycolide
PPM—parts per million
SEM—scanning electron microscope
THF—tetrahydrofuran
UTS—ultimate tensile strength

Definitions

In describing and claiming the invention, the following terminology will be used in accordance with the definitions set forth below.

The articles "a" and "an" are used herein to refer to one or to more than one (i.e., to at least one) of the grammatical object of the article. By way of example, "an element" means one element or more than one element.

The term "about," as used herein, means approximately, in the region of, roughly, or around. When the term "about" is used in conjunction with a numerical range, it modifies that range by extending the boundaries above and below the numerical values set forth. For example, in one aspect, the term "about" is used herein to modify a numerical value above and below the stated value by a variance of 20%.

As used herein, "amino acids" are represented by the full name thereof, by the three letter code corresponding thereto, or by the one-letter code corresponding thereto, as indicated in the following table:

| Full Name | Three-Letter Code | One-Letter Code |
|---|---|---|
| Aspartic Acid | Asp | D |
| Glutamic Acid | Glu | E |
| Lysine | Lys | K |
| Arginine | Arg | R |
| Histidine | His | H |
| Tyrosine | Tyr | Y |
| Cysteine | Cys | C |
| Asparagine | Asn | N |
| Glutamine | Gln | Q |
| Serine | Ser | S |
| Threonine | Thr | T |
| Glycine | Gly | G |
| Alanine | Ala | A |
| Valine | Val | V |
| Leucine | Leu | L |
| Isoleucine | Ile | I |
| Methionine | Met | M |
| Proline | Pro | P |
| Phenylalanine | Phe | F |
| Tryptophan | Trp | W |

The expression "amino acid" as used herein is meant to include both natural and synthetic amino acids, and both D and L amino acids. "Standard amino acid" means any of the twenty standard L-amino acids commonly found in naturally occurring peptides. "Nonstandard amino acid residue" means any amino acid, other than the standard amino acids, regardless of whether it is prepared synthetically or derived from a natural source. As used herein, "synthetic amino acid" also encompasses chemically modified amino acids, including but not limited to salts, amino acid derivatives (such as amides), and substitutions. Amino acids contained within the peptides of the present invention, and particularly at the carboxy- or amino-terminus, can be modified by methylation, amidation, acetylation or substitution with other chemical groups which can change the peptide's circulating half-life without adversely affecting their activity. Additionally, a disulfide linkage may be present or absent in the peptides of the invention.

The term "amino acid" is used interchangeably with "amino acid residue," and may refer to a free amino acid and to an amino acid residue of a peptide. It will be apparent from the context in which the term is used whether it refers to a free amino acid or a residue of a peptide.

Amino acids have the following general structure:

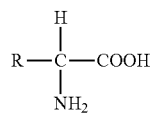

Amino acids may be classified into seven groups on the basis of the side chain R: (1) aliphatic side chains; (2) side chains containing a hydroxylic (OH) group; (3) side chains containing sulfur atoms; (4) side chains containing an acidic or amide group; (5) side chains containing a basic group; (6) side chains containing an aromatic ring; and (7) proline, an imino acid in which the side chain is fused to the amino group.

As used herein, the term "conservative amino acid substitution" is defined herein as exchanges within one of the following five groups:

I. Small aliphatic, nonpolar or slightly polar residues:
Ala, Ser, Thr, Pro, Gly;
II. Polar, negatively charged residues and their amides:
Asp, Asn, Glu, Gln;
III. Polar, positively charged residues:
His, Arg, Lys;
IV. Large, aliphatic, nonpolar residues:
Met Leu, Ile, Val, Cys
V. Large, aromatic residues:
Phe, Tyr, Trp The nomenclature used to describe the peptide compounds of the present invention follows the conventional practice wherein the amino group is presented to the left and the carboxy group to the right of each amino acid residue. In the formulae representing selected specific embodiments of the present invention, the amino- and carboxy-terminal groups, although not specifically shown, will be understood to be in the form they would assume at physiologic pH values, unless otherwise specified.

The term "basic" or "positively charged" amino acid, as used herein, refers to amino acids in which the R groups have a net positive charge at pH 7.0, and include, but are not limited to, the standard amino acids lysine, arginine, and histidine.

As used herein, an "analog" of a chemical compound is a compound that, by way of example, resembles another in structure but is not necessarily an isomer (e.g., 5-fluorouracil is an analog of thymine).

The term "bioactive laminin", as used herein, means laminin which maintains some or all of the biological properties of laminin.

The term bioactive is used interchangeably with "biologically active" and "functional".

The term "biocompatible," as used herein, refers to a material that does not elicit a substantial detrimental response in the host.

The term "biological sample," as used herein, refers to samples obtained from a living organism, including skin, hair, tissue, blood, plasma, cells, sweat, and urine.

The terms "cell" and "cell line," as used herein, may be used interchangeably. All of these terms also include their progeny, which are any and all subsequent generations. It is understood that all progeny may not be identical due to deliberate or inadvertent mutations.

The terms "cell culture" and "culture," as used herein, refer to the maintenance of cells in an artificial, in vitro environment. It is to be understood, however, that the term "cell culture" is a generic term and may be used to encompass the cultivation not only of individual cells, but also of tissues, organs, organ systems or whole organisms, for which the terms "tissue culture," "organ culture," "organ system culture" or "organotypic culture" may occasionally be used interchangeably with the term "cell culture."

The phrases "cell culture medium," "culture medium" (plural "media" in each case) and "medium formulation" refer to a nutritive solution for cultivating cells and may be used interchangeably.

By "chemically feasible" is meant a bonding arrangement or a compound where the generally understood rules of organic structure are not violated; for example a structure within a definition of a claim that would contain in certain situations a pentavalent carbon atom that would not exist in nature would be understood to not be within the claim. The structures disclosed herein, in all of their embodiments are intended to include only "chemically feasible" structures, and any recited structures that are not chemically feasible, for example in a structure shown with variable atoms or groups, are not intended to be disclosed or claimed herein.

When a substituent is specified to be an atom or atoms of specified identity, "or a bond", a configuration is referred to when the substituent is "a bond" that the groups that are immediately adjacent to the specified substituent are directly connected to each other in a chemically feasible bonding configuration.

All chiral, diastereomeric, racemic forms of a structure are intended, unless a particular stereochemistry or isomeric form is specifically indicated. Compounds used in the present invention can include enriched or resolved optical isomers at any or all asymmetric atoms as are apparent from the depictions, at any degree of enrichment. Both racemic and diastereomeric mixtures, as well as the individual optical isomers can be isolated or synthesized so as to be substantially free of their enantiomeric or diastereomeric partners, and these are all within the scope of the invention.

A "compound," as used herein, refers to a polypeptide, an isolated nucleic acid, and to any type of substance or agent that is commonly considered a chemical, drug, or a candidate for use as a drug, as well as combinations and mixtures of the above.

A "conditioned medium" is one prepared by culturing a first population of cells or tissue in a medium, and then harvesting the medium. The conditioned medium (along with anything secreted into the medium by the cells) may then be used to support the growth or differentiation of a second population of cells.

The term "culture container" as used herein means a receptacle for holding media for culturing a cell or tissue. The culture container may, for example, be glass or plastic. Preferably the plastic is non-cytotoxic. The term culture container includes, but is not limited to, single and multiwell culture plates, chambered and multi-chambered culture slides, coverslips, cups, flasks, tubes, bottles, roller bottles, spinner bottles, perfusion chambers, bioreactors, and fermenters.

"Cytokine," as used herein, refers to intercellular signaling molecules, the best known of which are involved in the regulation of mammalian somatic cells. A number of families of cytokines, both growth promoting and growth inhibitory in their effects, have been characterized including, for example, interleukins, interferons, and transforming growth factors. A number of other cytokines are known to those of skill in the art. The sources, characteristics, targets, and effector activities of these cytokines have been described.

The term "delivery vehicle" refers to any kind of device or material which can be used to deliver cells in vivo or can be added to a composition comprising cells administered to an animal. This includes, but is not limited to, implantable devices, matrix materials, gels, etc.

The use of the word "detect" and its grammatical variants is meant to refer to measurement of the species without quantification, whereas use of the word "determine" or "measure" with their grammatical variants are meant to refer to measurement of the species with quantification. The terms "detect" and "identify" are used interchangeably herein.

As used herein, a "detectable marker" or a "reporter molecule" is an atom or a molecule that permits the specific detection of a compound comprising the marker in the presence of similar compounds without a marker. Detectable markers or reporter molecules include, e.g., radioactive isotopes, antigenic determinants, enzymes, nucleic acids available for hybridization, chromophores, fluorophores, chemiluminescent molecules, electrochemically detectable molecules, and molecules that provide for altered fluorescence-polarization or altered light-scattering.

The term "differentiation factor" as used herein means a bioactive molecule that promotes the differentiation of cells. The term includes, but is not limited to, neurotrophin, colony stimulating factor (CSF), or transforming growth factor. CSF includes granulocyte-CSF, macrophage-CSF, granulocyte-macrophage-CSF, erythropoietin, and IL-3. Some differentiation factors may also promote the growth of a cell or tissue. TGF and IL-3, for example, may promote differentiation and/or growth of cells.

A "disease" is a state of health of an animal wherein the animal cannot maintain homeostasis, and wherein if the disease is not ameliorated then the animal's health continues to deteriorate. In contrast, a "disorder" in an animal is a state of health in which the animal is able to maintain homeostasis, but in which the animal's state of health is less favorable than it would be in the absence of the disorder. Left untreated, a disorder does not necessarily cause a further decrease in the animal's state of health.

A disease or disorder is "alleviated" if the severity of a symptom of the disease or disorder, the frequency with which such a symptom is experienced by a patient, or both, are reduced.

A "disease or disorder associated with aberrant osteoclast activity" refers to a disease or disorder comprising either increased or decreased: osteoclast activity; numbers of osteoclasts; or numbers of osteoclast precursors.

A "dispensing container" refers to a vessel such as a syringe, which is used in the process of electrospinning. The syringe may have a needle attached and the gauge may be varied, depending in the particular conditions needed when electrospinning.

"Electroaerosoling" means a process in which droplets are formed from a solution or melt by streaming a solution or melt through an orifice in response to an electric field.

"The terms "electroprocessing" and "electrodeposition" shall be defined broadly to include all methods of electrospinning, electrospraying, electroaerosoling, and electrosputtering of materials, combinations of two or more such methods, and any other method wherein materials are streamed, sprayed, sputtered, or dripped across an electric field and toward a target. The electroprocessed material can be electroprocessed from one or more grounded reservoirs in the direction of a charged substrate or from charged reservoirs toward a grounded target. The term electroprocessing is not limited to the specific examples set forth herein, and it includes any means of using an electrical field for depositing a material on a target. The material may be in the form of fibers, powder, droplets, particles, or any other form. The target may be a solid, semisolid, liquid, or any other material.

"Electrospinning" means a process in which fibers are formed from a solution or melt by streaming a solution or melt through an orifice in response to an electric field.

As used herein, a "functional" molecule is a molecule in a form in which it exhibits a property or activity by which it is characterized. A functional enzyme, for example, is one that exhibits the characteristic catalytic activity by which the enzyme is characterized.

A "fragment" or "segment" is a portion of an amino acid sequence, comprising at least one amino acid, or a portion of a nucleic acid sequence comprising at least one nucleotide. The terms "fragment" and "segment" are used interchangeably herein. A "biologically active fragment" of a peptide or protein is one which retains activity of the parent peptide such as binding to a natural ligand or performing the function of the protein.

As used herein, a "functional" biological molecule is a biological molecule in a form in which it exhibits a property or activity by which it is characterized. A functional enzyme, for example, is one which exhibits the characteristic catalytic activity by which the enzyme is characterized.

"Graft" refers to any free (unattached) cell, tissue, or organ for transplantation.

"Allograft" refers to a transplanted cell, tissue, or organ derived from a different animal of the same species.

"Xenograft" refers to a transplanted cell, tissue, or organ derived from an animal of a different species.

The term "growth factor" as used herein means a bioactive molecule that promotes the proliferation of a cell or tissue. Growth factors useful in the present invention include, but are not limited to, transforming growth factor-alpha (TGF-$\alpha$), transforming growth factor-beta (TGF-$\beta$), platelet-derived growth factors including the AA, AB and BB isoforms (PDGF), fibroblast growth factors (FGF), including FGF acidic isoforms 1 and 2, FGF basic form 2, and FGF 4, 8, 9 and 10, nerve growth factors (NGF) including NGF 2.5 s, NGF 7.0 s and beta NGF and neurotrophins, brain derived neurotrophic factor, cartilage derived factor, bone growth factors (BGF), basic fibroblast growth factor, insulin-like growth factor (IGF), vascular endothelial growth factor (VEGF), EG-VEGF, VEGF-related protein, Bv8, VEGF-E, granulocyte colony stimulating factor (G-CSF), insulin like growth factor (IGF) I and II, hepatocyte growth factor, glial neurotrophic growth factor, stem cell factor (SCF), keratinocyte growth factor (KGF), skeletal growth factor, bone matrix derived growth factors, and bone derived growth factors and mixtures thereof. Some growth factors may also promote differentiation of a cell or tissue. TGF, for example, may promote growth and/or differentiation of a cell or tissue.

A "heavy atom" as the term is used herein refers to an atom of an element with an atomic mass greater than that of argon.

"Homologous" as used herein, refers to the subunit sequence similarity between two polymeric molecules, e.g., between two nucleic acid molecules, e.g., two DNA molecules or two RNA molecules, or between two polypeptide molecules. When a subunit position in both of the two molecules is occupied by the same monomeric subunit, e.g., if a position in each of two DNA molecules is occupied by adenine, then they are homologous at that position. The homology between two sequences is a direct function of the number of matching or homologous positions, e.g., if half (e.g., five positions in a polymer ten subunits in length) of the positions in two compound sequences are homologous then the two sequences are 50% homologous, if 90% of the positions, e.g., 9 of 10, are matched or homologous, the two sequences share 90% homology. By way of example, the DNA sequences 3'ATTGCC5' and 3'TATGGC share 50% homology.

As used herein, "homology" is used synonymously with "identity."

The determination of percent identity between two nucleotide or amino acid sequences can be accomplished using a mathematical algorithm. For example, a mathematical algorithm useful for comparing two sequences is the algorithm of Karlin and Altschul (1990, Proc. Natl. Acad. Sci. USA 87:2264-2268), modified as in Karlin and Altschul (1993, Proc. Natl. Acad. Sci. USA 90:5873-5877). This algorithm is incorporated into the NBLAST and XBLAST programs of Altschul, et al. (1990, J. Mol. Biol. 215:403-410), and can be accessed, for example at the National Center for Biotechnology Information (NCBI) world wide web site. BLAST nucleotide searches can be performed with the NBLAST program (designated "blastn" at the NCBI web site), using the following parameters: gap penalty=5; gap extension penalty=2; mismatch penalty=3; match reward=1; expectation value 10.0; and word size=11 to obtain nucleotide sequences homologous to a nucleic acid described herein. BLAST protein searches can be performed with the XBLAST program (designated "blastn" at the NCBI web site) or the NCBI "blastp" program, using the following parameters: expectation value 10.0, BLOSUM62 scoring matrix to obtain amino acid sequences homologous to a protein molecule described herein. To obtain gapped alignments for comparison purposes, Gapped BLAST can be utilized as described in Altschul et al. (1997, Nucleic Acids Res. 25:3389-3402). Alternatively, PSI-Blast or PHI-Blast can be used to perform an iterated search which detects distant relationships between molecules (Id.) and relationships between molecules which share a common pattern. When utilizing BLAST, Gapped BLAST, PSI-Blast, and PHI-Blast programs, the default parameters of the respective programs (e.g., XBLAST and NBLAST) can be used.

The percent identity between two sequences can be determined using techniques similar to those described above, with or without allowing gaps. In calculating percent identity, typically exact matches are counted.

The term "ingredient" refers to any compound, whether of chemical or biological origin, that can be used in cell culture media to maintain or promote the growth or proliferation of cells. The terms "component," "nutrient" and ingredient" can be used interchangeably and are all meant to refer to such compounds. Typical non-limiting ingredients that are used in cell culture media include amino acids, salts, metals, sugars, lipids, nucleic acids, hormones, vitamins, fatty acids, proteins and the like. Other ingredients that promote or maintain cultivation of cells ex vivo can be selected by those of skill in the art, in accordance with the particular need.

The term "inhibit," as used herein, means to suppress or block an activity or function such that it is lower relative to a control value. The inhibition can be via direct or indirect mechanisms. In one aspect, the activity is suppressed or blocked by at least 10% compared to a control value, more preferably by at least 25%, and even more preferably by at least 50%. The term "inhibitor" as used herein, refers to any compound or agent, the application of which results in the inhibition of a process or function of interest, including, but not limited to, differentiation and activity. Inhibition can be inferred if there is a reduction in the activity or function of interest.

The term "injury" refers to any physical damage to the body caused by violence, accident, trauma, or fracture, etc.

As used herein, an "instructional material" includes a publication, a recording, a diagram, or any other medium of expression which can be used to communicate the usefulness of the composition of the invention for its designated use. The instructional material of the kit of the invention may, for example, be affixed to a container which contains the composition or be shipped together with a container which contains the composition. Alternatively, the instructional material may be shipped separately from the container with the intention that the instructional material and the composition be used cooperatively by the recipient.

As used herein, the term "insult" refers to injury, disease, or contact with a substance or environmental change that results in an alteration of tissue or normal cellular metabolism in a tissue, cell, or population of cells.

An "isolated nucleic acid" refers to a nucleic acid segment or fragment which has been separated from sequences which flank it in a naturally occurring state, e.g., a DNA fragment which has been removed from the sequences which are normally adjacent to the fragment, e.g., the sequences adjacent to the fragment in a genome in which it naturally occurs. The term also applies to nucleic acids which have been substantially purified from other components which naturally accompany the nucleic acid, e.g., RNA or DNA or proteins, which naturally accompany it in the cell. The term therefore includes, for example, a recombinant DNA which is incorporated into a vector, into an autonomously replicating plasmid or virus, or into the genomic DNA of a prokaryote or eukaryote, or which exists as a separate molecule (e.g., as a cDNA or a genomic or cDNA fragment produced by PCR or restriction enzyme digestion) independent of other sequences. It also includes a recombinant DNA which is part of a hybrid gene encoding additional polypeptide sequence.

The term "laminin nanofibrillar structure supports the proliferation and differentiation of cells", should not be construed to mean that it must support both proliferation and differentiation of a specific cell, but should be construed in the broad sense of being able to support the proliferation and/or differentiation of many cell types. Additionally, the term does not mean that additional things such as supplements, growth factors, and differentiation factors do not need to be added when culturing a particular cell type in an effort to support its growth and/or differentiation.

Unless otherwise specified, a "nucleotide sequence encoding an amino acid sequence" includes all nucleotide sequences that are degenerate versions of each other and that encode the same amino acid sequence. Nucleotide sequences that encode proteins and RNA may include introns.

As used herein, the term "linkage" refers to a connection between two groups. The connection can be either covalent or non-covalent, including but not limited to ionic bonds, hydrogen bonding, and hydrophobic/hydrophilic interactions.

As used herein, the term "linker" refers to a molecule that joins two other molecules either covalently or noncovalently, e.g., through ionic or hydrogen bonds or van der Waals interactions. As used herein, the term "nucleic acid" encompasses RNA as well as single and double-stranded DNA and cDNA. Furthermore, the terms, "nucleic acid," "DNA," "RNA" and similar terms also include nucleic acid analogs, i.e. analogs having other than a phosphodiester backbone. For example, the so-called "peptide nucleic acids," which are known in the art and have peptide bonds instead of phosphodiester bonds in the backbone, are considered within the scope of the present invention.

The terms "luminescence", "luminescing", "luminescent", and related words as used herein refer to phosphorescence and/or fluorescence; i.e., the terms refer to the total release of photons other than by simple reflectance by a substance when placed under illumination, such as by a source of ultraviolet light, regardless of the physical mechanism by which such emission occurs. Typically, ultraviolet light of wavelength ($\lambda$ex) is used to stimulate emission of photons from the luminescent composition, which has a characteristic emission spectrum (λem), quantum efficiency (ΦF) and excited state decay constant (τf).

The term "material" refers to any compound, molecule, substance, or group or combination thereof that forms any type of structure or group of structures during or after electroprocessing. Materials include natural materials, synthetic materials, or combinations thereof. Naturally occurring organic materials include any substances naturally found in the body of plants or other organisms, regardless of whether those materials have or can be produced or altered synthetically. Synthetic materials include any materials prepared through any method of artificial synthesis, processing, or manufacture. Preferably, the materials are biologically compatible materials.

"Mechanochromic", "mechanochromism", "mechanoresponsive," and related terms as used herein refer to the phenomenon of a substance changing color upon mechanical disturbance, perturbation, pressure, shearing/smearing, or the like. In the present invention, the terms "mechanochromic", etc., refers to changes in the luminescent emission spectrum of light from a solid-state composition after mechanical disturbance, rather than to the color of the composition as viewed in visible light; thus the phenomenon referred to is specifically "mechanochromic luminescence" throughout. A mechanochromic luminescent effect can be observed after disturbance or pressure of a solid-state composition of the invention as applied by a solid physical object (swab tip, pencil eraser, artist's brush), a stream of gas (a breath), a stream of a liquid such as water, the impression of a solid stamp, pressure applied by a piston or other device for transmitting pressure, cellular adhesion, migration, mechanically active tissues and organs, or the like. The mechanochromic luminescent effect is observed in the luminescence of the perturbed solid under illumination by UV light.

The term "mesh" as used herein, refers to a collection of nanofibers, particularly two or more non-woven layers of polymer nanofibers and thus the mesh comprises what is referred to herein as a "nanofibrillar structure". Nanofibers within the mesh may be either randomly oriented or are deposited in a controlled fashion, such as aligned in parallel. Such a mesh comprises both nanofibers and "pores" (spaces not occupied by fibers).

The term "nanofiber" as used herein means a fiber comprising a diameter of about 1000 nanometers or less. The term "nanofiber" is use interchangeably with "nanofiber network" and "nanofiber mesh" herein.

The term "nanofibrillar structure" as used herein means a structure comprising one or more nanofibers, wherein the structure is defined by a network or mesh of one or more nanofibers. In some embodiments, the nanofibrillar structure comprises a substrate wherein the nanofibrillar structure is defined by a network of one or more nanofibers deposited on a surface of the substrate. The nanotopography, the topography of the nanofiber network and the arrangement of the nanofibers of the nanofiber network in space, is engineered to provide an in vitro biomimetic substratum that is more tissue compatible for the promotion of homotypic or heterotypic cell growth and/or cell differentiation in single layer or multi-layered cell culture. The nanofibrillar structures may be layered to form a multi-layered nanofibrillar assembly, cellular array, or tissue structure.

The term "network" as used herein means a random or oriented distribution of nanofibers in space that is controlled to form an interconnecting net with spacing between fibers selected to promote growth and culture stability. Physical properties of the network including, but not limited to, texture, rugosity, adhesivity, porosity, solidity, elasticity, geometry, interconnectivity, surface to volume ratio, fiber diameter, fiber solubility/insolubility, hydrophilicity/hydrophobicity, fibril density, and fiber orientation may be engineered to desired parameters.

As used herein, the term "pharmaceutically acceptable carrier" includes any of the standard pharmaceutical carriers, such as a phosphate buffered saline solution, water, emulsions such as an oil/water or water/oil emulsion, and various types of wetting agents. The term also encompasses any of the agents approved by a regulatory agency of the US Federal government or listed in the US Pharmacopeia for use in animals, including humans.

"Plurality" means at least two.

"Polypeptide" refers to a polymer composed of amino acid residues, related naturally occurring structural variants, and synthetic non-naturally occurring analogs thereof linked via peptide bonds, related naturally occurring structural variants, and synthetic non-naturally occurring analogs thereof. Synthetic polypeptides can be synthesized, for example, using an automated polypeptide synthesizer.

The term "protein" typically refers to large polypeptides.

The term "peptide" typically refers to short polypeptides.

A "recombinant polypeptide" is one which is produced upon expression of a recombinant polynucleotide.

A peptide encompasses a sequence of 2 or more amino acids wherein the amino acids are naturally occurring or synthetic (non-naturally occurring) amino acids.

Peptide mimetics include peptides having one or more of the following modifications:

1. peptides wherein one or more of the peptidyl —C(O)NR— linkages (bonds) have been replaced by a non-peptidyl linkage such as a —CH2-carbamate linkage (—CH2OC(O)NR—), a phosphonate linkage, a —CH2-sulfonamide (—CH 2-S(O)2NR—) linkage, a urea (—NHC(O)NH—) linkage, a —CH2-secondary amine linkage, or with an alkylated peptidyl linkage (—C(O)NR—) wherein R is C1-C4 alkyl;

2. peptides wherein the N-terminus is derivatized to a —NRR1 group, to a —NRC(O)R group, to a —NRC(O)OR group, to a —NRS(O)2R group, to a —NHC(O)NHR group where R and R1 are hydrogen or C1-C4 alkyl with the proviso that R and R1 are not both hydrogen;

3. peptides wherein the C terminus is derivatized to —C(O)R2 where R 2 is selected from the group consisting of C1-C4 alkoxy, and —NR3R4 where R3 and R4 are independently selected from the group consisting of hydrogen and C1-C4 alkyl.

The term "pumping said laminin dissolved in HFP through an opening in said dispensing container" refers to the route in which laminin is electrospun, such as through the tip of a syringe.

As used herein, the term "purified" and like terms relate to an enrichment of a cell, cell type, molecule, or compound relative to other components normally associated with the cell, cell type, molecule, or compound in a native environment. The term "purified" does not necessarily indicate that complete purity of the particular cell, cell type, molecule, or compound has been achieved during the process.

A "reversibly implantable" device is one which may be inserted (e.g. surgically or by insertion into a natural orifice of the animal) into the body of an animal and thereafter removed without great harm to the health of the animal.

A "salt" as is well known in the art includes an organic compound such as a carboxylic acid, a sulfonic acid, or an amine, in ionic form, in combination with a counterion. For example, acids in their anionic form can form salts with cations such as metal cations, for example sodium, potassium, and the like; with ammonium salts such as $NH_4^+$ or the cations of various amines, including tetraalkyl ammonium salts such as tetramethylammonium, or other cations such as trimethylsulfonium, and the like. Other salt-forming ions include triflate, tosylate, $PF_6^-$, $BF_4^-$, and $BPh_4^-$.

A "sample," as used herein, refers preferably to a biological sample from a subject, including, but not limited to, normal tissue samples, diseased tissue samples, biopsies, blood, saliva, feces, semen, tears, and urine. A sample can also be any other source of material obtained from a subject which contains cells, tissues, or fluid of interest. A sample can also be obtained from cell or tissue culture.

By "small interfering RNAs (siRNAs)" is meant, inter alia, an isolated dsRNA molecule comprised of both a sense and an anti-sense strand. In one aspect, it is greater than 10 nucleotides in length. siRNA also refers to a single transcript which has both the sense and complementary antisense sequences from the target gene, e.g., a hairpin. siRNA further includes any form of dsRNA (proteolytically cleaved products of larger dsRNA, partially purified RNA, essentially pure RNA, synthetic RNA, recombinantly produced RNA) as well as altered RNA that differs from naturally occurring RNA by the addition, deletion, substitution, and/or alteration of one or more nucleotides.

A "solid-state" composition, as the term is used herein, refers to a material that is a solid at the temperature examined (usually room temperature, about 20° C.), that is not dissolved in a liquid solvent but is in the physical state of a solid, which can be amorphous, crystalline, in a film, in bulk, and so forth. The solid compositions of the invention can be used individually or in combination as films, coatings, or blends in combination with other solid matrices or substrates (e.g. paper, plastic, polymer, glass, quartz, etc).

The term "standard," as used herein, refers to something used for comparison. For example, a standard can be a known standard agent or compound which is administered or added to a control sample and used for comparing results when measuring said compound in a test sample. Standard can also refer to an "internal standard," such as an agent or compound which is added at known amounts to a sample and is useful in determining such things as purification or recovery rates when a sample is processed or subjected to purification or extraction procedures before a marker of interest is measured.

A "subject" of analysis, diagnosis, or treatment is an animal. Such animals include mammals, preferably a human.

As used herein, a "subject in need thereof" is a patient, animal, mammal or human, who will benefit from the method of this invention.

The term "substantially pure" describes a compound, e.g., a protein or polypeptide or other compound which has been separated from components which naturally accompany it. Typically, a compound is substantially pure when at least 10%, more preferably at least 20%, more preferably at least 50%, more preferably at least 60%, more preferably at least 75%, more preferably at least 90%, and most preferably at least 99% of the total material (by volume, by wet or dry weight, or by mole percent or mole fraction) in a sample is the compound of interest. Purity can be measured by any appropriate method, e.g., in the case of polypeptides by column chromatography, gel electrophoresis, or HPLC analysis. A compound, e.g., a protein, is also substantially purified when it is essentially free of naturally associated components or when it is separated from the native contaminants which accompany it in its natural state.

The term "substrate" as used herein means any surface on which electrospun nanofibers, meshes or networks of nanofibers are deposited. The substrate may be any surface that offers structural support for the deposited network or mesh of nanofibers. The substrate may comprise, for example, glass or plastic. Preferably, the plastic is non-cytotoxic. The substrate may, for example, be a film or culture container. "Substrate" should be interpreted to mean not just a surface upon which material can be deposited, but additionally the surface and the materials that have been deposited upon it.

As used herein, the term "treating" includes prophylaxis of a specific disease, disorder, or condition, or alleviation of the symptoms associated with a specific disorder or condition and/or preventing or eliminating said symptoms. A "prophylactic" treatment is a treatment administered to a subject who does not exhibit signs of a disease or exhibits only early signs of the disease for the purpose of decreasing the risk of developing pathology associated with the disease.

A "therapeutic" treatment is a treatment administered to a subject who exhibits signs of pathology for the purpose of diminishing or eliminating those signs.

A "therapeutically effective amount" of a compound is that amount of compound which is sufficient to provide a beneficial effect to the subject to which the compound is administered.

As used herein, the term "wound" relates to a physical tear or rupture to a tissue or cell layer. A wound may occur by any physical insult, including a surgical procedure.

Embodiments

The present invention provides a multiple layered tissue engineering scaffold for measuring oxygen levels in tissues or cells. The multiple layered scaffold comprises at least one electrospun boron dye-polymer conjugate nanofiber layer and at least one electrospun structural support nanofiber layer. In one aspect, the boron dye emits a phosphorescence signal and a fluorescence signal and the ratio of the emitted signals is dependent on the oxygen levels present. In one aspect, the multiple layered scaffold consists of one electrospun boron dye-polymer conjugate nanofiber layer and one electrospun structural support nanofiber layer.

In one aspect, the electrospinning process parameters for the dye-polymer conjugate nanofiber layer are 30% (weight/volume) dye-polymer in 10% (volume/volume) pyridinium formate, 20% (volume/volume) ethanol, in dichloromethane at a 25 kV applied voltage, 14.5 cm working distance, and a solution flow rate of 1 mL/hr. In one aspect, the dye-polymer conjugate nanofibers are electrospun onto the structural support nanofiber layer. In one aspect, the structural support nanofiber layer is dry when the dye-polymer conjugate nanofibers are electrospun onto it.

In one embodiment of the multiple layered scaffold of the invention, the structural support nanofiber layer comprises at least two polymers selected. In one aspect, useful polymers include, but are not limited to, poly(3-hydroxybutyrate-co-3-hydroxyvalerate) (PHBV), polycaprolactone (PCL), poly-lactide-coglycolide (PLGA), polystyrene, poly(lactic acid) (PLA), poly (l-lactic acid) (PLLA), polyglycolic acid (PGA), copolymers of PLA and PGA, poly(ethylene-co-vinyl acetate) (EVOH), poly(vinyl acetate) (PVA), polyethylene glycol (PEG), poly(glycerol sebacate) (PGS), poly(d,l-lactic-co-glycolic acid 50:50) (PLGA5050), poly(d-l-lactic-co-glycolic acid 85:15) (PLGA8515), polydioxanone (PDO), polyphosphazenes, polyurethane (PU), polyhydroxybutyrates (PHB), poly-3-hydroxybutyrate (P3HB), poly-4-hydroxybutyrate (P4HB), polyhydroxyvalerate (PHV), polyhydroxyhexanoate (PHH), polyhydroxyoctanoate (PHO), and poly(ethylene oxide) (PEO), and co-polymers, analogs, derivatives, modifications, and mixtures thereof. In one aspect, the structural support nanofiber layer consists of two polymers. In one aspect, the two polymers are PHBV and PCL.

In one aspect of the multiple layered scaffold of the invention, difluoroboron dibenzoylmethane ($BF_2dbmOH$) or iodide substituted difluoroboron dibenzoylmethane ($BF_2dbm(I)OH$) are used to prepare the boron dye-polymer conjugate for use in the sensor layer.

In one aspect, the boron dye-polymer conjugate nanofiber layer is electrospun onto the electrospun structural support nanofiber layer.

In one embodiment, the boron dye is dual emissive for fluorescence and phosphorescence. In one aspect, the boron dye emits a phosphorescence signal and a fluorescence signal. In one aspect, the ratio of the two different signals changes when oxygen levels change. In one aspect, the phosphorescence signal is oxygen sensitive and the fluorescence signal is oxygen insensitive.

In one embodiment of the multiple layered scaffold, the ratio of the oxygen sensitive phosphorescence signal to the oxygen insensitive fluorescence signal is calculated to determine an oxygenation value for the cells or tissues being used.

In one embodiment, the present invention provides compositions and methods useful for determining oxygen levels using the multiple layer scaffold of the invention. In one aspect, said method comprising contacting a cell, a tissue, or a tissue sample with said scaffold, measuring the emitted fluorescence and phosphorescence spectra and determining the oxygen levels.

In one embodiment, a scaffold of the invention can be placed in a subject at the site of a tissue transplant or of a tissue to be monitored. In one aspect, cells or tissue are allowed to adhere to a scaffold of the invention prior to it being placed in a subject. In one aspect, the scaffold is implanted into a subject before said oxygen levels are determined. In one aspect, when cells or tissue are allowed to adhere to a scaffold before it is implanted, the scaffold with the cells or tissue is allowed to adjust or acclimate before being implanted.

In one embodiment, the tissue to be monitored is selected from the group consisting of ischemic tissue, transplanted tissue, diseased tissue, and injured tissue. In one aspect, transplanted tissue is pancreatic islet tissue. In one aspect, oxygen levels are measured in the pancreatic islet tissue.

In one embodiment of the invention, the method provides for the detection of hypoxia in a tissue.

Oxygen levels can be measured once or more than once. The levels can be determined over a time course or used to monitor cells or a tissue over time, depending on what is being monitored.

The present invention provides in one aspect polymeric luminescent dye compounds having fluorescent properties, phosphorescent properties, or both fluorescent and phosphorescent properties. Accordingly, the invention provides compounds having formula I as found in U.S. Pat. No. 7,955,861:

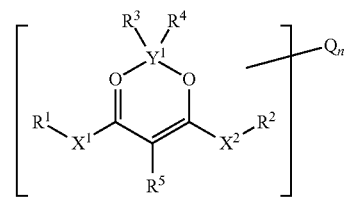

wherein $R^1$ and $R^2$ are independently $(C_6-C_{22})$aryl or $(C_5-C2_{21})$heteroaryl. The $R^1$ and $R^2$ groups are optionally independently substituted with 1, 2, 3, 4, 5, 6, 7, 8, 9, 10, 11, 12, 13, 14, or 15 substituent groups; where the substituent groups are halo, $(C_1-C_{12})$alkyl, hydroxy$(C_1-C_{12})$alkyl, halo$(C_1-C_{12})$alkyl, $R^{15}O(C_1-C_{12})$alkyl, $R^{15}O(C_1-C_{12})$alkyl-O—, $(C_2-C_{12})$alkenyl, $(C_7-C_{26})$aralkyl, $(C_5-C_{13})$heteroaryl, —$OR^{15}$, oxo (>C=O), —CN, —$NO_2$, —$CO_2R^{15}$, —OC(O)$R^{16}$, —C(O)$R^{16}$, —$NR^{13}R^{14}$, —N($R^{23}$)C(O)$R^{24}$, —C(O)$NR^{17}R^{18}$, —$SR^{19}$, —$SO_2R^{20}$; —$OSiR^{25}_3$, —$SiR^{25}_3$—$SiR^{25}_i(OR^{25})_j$, —P($OR^{25}$)$_3$, —$PR^{25}_3$, isocyanate, isothiocyanate, urea, or thiourea; or two substituent groups can form a ring together with the atom to which they are attached optionally having from 3 to 8 ring atoms and optionally having 1, 2, or 3 heteroatoms; each $R^{25}$ is independently hydrogen, alkyl or aryl; and the sum of i and j is 3;

$Y^1$ is Al or B; $X^1$ and $X^2$ are independently a bond, alkyl, alkenyl, alkynyl or aryl, optionally substituted with 1, 2, 3, 4, 5, or 6 substituent groups; where the substituent groups are halo, $(C_1-C_{12})$alkyl, hydroxy$(C_1-C_{12})$alkyl, halo$(C_1-C_{12})$alkyl, $R^{15}O(C_1-C_{12})$alkyl, $R^{15}O(C_1-C_{12})$alkyl-O—, $(C_2-C_{12})$alkenyl, $(C_7-C_{26})$aralkyl, $(C_5-C_{13})$-heteroaryl, —$OR^{15}$, oxo (>C=O), —CN, —$NO_2$, —$CO_2$ $R^{15}$, —OC(O)$R^{16}$, —C(O)$R^{16}$, $NR^{13}R^{14}$, —N($R^{23}$)C(O)$R^{24}$, —C(O)$NR^{17}R^{18}$, —$SR^{19}$, —$SO_2R^{20}$, —$OSiR_3$, —$SiR_3$, —$SiR^{25}_i(OR^{25})_j$—, —$PR_3$, —P(OR)$_3$, isocyanate, isothiocyanate, urea, thiourea or two substituent groups can form a ring together with the atom to which they are attached optionally having from 3 to 8 ring atoms and optionally having 1, 2, or 3 heteroatoms; $R^3$ and $R^4$ are independently, halo, hydroxy, $R^{15}O(C_1-C_{12})$alkyl, $R^{15}O(C_1-C_{12})$alkyl, or —$OR^{15}$; or $R^3$ and $R^4$ taken together form a bidentate chelate, such as deprotonated acid or diacid group, HOC(=O)$CH_2$C(=O)OH (malonic acid) or HOC(=O)$CH_2$C(=O)OH (oxalic acid), or chelating group such as acid-alcohol, acid-ether, with two donor groups, or $R^3$ and $R^4$ taken together with the boron atom form a ring having the formula:

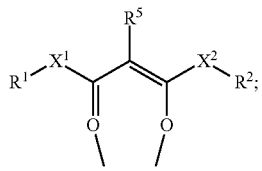

$R^5$ is hydrogen, halo, $(C_1-C_{12})$alkyl, hydroxy$(C_1-C_{12})$alkyl, halo$(C_1-C_{12})$alkyl, $(C_2-C_{12})$alkenyl, $(C_7-C_{26})$aralkyl, $(C_5-C_{13})$heteroaryl, —$OR^{15}$, —CN, —$NO_2$, —$CO_2$ $R^{15}$, —OC(O)$R^{16}$, —C(O)$R^{16}$, —$NR^{13}R^{14}$, —N($R^{23}$)C(O)$R^{24}$, —C(O)$NR^{17}$ $R^{18}$, —$SR^{19}$, —$SO_2R^{20}$ or —$SO_3H$; or wherein $R^{13}$, $R^{14}$, $R^{15}$, $R^{16}$, $R^{17}$, $R^{18}$, $R^{19}$, $R^{20}$, $R^{23}$ and $R^{24}$ are independently hydrogen, alkyl, alkenyl, $(C_3-C_{12})$cycloalkyl, aryl, aralkyl or haloalkyl; each Q is a polymer chain where each chain is conjugated directly to the compound (e.g., via a covalent, coordinate, ionic, or hydrogen bond) through one of $R^1$, $R^2$, $R^5$, $X^1$, $X^2$ or to a substituent attached to $R^1$, $R^2$, $R^5$, $X^1$, or $X^2$; and n is 1, 2, 3, 4, 5, 6, 7, 8, 9, 11, 12, 13, 14, or 15; or a pharmaceutically acceptable salt thereof.

One boron dye compound conjugated to a polymer is BF2dbm(I)PLA as described in Zhang et al., 2009, Nature Materials.

An active dye of the invention without the Iodine is:

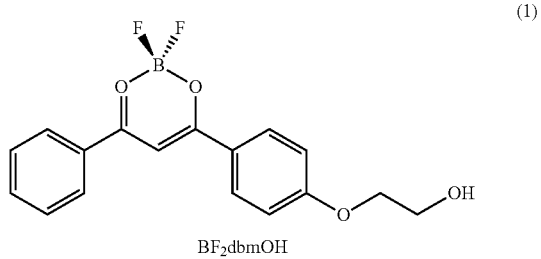

BF₂dbmOH (1)

Boron or aluminum substituted compounds (e.g., boron difluoride) can be bound to functionalized diketones (e.g., dibenzoylmethane) and used as initiators for polymerization of lactide and other monomers. Luminescent dye groups are introduced in the polymeric material (e.g., biodegradable and biocompatible polylactide) on specific sites in the polymer architecture with control. Block copolymers capable of nanoscale self assembly are possible. The compounds and compositions of the invention are useful as imaging agents, probes, readily processable photosensitizers, sensors (e.g., oxygen, ratiometric, both intensity and lifetime based; temperature; moisture; pH), laser dyes, optical fibers, waveguides, light emitting materials for displays, biocompatible polymers, solvatochromic materials, lithographic materials, photodegradable materials, photoactivated oxidizing agents, colorants, inks, reactive dyes, and the like. The photosensitizers can be used to produce a beneficial effect in photodynamic therapy for treatment of tumors.

In addition, where features or aspects of the invention are described in terms of Markush groups, those skilled in the art will recognize that the invention is also thereby described in terms of any individual member or subgroup of members of the Markush group. For example, if X is described as selected from the group consisting of bromine, chlorine, and iodine, claims for X being bromine and claims for X being bromine and chlorine are fully described. Moreover, where features or aspects of the invention are described in terms of Markush groups, those skilled in the art will recognize that the invention is also thereby described in terms of any combination of individual members or subgroups of members of Markush groups. Thus, for example, if X is described as selected from the group consisting of bromine, chlorine, and iodine, and Y is described as selected from the group consisting of methyl, ethyl, and propyl, claims for X being bromine and Y being methyl are fully described.

If a value of a variable that is necessarily an integer, e.g., the number of carbon atoms in an alkyl group or the number of substituents on a ring, is described as a range, e.g., 0-4, what is meant is that the value can be any integer between 0 and 4 inclusive, i.e., 0, 1, 2, 3, or 4.

In various embodiments, the compound or set of compounds, such as are used in the inventive methods, can be any one of any of the combinations and/or sub-combinations of the above-listed embodiments.

In various embodiments, a compound as shown in any of the Examples, or among the exemplary compounds, is provided. Provisos may apply to any of the disclosed categories or embodiments wherein any one or more of the other above disclosed embodiments or species may be excluded from such categories or embodiments.

The present invention further embraces isolated compounds according to formula (I). The expression "isolated compound" refers to a preparation of a compound of formula (I), or a mixture of compounds according to formula (I), wherein the isolated compound has been separated from the reagents used, and/or byproducts formed, in the synthesis of the compound or compounds. "Isolated" does not mean that the preparation is technically pure (homogeneous), but it is sufficiently pure to compound in a form in which it can be used therapeutically. Preferably an "isolated compound" refers to a preparation of a compound of formula (I) or a mixture of compounds according to formula (I), which contains the named compound or mixture of compounds according to formula (I) in an amount of at least 10 percent by weight of the total weight.

The compounds of the invention and intermediates may be isolated from their reaction mixtures and purified by standard techniques such as filtration, liquid-liquid extraction, solid phase extraction, distillation, recrystallization or chromatography, including flash column chromatography, or HPLC.

In general, "substituted" refers to an organic group as defined herein in which one or more bonds to a hydrogen atom contained therein are replaced by one or more bonds to a non-hydrogen atom such as, but not limited to, a halogen (i.e., F, Cl, Br, and I); an oxygen atom in groups such as hydroxyl groups, alkoxy groups, aryloxy groups, aralkyloxy groups, oxo(carbonyl) groups, carboxyl groups including carboxylic acids, carboxylates, and carboxylate esters; a sulfur atom in groups such as thiol groups, alkyl and aryl sulfide groups, sulfoxide groups, sulfone groups, sulfonyl groups, and sulfonamide groups; a nitrogen atom in groups such as amines, hydroxylamines, nitriles, nitro groups, N-oxides, hydrazides, azides, and enamines; and other heteroatoms in various other groups. Non-limiting examples of substituents J that can be bonded to a substituted carbon (or other) atom include F, Cl, Br, I, OR', OC(O)N(R')₂, CN, NO, NO₂, ONO₂, azido, CF₃, OCF₃, R', O (oxo), S (thiono), C(O), S(O), methylenedioxy, ethylenedioxy, N(R')₂, SR', SOR', SO₂R', SO₂N(R')₂, SO₃R', C(O)R', C(O)C(O)R', C(O)CH₂C(O)R', C(S)R', C(O)OR', OC(O)R', C(O)N(R')₂, OC(O)N(R')₂, C(S)N(R')₂, (CH₂)₀₋₂N(R')C(O)R', (CH₂)₀₋₂N(R')N(R')₂, N(R')N(R')C(O)R', N(R')N(R')C(O)OR', N(R')N(R')CON(R')₂, N(R')SO₂R', N(R')SO₂N(R')₂, N(R')C(O)OR', N(R')C(O)R', N(R')C(S)R', N(R')C(O)N(R')₂, N(R')C(S)N(R')₂, N(COR')COR', N(OR')R', C(=NH)N(R')₂, C(O)N(OR')R', or C(=NOR')R' wherein R' can be hydrogen or a carbon-based moiety, and wherein the carbon-based moiety can itself be further substituted; for example, wherein R' can be hydrogen, alkyl, cycloalkyl, aryl, aralkyl, heterocyclyl, heteroaryl, or heteroarylalkyl, wherein any alkyl, cycloalkyl, aryl, aralkyl, heterocyclyl, heteroaryl, or heteroarylalkyl or R' can be independently mono- or multi-substituted with J; or wherein two R' groups bonded to a nitrogen atom or to adjacent nitrogen atoms can together with the nitrogen atom or atoms form a heterocyclyl, which can be mono- or independently multi-substituted with J.

When a substituent is monovalent, such as, for example, F or Cl, it is bonded to the atom it is substituting by a single bond. When a substituent is more than monovalent, such as O, which is divalent, it can be bonded to the atom it is substituting by more than one bond, i.e., a divalent substituent is bonded by a double bond; for example, a C substituted with O forms a carbonyl group, C=O, which can also be written as "CO", "C(O)", or "C(=O)", wherein the C and the O are double bonded. When a carbon atom is substituted with a double-bonded oxygen (=O) group, the oxygen substituent is termed an "oxo" group. When a divalent substituent such as NR is double-bonded to a carbon atom, the resulting C(=NR) group is termed an "imino" group. When a divalent substituent such as S is double-bonded to a carbon atom, the results C(=S) group is termed a "thiocarbonyl" group.

Alternatively, a divalent substituent such as O, S, C(O), S(O), or S(O)$_2$ can be connected by two single bonds to two different carbon atoms. For example, O, a divalent substituent, can be bonded to each of two adjacent carbon atoms to provide an epoxide group, or the O can form a bridging ether group, termed an "oxy" group, between adjacent or non-adjacent carbon atoms, for example bridging the 1,4-carbons of a cyclohexyl group to form a [2.2.1]-oxabicyclo system. Further, any substituent can be bonded to a carbon or other atom by a linker, such as (CH$_2$)$_n$ or (CR'$_2$)$_n$ wherein n is 1, 2, 3, or more, and each R' is independently selected.

C(O) and S(O)$_2$ groups can also be bound to one or two heteroatoms, such as nitrogen or oxygen, rather than to a carbon atom. For example, when a C(O) group is bound to one carbon and one nitrogen atom, the resulting group is called an "amide" or "carboxamide." When a C(O) group is bound to two nitrogen atoms, the functional group is termed a "urea." When a C(O) is bonded to one oxygen and one nitrogen atom, the resulting group is termed a "carbamate" or "urethane." When a S(O)$_2$ group is bound to one carbon and one nitrogen atom, the resulting unit is termed a "sulfonamide." When a S(O)$_2$ group is bound to two nitrogen atoms, the resulting unit is termed a "sulfamate."

Substituted alkyl, alkenyl, alkynyl, cycloalkyl, and cycloalkenyl groups as well as other substituted groups also include groups in which one or more bonds to a hydrogen atom are replaced by one or more bonds, including double or triple bonds, to a carbon atom, or to a heteroatom such as, but not limited to, oxygen in carbonyl (oxo), carboxyl, ester, amide, imide, urethane, and urea groups; and nitrogen in imines, hydroxyimines, oximes, hydrazones, amidines, guanidines, and nitriles.

Substituted ring groups such as substituted cycloalkyl, aryl, heterocyclyl and heteroaryl groups also include rings and fused ring systems in which a bond to a hydrogen atom is replaced with a bond to a carbon atom. Therefore, substituted cycloalkyl, aryl, heterocyclyl and heteroaryl groups can also be substituted with alkyl, alkenyl, and alkynyl groups as defined herein.

By a "ring system" as the term is used herein is meant a moiety comprising one, two, three or more rings, which can be substituted with non-ring groups or with other ring systems, or both, which can be fully saturated, partially unsaturated, fully unsaturated, or aromatic, and when the ring system includes more than a single ring, the rings can be fused, bridging, or spirocyclic. By "spirocyclic" is meant the class of structures wherein two rings are fused at a single tetrahedral carbon atom, as is well known in the art.

As to any of the groups described herein, which contain one or more substituents, it is understood, of course, that such groups do not contain any substitution or substitution patterns which are sterically impractical and/or synthetically non-feasible. In addition, the compounds of this disclosed subject matter include all stereochemical isomers arising from the substitution of these compounds.

Selected substituents within the compounds described herein are present to a recursive degree. In this context, "recursive substituent" means that a substituent may recite another instance of itself or of another substituent that itself recites the first substituent. Because of the recursive nature of such substituents, theoretically, a large number may be present in any given claim. One of ordinary skill in the art of medicinal chemistry and organic chemistry understands that the total number of such substituents is reasonably limited by the desired properties of the compound intended. Such properties include, by way of example and not limitation, physical properties such as molecular weight, solubility or log P, application properties such as activity against the intended target, and practical properties such as ease of synthesis.

Recursive substituents are an intended aspect of the disclosed subject matter. One of ordinary skill in the art of medicinal and organic chemistry understands the versatility of such substituents. To the degree that recursive substituents are present in a claim of the disclosed subject matter, the total number should be determined as set forth above.

Alkyl groups include straight chain and branched alkyl groups and cycloalkyl groups having from 1 to about 20 carbon atoms, and typically from 1 to 12 carbons or, in some embodiments, from 1 to 8 carbon atoms. Examples of straight chain alkyl groups include those with from 1 to 8 carbon atoms such as methyl, ethyl, n-propyl, n-butyl, n-pentyl, n-hexyl, n-heptyl, and n-octyl groups. Examples of branched alkyl groups include, but are not limited to, isopropyl, iso-butyl, sec-butyl, t-butyl, neopentyl, isopentyl, and 2,2-dimethylpropyl groups. As used herein, the term "alkyl" encompasses n-alkyl, isoalkyl, and anteisoalkyl groups as well as other branched chain forms of alkyl. Representative substituted alkyl groups can be substituted one or more times with any of the groups listed above, for example, amino, hydroxy, cyano, carboxy, nitro, thio, alkoxy, and halogen groups.

Cycloalkyl groups are cyclic alkyl groups such as, but not limited to, cyclopropyl, cyclobutyl, cyclopentyl, cyclohexyl, cycloheptyl, and cyclooctyl groups. In some embodiments, the cycloalkyl group can have 3 to about 8-12 ring members, whereas in other embodiments the number of ring carbon atoms range from 3 to 4, 5, 6, or 7. Cycloalkyl groups further include polycyclic cycloalkyl groups such as, but not limited to, norbornyl, adamantyl, bornyl, camphenyl, isocamphenyl, and carenyl groups, and fused rings such as, but not limited to, decalinyl, and the like. Cycloalkyl groups also include rings that are substituted with straight or branched chain alkyl groups as defined above. Representative substituted cycloalkyl groups can be mono-substituted or substituted more than once, such as, but not limited to, 2,2-, 2,3-, 2,4-2,5- or 2,6-disubstituted cyclohexyl groups or mono-, di- or tri-substituted norbornyl or cycloheptyl groups, which can be substituted with, for example, amino, hydroxy, cyano, carboxy, nitro, thio, alkoxy, and halogen groups. The term "cycloalkenyl" alone or in combination denotes a cyclic alkenyl group.

The terms "carbocyclic," "carbocyclyl," and "carbocycle" denote a ring structure wherein the atoms of the ring are carbon, such as a cycloalkyl group or an aryl group. In some embodiments, the carbocycle has 3 to 8 ring members, whereas in other embodiments the number of ring carbon atoms is 4, 5, 6, or 7. Unless specifically indicated to the contrary, the carbocyclic ring can be substituted with as many as N−1 substituents wherein N is the size of the carbocyclic ring with, for example, alkyl, alkenyl, alkynyl, amino, aryl, hydroxy, cyano, carboxy, heteroaryl, heterocyclyl, nitro, thio, alkoxy, and halogen groups, or other groups as are listed above. A carbocyclyl ring can be a cycloalkyl ring, a cycloalkenyl ring, or an aryl ring. A carbocyclyl can be monocyclic or polycyclic, and if polycyclic each ring can be independently be a cycloalkyl ring, a cycloalkenyl ring, or an aryl ring.

(Cycloalkyl)alkyl groups, also denoted cycloalkylalkyl, are alkyl groups as defined above in which a hydrogen or carbon bond of the alkyl group is replaced with a bond to a cycloalkyl group as defined above.

Alkenyl groups include straight and branched chain and cyclic alkyl groups as defined above, except that at least one double bond exists between two carbon atoms. Thus, alkenyl groups have from 2 to about 20 carbon atoms, and typically from 2 to 12 carbons or, in some embodiments, from 2 to 8 carbon atoms. Examples include, but are not limited to vinyl, —CH═CH(CH$_3$), —CH═C(CH$_3$)$_2$, —C(CH$_3$)═CH$_2$, —C(CH$_3$)═CH(CH$_3$), —C(CH$_2$CH$_3$)═CH$_2$, cyclohexenyl, cyclopentenyl, cyclohexadienyl, butadienyl, pentadienyl, and hexadienyl among others.

Cycloalkenyl groups include cycloalkyl groups having at least one double bond between 2 carbons. Thus for example, cycloalkenyl groups include but are not limited to cyclohexenyl, cyclopentenyl, and cyclohexadienyl groups. Cycloalkenyl groups can have from 3 to about 8-12 ring members, whereas in other embodiments the number of ring carbon atoms range from 3 to 5, 6, or 7. Cycloalkyl groups further include polycyclic cycloalkyl groups such as, but not limited to, norbornyl, adamantyl, bornyl, camphenyl, isocamphenyl, and carenyl groups, and fused rings such as, but not limited to, decalinyl, and the like, provided they include at least one double bond within a ring. Cycloalkenyl groups also include rings that are substituted with straight or branched chain alkyl groups as defined above.

(Cycloalkenyl)alkyl groups are alkyl groups as defined above in which a hydrogen or carbon bond of the alkyl group is replaced with a bond to a cycloalkenyl group as defined above.

Alkynyl groups include straight and branched chain alkyl groups, except that at least one triple bond exists between two carbon atoms. Thus, alkynyl groups have from 2 to about 20 carbon atoms, and typically from 2 to 12 carbons or, in some embodiments, from 2 to 8 carbon atoms. Examples include, but are not limited to —C≡CH, —C≡C(CH$_3$), —C≡C(CH$_2$CH$_3$), —CH$_2$C≡CH, —CH$_2$C≡C(CH$_3$), and —CH$_2$C≡C(CH$_2$CH$_3$) among others.

The term "heteroalkyl" by itself or in combination with another term means, unless otherwise stated, a stable straight or branched chain alkyl group consisting of the stated number of carbon atoms and one or two heteroatoms selected from the group consisting of O, N, and S, and wherein the nitrogen and sulfur atoms may be optionally oxidized and the nitrogen heteroatom may be optionally quaternized. The heteroatom(s) may be placed at any position of the heteroalkyl group, including between the rest of the heteroalkyl group and the fragment to which it is attached, as well as attached to the most distal carbon atom in the heteroalkyl group. Examples include: —O—CH$_2$—CH$_2$—CH$_3$, —CH$_2$—CH$_2$CH$_2$—OH, —CH$_2$—CH$_2$—NH—CH$_3$, —CH$_2$—S—CH$_2$—CH$_3$, —CH$_2$CH$_2$—S(═O)—CH$_3$, and —CH$_2$CH$_2$—O—CH$_2$CH$_2$—O—CH$_3$. Up to two heteroatoms may be consecutive, such as, for example, —CH$_2$—NH—OCH$_3$, or —CH$_2$—CH$_2$—S—S—CH$_3$. A "cycloheteroalkyl" ring is a cycloalkyl ring containing at least one heteroatom. A cycloheteroalkyl ring can also be termed a "heterocyclyl," described below.

The term "heteroalkenyl" by itself or in combination with another term means, unless otherwise stated, a stable straight or branched chain monounsaturated or di-unsaturated hydrocarbon group consisting of the stated number of carbon atoms and one or two heteroatoms selected from the group consisting of O, N, and S, and wherein the nitrogen and sulfur atoms may optionally be oxidized and the nitrogen heteroatom may optionally be quaternized. Up to two heteroatoms may be placed consecutively. Examples include: —CH═CH—O—CH$_3$, —CH═CH—CH$_2$—OH, —CH$_2$—CH═N—OCH$_3$, —CH═CH—N(CH$_3$)—CH$_3$, —CH$_2$—CH═CH—CH$_2$—SH, and —CH═CH—O—CH$_2$CH$_2$—O—CH$_3$.

Aryl groups are cyclic aromatic hydrocarbons that do not contain heteroatoms in the ring. Thus aryl groups include, but are not limited to, phenyl, azulenyl, heptalenyl, biphenyl, indacenyl, fluorenyl, phenanthrenyl, triphenylenyl, pyrenyl, naphthacenyl, chrysenyl, biphenylenyl, anthracenyl, and naphthyl groups. In some embodiments, aryl groups contain about 6 to about 14 carbons in the ring portions of the groups. Aryl groups can be unsubstituted or substituted, as defined above. Representative substituted aryl groups can be mono-substituted or substituted more than once, such as, but not limited to, 2-, 3-, 4-, 5-, or 6-substituted phenyl or 2-8 substituted naphthyl groups, which can be substituted with carbon or non-carbon groups such as those listed above.

Aralkyl groups are alkyl groups as defined above in which a hydrogen or carbon bond of an alkyl group is replaced with a bond to an aryl group as defined above. Representative aralkyl groups include benzyl and phenylethyl groups and fused (cycloalkylaryl)alkyl groups such as 4-ethyl-indanyl. Aralkenyl group are alkenyl groups as defined above in which a hydrogen or carbon bond of an alkyl group is replaced with a bond to an aryl group as defined above.

Heterocyclyl groups or the term "heterocyclyl" includes aromatic and non-aromatic ring compounds containing 3 or more ring members, of which, one or more is a heteroatom such as, but not limited to, N, O, and S. Thus a heterocyclyl can be a cycloheteroalkyl, or a heteroaryl, or if polycyclic, any combination thereof. In some embodiments, heterocyclyl groups include 3 to about 20 ring members, whereas other such groups have 3 to about 15 ring members. A heterocyclyl group designated as a C$_2$-heterocyclyl can be a 5-ring with two carbon atoms and three heteroatoms, a 6-ring with two carbon atoms and four heteroatoms and so forth. Likewise a C$_4$-heterocyclyl can be a 5-ring with one heteroatom, a 6-ring with two heteroatoms, and so forth. The number of carbon atoms plus the number of heteroatoms sums up to equal the total number of ring atoms. A heterocyclyl ring can also include one or more double bonds. A heteroaryl ring is an embodiment of a heterocyclyl group. The phrase "heterocyclyl group" includes fused ring species including those comprising fused aromatic and non-aromatic groups. For example, a dioxolanyl ring and a benzdioxolanyl ring system (methylenedioxyphenyl ring system) are both heterocyclyl groups within the meaning herein. The phrase also includes polycyclic ring systems containing a heteroatom such as, but not limited to, quinuclidyl. Heterocyclyl groups can be unsubstituted, or can be substituted as discussed above. Heterocyclyl groups include, but are not limited to, pyrrolidinyl, piperidinyl, piperazinyl, morpholinyl, pyrrolyl, pyrazolyl, triazolyl, tetrazolyl, oxazolyl, isoxazolyl, thiazolyl, pyridinyl, thiophenyl, benzothiophenyl, benzofuranyl, dihydrobenzofuranyl, indolyl, dihydroindolyl, azaindolyl, indazolyl, benzimidazolyl, azabenzimidazolyl, benzoxazolyl, benzothiazolyl, benzothiadiazolyl, imidazopyridinyl, isoxazolopyridinyl, thianaphthalenyl, purinyl, xanthinyl, adeninyl, guaninyl, quinolinyl, isoquinolinyl, tetrahydroquinolinyl, quinoxalinyl, and quinazolinyl groups. Representative substituted heterocyclyl groups can be mono-substituted or substituted more than once, such as, but not limited to, piperidinyl or quinolinyl groups, which are 2-, 3-, 4-, 5-, or 6-substituted, or disubstituted with groups such as those listed above.

Heteroaryl groups are aromatic ring compounds containing 5 or more ring members, of which, one or more is a heteroatom such as, but not limited to, N, O, and S; for instance, heteroaryl rings can have 5 to about 8-12 ring members. A heteroaryl group is a variety of a heterocyclyl group that possesses an aromatic electronic structure. A heteroaryl group designated as a $C_2$-heteroaryl can be a 5-ring with two carbon atoms and three heteroatoms, a 6-ring with two carbon atoms and four heteroatoms and so forth. Likewise a $C_4$-heteroaryl can be a 5-ring with one heteroatom, a 6-ring with two heteroatoms, and so forth. The number of carbon atoms plus the number of heteroatoms sums up to equal the total number of ring atoms.

Heteroaryl groups include, but are not limited to, groups such as pyrrolyl, pyrazolyl, triazolyl, tetrazolyl, oxazolyl, isoxazolyl, thiazolyl, pyridinyl, thiophenyl, benzothiophenyl, benzofuranyl, indolyl, azaindolyl, indazolyl, benzimidazolyl, azabenzimidazolyl, benzoxazolyl, benzothiazolyl, benzothiadiazolyl, imidazopyridinyl, isoxazolopyridinyl, thianaphthalenyl, purinyl, xanthinyl, adeninyl, guaninyl, quinolinyl, isoquinolinyl, tetrahydroquinolinyl, quinoxalinyl, and quinazolinyl groups. Heteroaryl groups can be unsubstituted, or can be substituted with groups as is discussed above. Representative substituted heteroaryl groups can be substituted one or more times with groups such as those listed above.

Additional examples of aryl and heteroaryl groups include but are not limited to phenyl, biphenyl, indenyl, naphthyl (1-naphthyl, 2-naphthyl), N-hydroxytetrazolyl, N-hydroxytriazolyl, N-hydroxyimidazolyl, anthracenyl (1-anthracenyl, 2-anthracenyl, 3-anthracenyl), thiophenyl (2-thienyl, 3-thienyl), furyl (2-furyl, 3-furyl), indolyl, oxadiazolyl, isoxazolyl, quinazolinyl, fluorenyl, xanthenyl, isoindanyl, benzhydryl, acridinyl, thiazolyl, pyrrolyl (2-pyrrolyl), pyrazolyl (3-pyrazolyl), imidazolyl (1-imidazolyl, 2-imidazolyl, 4-imidazolyl, 5-imidazolyl), triazolyl (1,2,3-triazol-1-yl, 1,2,3-triazol-2-yl 1,2,3-triazol-4-yl, 1,2,4-triazol-3-yl), oxazolyl (2-oxazolyl, 4-oxazolyl, 5-oxazolyl), thiazolyl (2-thiazolyl, 4-thiazolyl, 5-thiazolyl), pyridyl (2-pyridyl, 3-pyridyl, 4-pyridyl), pyrimidinyl (2-pyrimidinyl, 4-pyrimidinyl, 5-pyrimidinyl, 6-pyrimidinyl), pyrazinyl, pyridazinyl (3-pyridazinyl, 4-pyridazinyl, 5-pyridazinyl), quinolyl (2-quinolyl, 3-quinolyl, 4-quinolyl, 5-quinolyl, 6-quinolyl, 7-quinolyl, 8-quinolyl), isoquinolyl (1-isoquinolyl, 3-isoquinolyl, 4-isoquinolyl, 5-isoquinolyl, 6-isoquinolyl, 7-isoquinolyl, 8-isoquinolyl), benzo[b]furanyl (2-benzo[b]furanyl, 3-benzo[b]furanyl, 4-benzo[b]furanyl, 5-benzo[b]furanyl, 6-benzo[b]furanyl, 7-benzo[b]furanyl), 2,3-dihydro-benzo[b]furanyl (2-(2,3-dihydro-benzo[b]furanyl), 3-(2,3-dihydro-benzo[b]furanyl), 4-(2,3-dihydro-benzo[b]furanyl), 5-(2,3-dihydro-benzo[b]furanyl), 6-(2,3-dihydro-benzo[b]furanyl), 7-(2,3-dihydro-benzo[b]furanyl), benzo[b]thiophenyl (2-benzo[b]thiophenyl, 3-benzo[b]thiophenyl, 4-benzo[b]thiophenyl, 5-benzo[b]thiophenyl, 6-benzo[b]thiophenyl, 7-benzo[b]thiophenyl), 2,3-dihydro-benzo[b]thiophenyl, (2-(2,3-dihydro-benzo[b]thiophenyl), 3-(2,3-dihydro-benzo[b]thiophenyl), 4-(2,3-dihydro-benzo[b]thiophenyl), 5-(2,3-dihydro-benzo[b]thiophenyl), 6-(2,3-dihydro-benzo[b]thiophenyl), 7-(2,3-dihydro-benzo[b]thiophenyl), indolyl (1-indolyl, 2-indolyl, 3-indolyl, 4-indolyl, 5-indolyl, 6-indolyl, 7-indolyl), indazole (1-indazolyl, 3-indazolyl, 4-indazolyl, 5-indazolyl, 6-indazolyl, 7-indazolyl), benzimidazolyl (1-benzimidazolyl, 2-benzimidazolyl, 4-benzimidazolyl, 5-benzimidazolyl, 6-benzimidazolyl, 7-benzimidazolyl, 8-benzimidazolyl), benzoxazolyl (1-benzoxazolyl, 2-benzoxazolyl), benzothiazolyl (1-benzothiazolyl, 2-benzothiazolyl, 4-benzothiazolyl, 5-benzothiazolyl, 6-benzothiazolyl, 7-benzothiazolyl), carbazolyl (1-carbazolyl, 2-carbazolyl, 3-carbazolyl, 4-carbazolyl), 5H-dibenz[b,f]azepine (5H-dibenz[b,f]azepin-1-yl, 5H-dibenz[b,f]azepine-2-yl, 5H-dibenz[b,f]azepine-3-yl, 5H-dibenz[b,f]azepine-4-yl, 5H-dibenz[b,f]azepine-5-yl), 10,11-dihydro-5H-dibenz[b,f]azepine (10,11-dihydro-5H-dibenz[b,f]azepine-1-yl, 10,11-dihydro-5H-dibenz[b,f]azepine-2-yl, 10,11-dihydro-5H-dibenz[b,f]azepine-3-yl, 10,11-dihydro-5H-dibenz[b,f]azepine-4-yl, 10,11-dihydro-5H-dibenz[b,f]azepine-5-yl), and the like.

Heterocyclylalkyl groups are alkyl groups as defined above in which a hydrogen or carbon bond of an alkyl group as defined above is replaced with a bond to a heterocyclyl group as defined above. Representative heterocyclyl alkyl groups include, but are not limited to, furan-2-yl methyl, furan-3-yl methyl, pyridine-3-yl methyl, tetrahydrofuran-2-yl ethyl, and indol-2-yl propyl.

Heteroarylalkyl groups are alkyl groups as defined above in which a hydrogen or carbon bond of an alkyl group is replaced with a bond to a heteroaryl group as defined above.

The term "alkoxy" refers to an oxygen atom connected to an alkyl group, including a cycloalkyl group, as are defined above. Examples of linear alkoxy groups include but are not limited to methoxy, ethoxy, propoxy, butoxy, pentyloxy, hexyloxy, and the like. Examples of branched alkoxy include but are not limited to isopropoxy, sec-butoxy, tert-butoxy, isopentyloxy, isohexyloxy, and the like. Examples of cyclic alkoxy include but are not limited to cyclopropyloxy, cyclobutyloxy, cyclopentyloxy, cyclohexyloxy, and the like. An alkoxy group can include one to about 12-20 carbon atoms bonded to the oxygen atom, and can further include double or triple bonds, and can also include heteroatoms. For example, an allyloxy group is an alkoxy group within the meaning herein. A methoxyethoxy group is also an alkoxy group within the meaning herein, as is a methylenedioxy group in a context where two adjacent atoms of a structures are substituted therewith.

The terms "halo" or "halogen" or "halide" by themselves or as part of another substituent mean, unless otherwise stated, a fluorine, chlorine, bromine, or iodine atom, preferably, fluorine, chlorine, or bromine.

A "haloalkyl" group includes mono-halo alkyl groups, poly-halo alkyl groups wherein all halo atoms can be the same or different, and per-halo alkyl groups, wherein all hydrogen atoms are replaced by halogen atoms, such as fluoro. Examples of haloalkyl include trifluoromethyl, 1,1-dichloroethyl, 1,2-dichloroethyl, 1,3-dibromo-3,3-difluoropropyl, perfluorobutyl, and the like.

A "haloalkoxy" group includes mono-halo alkoxy groups, poly-halo alkoxy groups wherein all halo atoms can be the same or different, and per-halo alkoxy groups, wherein all hydrogen atoms are replaced by halogen atoms, such as fluoro. Examples of haloalkoxy include trifluoromethoxy, 1,1-dichloroethoxy, 1,2-dichloroethoxy, 1,3-dibromo-3,3-difluoropropoxy, perfluorobutoxy, and the like.

The term "$(C_x$-$C_y)$perfluoroalkyl," wherein x<y, means an alkyl group with a minimum of x carbon atoms and a maximum of y carbon atoms, wherein all hydrogen atoms are replaced by fluorine atoms. Preferred is —(C$_1$-C$_6$)perfluoroalkyl, more preferred is —(C$_1$-C$_3$)perfluoroalkyl, most preferred is —CF$_3$.

The term "(C$_x$-C$_y$)perfluoroalkylene," wherein x<y, means an alkyl group with a minimum of x carbon atoms and a maximum of y carbon atoms, wherein all hydrogen atoms are replaced by fluorine atoms. Preferred is —(C$_1$-C$_6$)perfluoroalkylene, more preferred is —(C$_1$-C$_3$)perfluoroalkylene, most preferred is —CF$_2$—.

The terms "aryloxy" and "arylalkoxy" refer to, respectively, an aryl group bonded to an oxygen atom and an aralkyl group bonded to the oxygen atom at the alkyl moiety. Examples include but are not limited to phenoxy, naphthyloxy, and benzyloxy.

An "acyl" group as the term is used herein refers to a group containing a carbonyl moiety wherein the group is bonded via the carbonyl carbon atom. The carbonyl carbon atom is also bonded to another carbon atom, which can be part of an alkyl, aryl, aralkyl cycloalkyl, cycloalkylalkyl, heterocyclyl, heterocyclylalkyl, heteroaryl, heteroarylalkyl group or the like. In the special case wherein the carbonyl carbon atom is bonded to a hydrogen, the group is a "formyl" group, an acyl group as the term is defined herein. An acyl group can include 0 to about 12-20 additional carbon atoms bonded to the carbonyl group. An acyl group can include double or triple bonds within the meaning herein. An acryloyl group is an example of an acyl group. An acyl group can also include heteroatoms within the meaning here. A nicotinoyl group (pyridyl-3-carbonyl) group is an example of an acyl group within the meaning herein. Other examples include acetyl, benzoyl, phenylacetyl, pyridylacetyl, cinnamoyl, and acryloyl groups and the like. When the group containing the carbon atom that is bonded to the carbonyl carbon atom contains a halogen, the group is termed a "haloacyl" group. An example is a trifluoroacetyl group.

The term "amine" includes primary, secondary, and tertiary amines having, e.g., the formula N(group)$_3$ wherein each group can independently be H or non-H, such as alkyl, aryl, and the like. Amines include but are not limited to R—NH$_2$, for example, alkylamines, arylamines, alkylarylamines; R$_2$NH wherein each R is independently selected, such as dialkylamines, diarylamines, aralkylamines, heterocyclylamines and the like; and R$_3$N wherein each R is independently selected, such as trialkylamines, dialkylarylamines, alkyldiarylamines, triarylamines, and the like. The term "amine" also includes ammonium ions as used herein.

Nanoparticles prepared from the disclosed luminescent dye polymers and compositions can be taken up and internalized by cells, which is useful for imaging. By a "ring system" as the term is used herein is meant a moiety comprising one, two, three or more rings, which can be substituted with non-ring groups or with other ring systems, or both, which can be fully saturated, partially unsaturated, fully unsaturated, or aromatic, and when the ring system includes more than a single ring, the rings can be fused, bridging, or spirocyclic. By "spirocyclic" is meant the class of structures wherein two rings are fused at a single tetrahedral carbon atom, as is well known in the art.

As to any of the groups described herein, which contain one or more substituents, it is understood, of course, that such groups do not contain any substitution or substitution patterns which are sterically impractical and/or synthetically non-feasible. In addition, the compounds of this disclosed subject matter include all stereochemical isomers arising from the substitution of these compounds.

Selected substituents within the compounds described herein are present to a recursive degree. In this context, "recursive substituent" means that a substituent may recite another instance of itself or of another substituent that itself recites the first substituent. Because of the recursive nature of such substituents, theoretically, a large number may be present in any given claim. One of ordinary skill in the art of medicinal chemistry and organic chemistry understands that the total number of such substituents is reasonably limited by the desired properties of the compound intended. Such properties include, by way of example and not limitation, physical properties such as molecular weight, solubility or log P, application properties such as activity against the intended target, and practical properties such as ease of synthesis.

Recursive substituents are an intended aspect of the disclosed subject matter. One of ordinary skill in the art of medicinal and organic chemistry understands the versatility of such substituents. To the degree that recursive substituents are present in a claim of the disclosed subject matter, the total number should be determined as set forth above.

The following definitions are used, unless otherwise described: halo includes fluoro, chloro, bromo, or iodo. Alkyl, alkoxy, alkenyl, alkynyl, etc. denote both straight and branched groups; but reference to an individual radical such as "propyl" embraces only the straight chain radical, a branched chain isomer such as "isopropyl" being specifically referred to. Aryl denotes a phenyl radical or an ortho-fused bicyclic carbocyclic radical having about nine to ten ring atoms in which at least one ring is aromatic. Heteroaryl encompasses a radical attached via a ring carbon of a monocyclic aromatic ring containing five or six ring atoms consisting of carbon and one to four heteroatoms. The heteroatoms include non-peroxide oxygen, sulfur, silane, nitrogen and phosphorous wherein suitable substituents as known in the art can be attached to the hetero atoms, e.g., hydrogen, O, (C$_1$-C$_{12}$)alkyl, phenyl or benzyl, as well as a radical of an ortho-fused bicyclic heterocycle of about eight to ten ring atoms derived therefrom, particularly a benz-derivative or one derived by fusing a propylene, trimethylene, or tetramethylene diradical thereto.

It will be appreciated by those skilled in the art that compounds of the invention having a chiral center may exist in and be isolated in optically active and racemic forms. Some compounds may exhibit polymorphism. It is to be understood that the present invention encompasses any racemic, optically-active, polymorphic, or stereoisomeric form, or mixtures thereof, of a compound of the invention, which possess the useful properties described herein, it being well known in the art how to prepare optically active forms (for example, by resolution of the racemic form by recrystallization techniques, by synthesis from optically-active starting materials, by chiral synthesis, or by chromatographic separation using a chiral stationary phase).

Specific and preferred values listed below for radicals, substituents, and ranges, are for illustration only. They do not exclude other defined values or other values within defined ranges for the radicals and substituents. Specifically, (C1-C12)alkyl can be methyl, ethyl, propyl, isopropyl, butyl, iso-butyl, sec-butyl, pentyl, 3-pentyl, hexyl and the like; (C3-C12)cycloalkyl can be cyclopropyl, cyclobutyl, cyclopentyl, or cyclohexyl and the like; (C3-C12)cycloalkyl (C1-C8)alkyl can be cyclopropylmethyl, cyclobutylmethyl, cyclopentylmethyl, cyclohexylmethyl, 2-cyclopropylethyl, 2-cyclobutylethyl, 2-cyclopentylethyl, or 2-cyclohexylethyl and the like; (C1-C10)alkoxy can be methoxy, ethoxy, propoxy, isopropoxy, butoxy, iso-butoxy, sec-butoxy, pentoxy, 3-pentoxy, or hexyloxy and the like; (C2-C12)alkenyl can be vinyl, allyl, 1-propenyl, 2-propenyl, 1-butenyl, 2-butenyl, 3-butenyl, 1,-pentenyl, 2-pentenyl, 3-pentenyl, 4-pentenyl, 1-hexenyl, 2-hexenyl, 3-hexenyl, 4-hexenyl, or 5-hexenyl and the like; (C2-C12)alkynyl can be ethynyl, 1-propynyl, 2-propynyl, 1-butynyl, 2-butynyl, 3-butynyl, 1-pentynyl, 2-pentynyl, 3-pentynyl, 4-pentynyl, 1-hexynyl, 2-hexynyl, 3-hexynyl, 4-hexynyl, or 5-hexynyl and the like; (C1-C12)alkanoyl can be acetyl, propanoyl or butanoyl and the like; halo(C1-C6)alkyl can be iodomethyl, bromomethyl, chloromethyl, fluoromethyl, trifluoromethyl, 2-chloroethyl, 2-fluoroethyl, 2,2,2-trifluoroethyl, or pentafluoroethyl and the like; hydroxy(C1-C12)alkyl can be hydroxymethyl, 1-hydroxyethyl, 2-hydroxyethyl, 1-hydroxypropyl, 2-hydroxypropyl, 3-hydroxypropyl, 1-hydroxybutyl, 4-hydroxybutyl, 1-hydroxypentyl, 5-hydroxypentyl, 1-hydroxyhexyl, or 6-hydroxyhexyl and the like; (C1 C12)alkoxycarbonyl can be methoxycarbonyl, ethoxycarbonyl, propoxycarbonyl, isopropoxycarbonyl, butoxycarbonyl, pentoxycarbonyl, or hexyloxycarbonyl and the like; (C1-C12)alkylthio can be methylthio, ethylthio, propylthio, isopropylthio, butylthio, isobutylthio, pentylthio, or hexylthio and the like; (C2-C12)alkanoyloxy can be acetoxy, propanoyloxy, butanoyloxy, isobutanoyloxy, pentanoyloxy, or hexanoyloxy and the like; (C6-C22)aryl can be phenyl, naphthyl, anthrcyl, phenanthryl, pyryl, naphthacyl, pentacyl, or indenyl and the like; and (C5-C13)¬heteroaryl can be furyl, imidazolyl, triazolyl, triazinyl, oxazoyl, isoxazoyl, thiazolyl, isothiazoyl, pyrazolyl, pyrrolyl, pyrazinyl, tetrazolyl, pyridyl, (or its N-oxide), thienyl, pyrimidinyl (or its N-oxide), indolyl, isoquinolyl (or its N-oxide) or quinolyl (or its N-oxide) and the like.

The polymers, Q, that are conjugated to the formula I compounds or blended with the formula II compounds include any polymeric material that can be conjugated or blended with a formula II compound. In one embodiment, non-toxic pharmaceutically acceptable, biologically stable (or biodegradable) polymers are preferred. Non-limiting examples of pharmaceutically acceptable polymers include polylactide (PLA), polyglycolide, lactide-glycolide copolymer, polycaprolactone, or polyethylene glycol polylactide polymers, polyhydroxybutyrate (PHB), poly-hydroxy-butyrate-valerate copolymer (PHBV), polybutylene succinate (PBS), polybutylene adipate-co-terephthalate (PBAT), sugar based polymers (e.g., cellulose or starch and the like), peptides, or mixtures thereof. Other exemplary polymers include polyurethanes, polyamides, polyesters, and vinylic polymers. Non-limiting examples of vinylic polymers include acrylates such as polymethyl methacrulate (PMMA), acrylonitrile butadiene styrene (ABS), styrene acrylonitrile (SAN), polystyrenes (PS), polyethylene (PE), polyethylenechlorinates (PEC), polybutadiene (PBD), polydicyclopentadiene (PDCP), polypropylene (PP) Polymethylpentene (PMP), and the like. Other exemplary polymers include silicon-based organic polymers such as polydimethylsiloxane (PDMS), polyesters such as polyethylene terephthalate (PET), glycolized polyester (PETG), polycarbonate (PC) and the like.

Additional exemplary polymers that can be prepared as Q groups or blended with the light emitting compounds include sol gels, aerogels, xerogels, cellulosic polymers, e.g., hydroxypropylmethylcellulose, hydroxyl propyl cellulose, ethyl cellulose and the like; epoxy containing polymers, Ethylene vinyl alcohol, (E/VAL), fluoroplastics, e.g., polytetrafluoroethylene (PTFE), liquid crystal polymers, (LCP), melamine formaldehyde, (MF), phenol-formaldehyde plastic (PF), polyacetal, polyacrylates, polymethacrylates, polyacrylonitrile, (PAN), polyamide, (PA), e.g., nylon, polyamide-imide (PAI), polyaryletherketone (PAEK), polyetheretherketone (PEEK), polyphenylene oxide (PPO), polyphenylene sulfide (PPS), polyphthalamide (PTA), Polysulfone (PSU), polyurethane (PU), polyurea, polyvinylchloride (PVC), polyvinylidene Chloride (PVDC), polyvinylidenedifluoride (PVDF) silicone polymers, poly(ethylene glycol) (PEG), poly(ethylene terephthalate) (PET), Polysiloxanes, silicones, In one embodiment, the composition includes pharmaceutically acceptable polymers, FDA approved polymers or a mixture thereof. In another embodiment, the compositions include polymers prepared from vinyl monomers known in the art. In another embodiment, the invention also provides pharmaceutical compositions comprising a compound of luminescent dye having formula II, or a pharmaceutically acceptable salt thereof, in combination with a pharmaceutically acceptable diluent or carrier.

The compounds having formula I can be conjugated to a polymer through any suitable functional linking group. For example the conjugate can include dye-X, dye-X—Y, dye-X—R—Y, where X and Y can be initiators, terminators or coupling partner with a complimentary reactive group on a polymer (e.g., at the chain end, main chain, side group, etc.). Alternatively, the diketone and the polymer may be linked to generate a "macroligand" (e.g., dbmPLA or dbmPMMA) which is subsequently reacted with a B or Al (e.g. Y1) precursor such as BF3 to generate the luminescent material (e.g., $BF_2$dbmPLA or $BF_2$dbmPMMA). A reactive group (initiator group) can be placed in a formula II compound using any means known in the art. The initiator groups can react with monomers, polymers, or oligomers to form at least one polymer chain. In some cases the initiator can be part of the R1, R2, R5, X1 or X2 and used for direct coupling, (e.g., initiation). Examples of initiator groups include primary alcohol linking group (e.g., a group having the formula —$(CH_2)$z-OH, where z is an integer from 1 to about 25; or —O—R6-O—H where R6 is alkylene, or alkenylene having at least two carbon atoms). Exemplary alcohol containing groups include hydroxymethyl, hydroxyethyl, hydroxypropyl, hydroxybutyl, —O—CH2CH2-OH or ArOH, and the like. Polymer groups prepared from vinyl groups can use a radical forming linking group (e.g., a diazo or peroxy group). Other exemplary initiator groups include thiocarbonylthio compounds, such as dithioesters, dithiocarbamates, trithiocarbonates, xanthates, and the like.

The polymer chains can be formed using any compatible polymer synthesis method known in the art such as; 1) Nitroxide-mediated polymerization (NMP); 2) Reversible addition-fragmentation chain transfer (RAFT) polymerization using compounds having thiocarbonylthio initiator groups, such as dithioesters, dithiocarbamates, trithiocarbonates, and xanthates; 3) ATRP: using compounds having activated RCH2X initiator groups where X is a halogen (e.g., chlorine or bromine), α-haloesters such as α-bromobutyrolactone, allyl chloroacetate, vinyl chloroacetate, hydroxyethyl 2-bromobutyrate, t-butyl 2-bromobutyrate, glycidol 2-bromopropionate, and the like or α-haloamides such as 2-chloroacetamide and the like. Ring opening polymerization methods can use also compounds having alcohols or metal alkoxide, and carboxylic acid or metal carboxylate as initiator groups. Cationic polymerization methods can uses compounds having alkyl halide, tosylate, Lewis acid or alcohol initiator groups. Anionic polymerization reactions can use compounds having alcoholic or nucleophilic base initiator groups, such initiators for anionic polymerization are known in the art.

The invention includes dimers, e.g., compounds where $R^3$ and $R^4$ taken together with the $Y^1$ atom form a chelate ring having the formula:

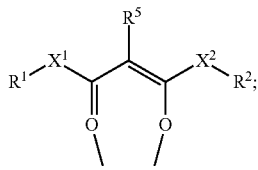

e.g., $R^3$ and $R^4$ form a ring together with the atom to which they are attached to provide a compound having formula III

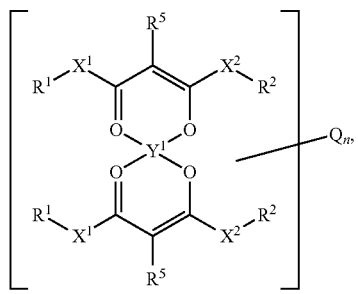

where each $R^1$, $R^2$, $X^1$, $X^2$ and $R^5$ are independently selected from the definitions above. Additionally, $R^3$ and $R^4$ taken together form a bidentate chelate, such as deprotonated acid or diacid group, HOC(=O)CH$_2$C(=O)OH (malonic acid) or HOC(=O)CH$_2$C(=O)OH (oxalic acid), or chelating group such as acid-alcohol, acid-ether, with two donor groups, or $R_3$ and $R_4$ taken together with the boron atom form a ring having the formula:

Preferred $R_1$ and $R_2$ groups include phenyl, naphthyl, anthracyl or have the formula

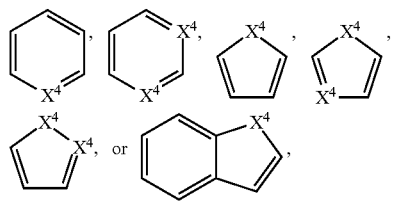

where each $X_4$ is independently O, S, $NR^a$, or $PR^a$, where $R^a$ is hydrogen, alkyl or aryl.

More preferred $R_1$ and $R_2$ groups include phenyl, naphthyl, anthracyl or have the formula:

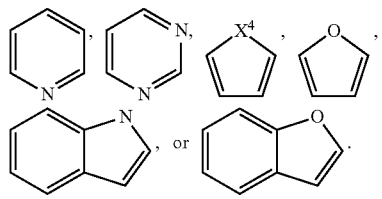

Even more preferred $R^1$ and $R^2$ groups include phenyl, or naphthyl.

Specific substituents include halo, hydroxy($C_1$-$C_{12}$)alkyl, halo($C_1$-$C_{12}$)alkyl, $R^{15}$O($C_1$-$C_{12}$)alkyl, $R^{15}$O($C_1$-$C_{12}$)alkyl-O—, —$OR^{15}$, —$CO_2R^{15}$, —$OC(O)R^{16}$, $C(O)R^{16}$, —$NR^{13}R^{14}$, —$N(R^{23})C(O)R^{24}$, —$C(O)NR^{17}R^{18}$, —$SR^{19}$, or —$SO_2R^{20}$.

Preferred $R_3$ and $R_4$ substituents include electron withdrawing groups such as halo, e.g., fluorine.

Preferred $R_3$ and $R_4$ substituents include electron donating group such as $OR^{15}$.

The polymeric luminescent dye compounds and compositions can be processed into materials that can be combined in medical devices such as oxygen sensors. The sensors can be used to detect low levels of oxygen in, e.g., blocked vasculature, hypoxic tumors.

Diketone synthesis is modular. Different $R^1$ and $R^2$ groups may be added to either side of the diketone to modulate optical properties (e.g., luminophores). Additionally, the $R^1$ and $R^2$ can contain a linker group (e.g. initiator, terminating agent, coupling partner) or a group that can be readily converted using standard chemical techniques to an initiator site. Various commercially available starting compounds that have initiator sites may be readily used or modified to form compounds having formula I. The compounds having formula II can be modified to tune polymer architecture, materials and optical properties. Block copolymers can be also prepared, by sequential monomer addition or by modifying dibenzoylmethane and related diketones with two different kinds of initiator sites. These can self assemble to generate nanostructured films, bulk materials, solution assemblies, particles, etc. Other polymer compositions can be also prepared, e.g., by varying the initiator group. A preferred initiator group for lactide or caprolactone ring opening polymerizations is a primary alcohol. Alpha bromoesters are good initiator groups for ATRP, affording PMMA and other polymers. The diketone ligand molecules can be readily prepared using standard methods known to a person skilled in organic synthesis. In addition many ligands are commercially available and have groups that can be used or transformed into initiator groups. Exemplary ligand molecules include molecules having the formulas below:

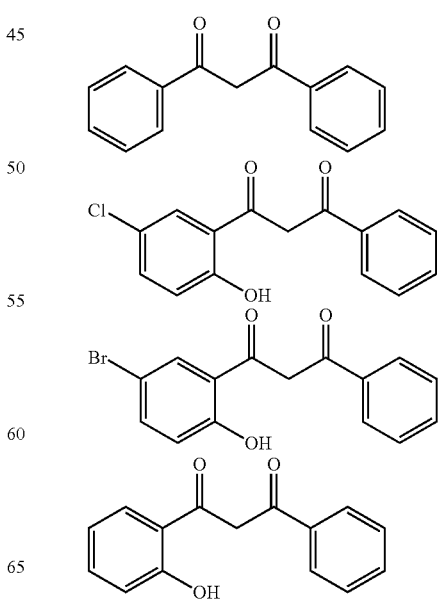

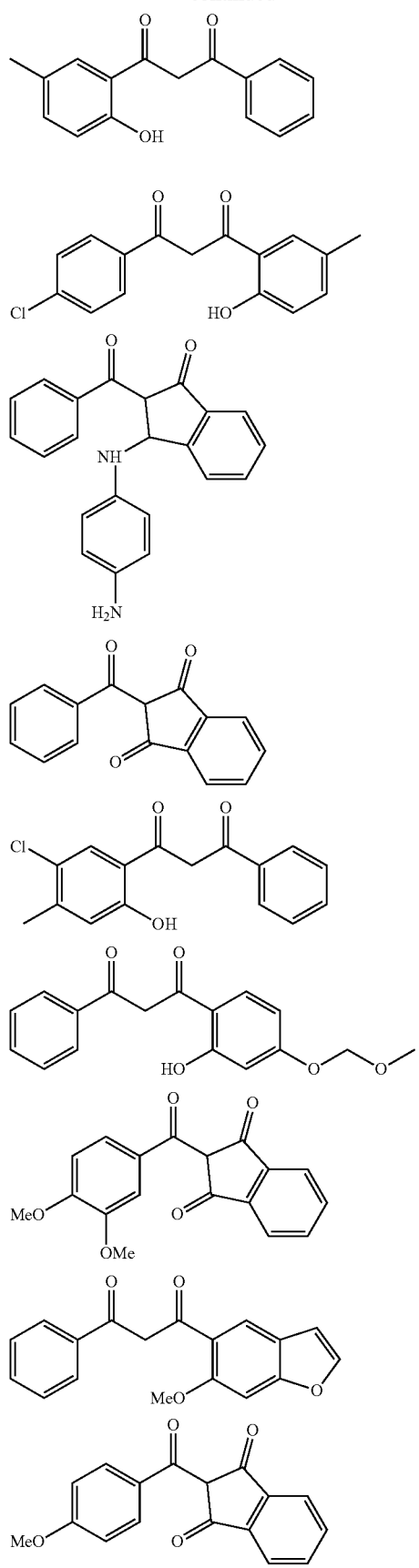
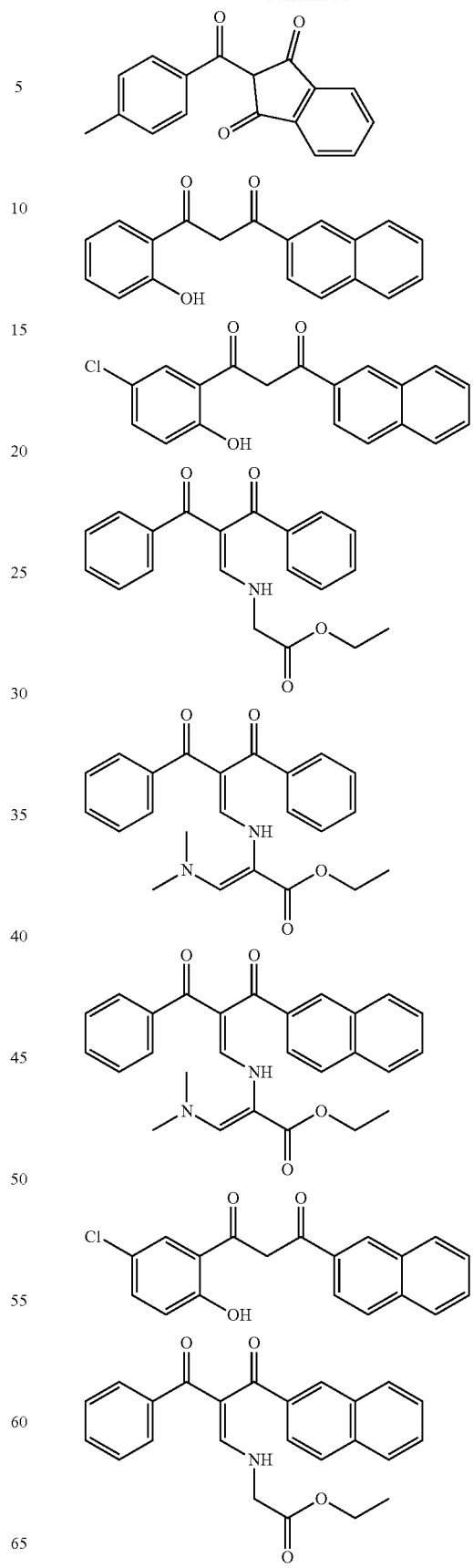

37
-continued

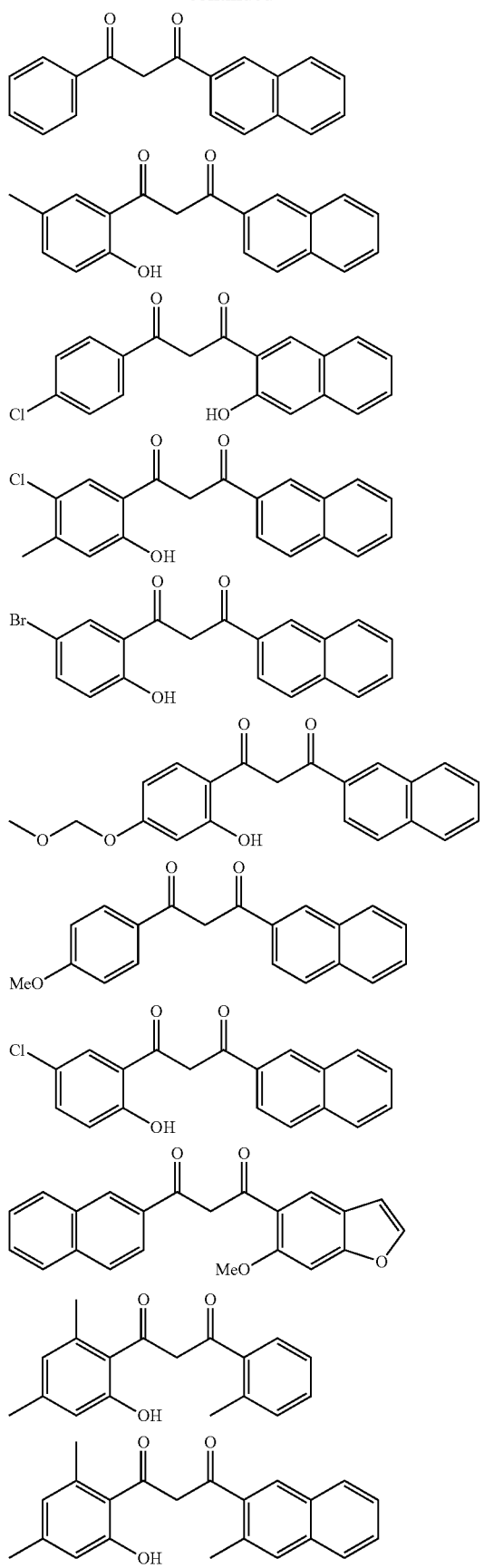

38
-continued

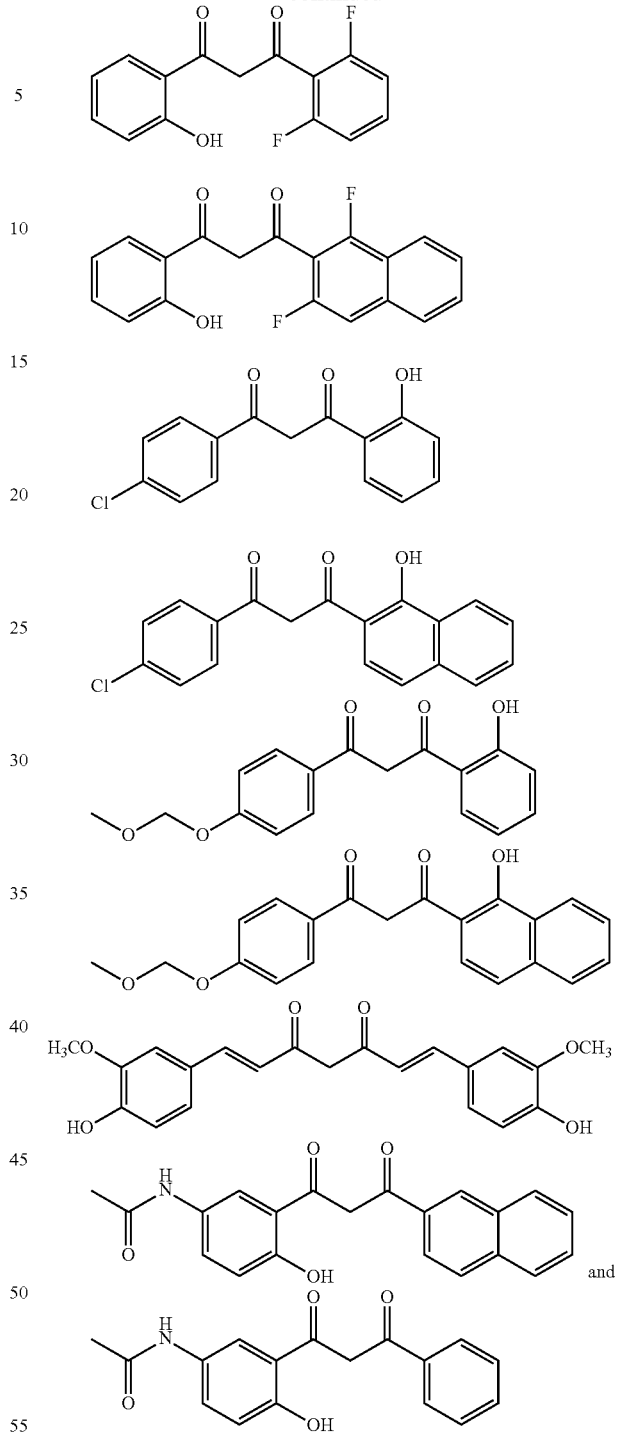

Synthesis of the Boron Polymer, BF₂dbmPLA, Begins with Hydroxyl Functionalized Difluoroboron Dibenzoylmethane (See U.S. Pat. No. 7,955,861).

BF₂dbmOH (1), is prepared for use as an initiator in the ring opening polymerization of lactide to produce BF₂dbm end-functionalized polylactide, BF₂dbmPLA (2). The boron complex, BF₂dbmOH, 1, is synthesized from dbmOH (21) and BF₃.Et₂O in CH₂Cl₂ (60° C., 1 hour). After purification by recrystallization from acetone/hexanes, air stable, bright yellow needles are obtained in good yield (75%). The boron polymer, BF₂dbmPLA, 2, is generated from BF₂dbmOH and DL-lactide using tin octoate, Sn(oct)2, as the ROP catalyst under solvent-free conditions (1:lactide:Sn(oct)2=1:200:1/50) with heating at 130° C. under nitrogen. The reaction is stopped after 1.5 hours (~50% monomer conversion) to avoid broader molecular weight distributions (i.e. higher PDIs) noted for longer reaction times, suggestive of transesterification and thermal depolymerization. After purification by precipitation from $CH_2Cl_2$/cold MeOH and $CH_2Cl_2$/hexanes, a pale greenish yellow polymer is obtained (75% yield, corrected for monomer consumption). Molecular weight data determined by gel permeation chromatography (GPC) and 1H NMR spectroscopy are in good agreement: Mn(GPC/RI)=8,800, PDI=1.09; Mn (NMR)=8,600. Furthermore, key proton resonances associated with the boron dbm end group are evident and shifted as compared to the initiator 1 (e.g. $BF_2$dbmOCH$_2$CH$_2$OR: R=H, 4.04 ppm; R=PLA, 4.32 ppm).

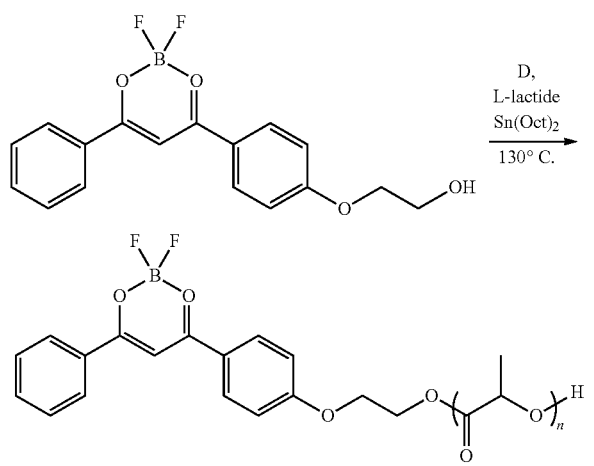

Figure 1C:
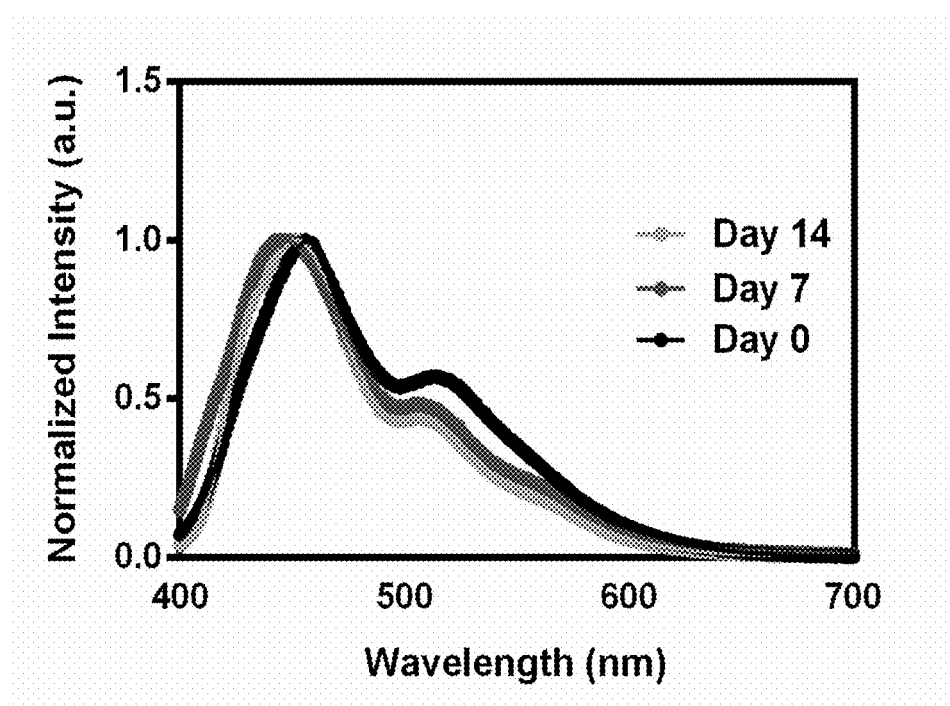

Zhang et al. provide for synthesis starting with an iodinated version of the dye conjugated to a polymer ($BF_2$dbm(I)PLA), that is iodide-substituted difluoroboron dibenzoylmethane-poly(lactic acid) (See FIG. 1 of Zhang et al., 2009, Nature Materials and below)

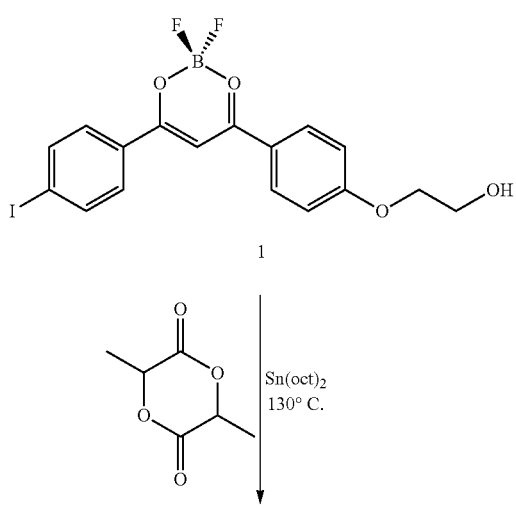

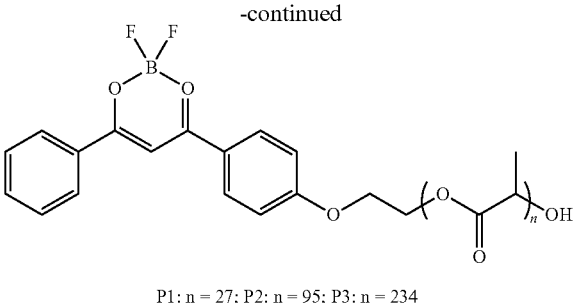

P1: n = 27; P2: n = 95; P3: n = 234

For $BF_2$dbm(I)PLA, Optimization of the electrospinning process yielded final parameters of 30% (w/v) dye-polymer in 10% (v/v) pyridinium formate, 20% (v/v) ethanol, in dichloromethane at a 25 kV applied voltage, 14.5 cm working distance, and 1 mL/hr solution flow rate applied to the 13 kDa PLA alone and the boron dye-polymer conjugate The nanofibrillar structures may be utilized singly or layered to form a multi-layered assembly of nanofibrillar structures for cell or tissue culture.

The nanofibrillar structure of the invention has many in vivo and ex vivo uses including wound repair, growth of artificial skin, veins, arteries, tendons, ligaments, cartilage, heart valves, organ culture, treatment of burns, and bone grafts. In an embodiment, a diverse array of growth environments for a cell or tissue may be constructed by engineering specific chemical and physical properties into the nanofiber network, substrate, and/or spacers comprising the individual nanofibrillar structure elements and/or sequentially layering individual nanofibrillar structures. In certain embodiments, the unique nature of the environment can be obtained from the heterogeneous nature of the fiber diameter and composition. Physical properties and/or characteristics of the individual nanofiber, nanofibrillar structure, and nanofibrillar network including, but not limited to, texture, rugosity, adhesivity, porosity, solidity, elasticity, geometry, interconnectivity, surface to volume ratio, fiber diameter, fiber solubility/insolubility, hydrophilicity/hydrophobicity, and fibril density may be varied and/or modified to construct nano- and/or micro-environments that promote a desired cellular activity, including proliferation and/or differentiation. Specific nano- and/or micro-environments may be engineered within individual nanofibrillar structures or within a cellular array comprising two or more nanofibrillar structures.

The present invention is also directed to methods of manufacturing a tissue. In an embodiment, two or more nanofibrillar structures are layered to form a multi-layered nanofibrillar assembly. Viable cells are deposited on the fiber and the structure is cultured under conditions that promote growth, migration, and/or differentiation of the deposited cells. In a further embodiment, nano- and/or micro-environments that promote cellular activity may be engineered within an individual matrix by varying and/or modifying selected physical and/or chemical properties of the growth matrix.

In another embodiment, multiple cell types are cultured on individual nanofibrillar structures under different culture conditions. Two or more of the individual nanofibrillar structures are then layered to form a multi-layered nanofibrillar assembly and the assembly is cultured under conditions that promote a desired cellular activity, including growth and/or differentiation of the cells. In a further embodiment, nano- and/or micro-environments that promote cellular activity may be engineered within an individual nanofibrillar structure by varying and/or modifying selected physical and/or chemical properties of the nanofibrillar structure or within the nanofibrillar assembly by selectively layering the individual nanofibrillar structures to obtain the desired nano- or micro-environment. Homogeneous or heterogeneous fiber diameters and compositions may be selected to optimize proliferation and/or differentiation.

Electrospinning as a technique is appealing because the physical parameters are easily varied and exert considerable effects on the resulting polymer fiber morphology. (see U.S. Pat. No. 8,728,817, the entirety of which is incorporated by reference herein).

In one aspect, the voltage is applied at a range of about 15 kv to about 25 kv. In another aspect, the voltage is about 20 kv.

Electrospinning is an ideal technology to create implantable 3-D scaffolds. The present invention encompasses methodologies and parameters for the formation of nanofibrous (to microfibrous) polymer mixtures via electrospinning. The present invention further encompasses uses of the resulting nanofibers.

The present invention further provides for the use of other methods and modifications for preparing multiple layers of scaffold or for preparing single layers by mixing the components of the present invention. In one aspect, co-spinning can be used based on a core-shell. In one aspect, dye is one of the materials and the other is the support material. In one aspect, a single nozzle technique is used. In one aspect, two or more needles can be used. In one aspect, when two or more needles are used they can be side-by-side. In one aspect, when two or more needles are used the fibers of two different types of polymer layers are interwoven into a single mat (see Bazilevsky et al., 2007, Langmuir, 23(5), 2251; Han and Steckl, ACS Appl. Mater. Interfaces, 2013, 5(16), 8241; and Wang and Wang, 2012, J. Mater. Sci. Mater. Med., 23(10), 2381).

Specific chemical properties and recognition motifs such as polypeptides, lipids, carbohydrates, amino acids, nucleotides, nucleic acids, polynucleotides, or polysaccharides including, but not limited to growth factors, differentiation factors, fibrous proteins, adhesive proteins, glycoproteins, functional groups, adhesive compounds, deadhesive compounds, and targeting molecules may be engineered into the nanofibrillar network substrate.

In some embodiments, the compositions and structures of the present invention includes additional electroprocessed materials. Other electroprocessed materials can include natural materials, synthetic materials, or combinations thereof. Some preferred examples of natural materials include, but are not limited to, amino acids, peptides, denatured peptides such as gelatin from denatured collagen, polypeptides, proteins, carbohydrates, lipids, nucleic acids, glycoproteins, lipoproteins, glycolipids, glycosaminoglycans, and proteoglycans. Some preferred synthetic matrix materials for electroprocessing with collagen include, but are not limited to, polymers such as poly(lactic acid) (PLA), polyglycolic acid (PGA), copolymers of PLA and PGA, polycaprolactone, poly(ethylene-co-vinyl acetate), (EVOH), poly(vinyl acetate) (PVA), polyethylene glycol (PEG) and poly(ethylene oxide) (PEO).

The present application encompasses conditions and appropriate parameters to synthesize nanofibers comprising mixtures of at least one protein and at least one polymer, wherein the nanofibers range in size from a diameter of about 10 nm to a diameter of over 1,000 nm via electrospinning. Many applications in biology and medicine can be based on the protein-polymer nanofibers or mesh resulting from this procedure. The methodologies described herein are useful for numerous tissue engineering applications.

In one aspect, the sheets of nanofibers are formed upon electrospinning. In one aspect, the sheets comprise one layer. In one aspect, the sheets comprise at least two layers. In another aspect, the sheets comprise at least three layers.

The invention further provides for incorporating or adding additional ingredients, compounds, agents, drugs, or cells, including, but not limited to cell growth and differentiation factors, other extracellular matrix proteins, antibiotics, and antiviral agents, and combinations, derivatives, and analogs thereof.

Some preferred synthetic matrix materials for electrospinning include, but are not limited to, the polymers poly(lactic acid) (PLA), poly (l-lactic acid) (PLLA), polyglycolic acid (PGA), copolymers of PLA and PGA, polycaprolactone (PCL), poly(ethylene-co-vinyl acetate) (EVOH), poly(vinyl acetate) (PVA), polyethylene glycol (PEG), poly(glycerol sebacate) (PGS), poly(d,l-lactic-co-glycolic acid 50:50) (PLGA5050), poly(d-l-lactic-co-glycolic acid 85:15) (PLGA8515), polydioxanone (PDO), polyphosphazenes, polyurethane (PU) and modifications, analogs, and derivatives, thereof, polyhydroxybutyrates (PHB), poly-3-hydroxybutyrate (P3HB), poly-4-hydroxybutyrate (P4HB), polyhydroxyvalerate (PHV), polyhydroxyhexanoate (PHH), polyhydroxyoctanoate (PHO), poly(3-hydroxybutyrate-co-3-hydroxyvalerate) (PHBV), and poly(ethylene oxide) (PEO), as well as co-polymers, analogs, derivatives, modifications, and mixtures thereof.

See also U.S. Pat. Nos. 9,074,129 and 7,955,861.

The present invention provides compositions and methods for mimicking three dimensional scaffolding as found in vivo to better mimic how cells grow and differentiate. Cell proliferation and differentiation are regulated by unique spatial interactions between cells. Spatial cues in conjunction with the topologically distinct location of specific attachment molecules, and the release of specific humoral factors, such as growth and differentiation factors, function as signals to the cell to proliferate, differentiate, migrate, remain in a resting state, or initiate apoptosis. The capacity of the cell to respond to these signaling triggers is dependent on the availability of specific cell surface and intracellular receptors. The signal transduction pathways that are stimulated by these molecules depend on the organization and structure of the cell cytoskeleton whose architecture is a function of multipoint cell surface interactions with these signaling molecules, surrounding cells, and extracellular matrix.

When designing cell and tissue culture environments, it is important to consider the cellular interactions that must be incorporated into the growth environment. Cell types, spatial cues, and chemical triggers and modulators play a significant role in regulating gene expression within interacting cells (Li et al., 2002, FASEB J., 17:97-99; Botarro et al., 2002, Ann. N.Y. Acad. Sci., 961:143-153; Kunz-Schughart et al., 2003, Am. J. Physiol. Cell Physiol., 284:C209-C219; Cukierman et al., 2001, Science, 294:1708-1712). Past advances in the practice of cell and tissue culture have been directed toward providing the biochemical and physical conditions that approximate the complex in vivo microenvironment within a tissue (Cukierman et al., 2001, Science, 23:1708-1712; Li et al., 2002, FASEB J., 17:97-99; Chiu et al., 2000, Proc. Natl. Acad. Sci. USA, 97:2408-2413). These efforts have been limited by factors that include the use of cell lines that have been continuously grown on and selected for their ability to proliferate on planar culture surfaces that lack the spatial cues and chemical triggers and modulators present in tissue in vivo.

Another aspect of the invention is a nanofibrillar structure comprising one or more nanofibers and wherein the nanofibrillar structure is defined by a network of one or more nanofibers. In an embodiment, the nanofiber network is deposited on a surface of a substrate.

In an embodiment, the substrate comprises glass or plastic. In a further embodiment, the substrate is a surface of a culture container.

The nanofibrillar structures may be utilized singly or layered to form a multi-layered assembly of nanofibrillar structures for cell or tissue culture.

The nanofibrillar structure of the invention has many in vivo and ex vivo uses including wound repair, growth of artificial skin, veins, arteries, tendons, ligaments, cartilage, heart valves, organ culture, treatment of burns, and bone grafts. In an embodiment, a diverse array of growth environments for a cell or tissue may be constructed by engineering specific chemical and physical properties into the nanofiber network, substrate, and/or spacers comprising the individual nanofibrillar structure elements and/or sequentially layering individual nanofibrillar structures. In certain embodiments, the unique nature of the environment can be obtained from the heterogeneous nature of the fiber diameter and composition. Physical properties and/or characteristics of the individual nanofiber, nanofibrillar structure, and nanofibrillar network including, but not limited to, texture, rugosity, adhesivity, porosity, solidity, elasticity, geometry, interconnectivity, surface to volume ratio, fiber diameter, fiber solubility/insolubility, hydrophilicity/hydrophobicity, and fibril density may be varied and/or modified to construct nano- and/or micro-environments that promote a desired cellular activity, including proliferation and/or differentiation. Specific nano- and/or micro-environments may be engineered within individual nanofibrillar structures or within a cellular array comprising two or more nanofibrillar structures.

In many desirable embodiments, the electrospun layer or layers are combined with one or more substances. Such substances include any type of molecule, cell, or object or combinations thereof. The electrospun compositions of the present invention can further comprise one substance or any combination of substances. Several especially desirable embodiments include the use of cells as a substance combined with the laminin nanofiber matrix. Any cell can be used.

Cells that can be used include, but are not limited to, stem cells, committed stem cells, and differentiated cells. One embodiment includes cells as a substance combined with the electrospun materials. Any cell type can be used. Some preferred examples include, but are not limited to, stem cells, committed stem cells, and differentiated cells. Examples of stem cells include, but are not limited to, embryonic stem cells, bone marrow stem cells, adipose stem cells, and umbilical cord stem cells. Other examples of cells include, but are not limited to, isolated islet cells, osteoblasts, myoblasts, neuroblasts, fibroblasts, glioblasts, germ cells, hepatocytes, chondrocytes, keratinocytes, smooth muscle cells, cardiac muscle cells, connective tissue cells, glial cells, epithelial cells, endothelial cells, hormone-secreting cells, cells of the immune system, and neurons. In some embodiments, it is unnecessary to pre-select the type of stem cell that is to be used, because many types of stem cells can be induced to differentiate in an organ specific pattern once delivered to a given organ.

Embodiments in which the substance comprises cells include cells that can be cultured in vitro, derived from a natural source, genetically engineered, or produced by any other means. Any natural source of prokaryotic or eukaryotic cells may be used. Embodiments in which the matrix is implanted in an organism can use cells from the recipient, cells from a conspecific donor or a donor from a different species, or bacteria or microbial cells. Cells harvested from a source and cultured prior to use are included.

Some embodiments use cells that have been genetically engineered. The engineering involves programming the cell to express one or more genes, repressing the expression of one or more genes, or both. One example of genetically engineered cells useful in the present invention is a genetically engineered cell that makes and secretes one or more desired molecules. When electrospun laminin matrices comprising genetically engineered cells are implanted in an organism, the molecules produced can produce a local effect or a systemic effect, and can include the molecules identified above as possible substances. Cells can also produce antigenic materials in embodiments in which one of the purposes of the matrix is to produce an immune response. Cells may produce substances to aid in the following non-inclusive list of purposes: inhibit or stimulate inflammation; facilitate healing; resist immunorejection; provide hormone replacement; replace neurotransmitters; inhibit or destroy cancer cells; promote cell growth; inhibit or stimulate formation of blood vessels; augment tissue; and to supplement or replace neurons, skin, synovial fluid, tendons, cartilage (including, but not limited to articular cartilage), ligaments, bone, muscle, organs, dura, blood vessels, bone marrow, and extracellular matrix.

In many embodiments, cells in an electrospun matrix exhibit characteristics and functions typical of such cells in vivo.

Molecules can be present in any phase or form and combinations of molecules can be used. Examples of desirable classes of molecules that can be used include human or veterinary therapeutics, cosmetics, nutraceuticals, agriculturals such as herbicides, pesticides and fertilizers, vitamins, amino acids, peptides, polypeptides, proteins, carbohydrates, lipids, nucleic acids, glycoproteins, lipoproteins, glycolipids, glycosaminoglycans, proteoglycans, growth factors, hormones, neurotransmitters, pheromones, chalones, prostaglandins, immunoglobulins, monokines and other cytokines, humectants, metals, gases, plasticizers, minerals, ions, electrically and magnetically reactive materials, light sensitive materials, anti-oxidants, molecules that can be metabolized as a source of cellular energy, antigens, and any molecules that can cause a cellular or physiological response. Examples of objects include, but are not limited to, cell fragments, cell debris, organelles and other cell components, extracellular matrix constituents, tablets, and viruses, as well as vesicles, liposomes, capsules, nanoparticles, and other structures that serve as an enclosure for molecules. Magnetically or electrically reactive materials are also examples of substances that are optionally included within compositions of the present invention. Examples of electrically active materials include, but are not limited, to carbon black or graphite, carbon nanotubes, and various dispersions of electrically conducting polymers. Examples of magnetically active materials include, but are not limited to, ferrofluids (colloidal suspensions of magnetic particles).

Growth Factors

In one embodiment, at least one growth factor, cytokine, hormone, or extracellular matrix compound or protein is attached to or conjugated to the scaffold of the invention. In one aspect, one or more growth factors are administered separately from the scaffold. In one aspect, a combination of these agents is used. In one aspect, growth factors useful in the practice of the invention include, but are not limited to, CRF, EGF, PDGF, GCSF, GM-CSF, IL6, IL8, IL10, MCP1, MCP2, Tissue Factor, FGFb, KGF, NGF, VEGF, PDGF, MMP1, MMP9, TIMP1, TIMP2, TGFβ, interferons, and HGF. One of ordinary skill in the art will appreciate that the choice of growth factor, cytokine, hormone, or extracellular matrix protein used will vary depending on criteria such as the type of injury, disease, or disorder being treated, the age, health, sex, and weight of the subject, etc. In one aspect, the growth factors, cytokines, hormones, and extracellular matrix compounds and proteins are human.

Proteins and other biologically active compounds that can be incorporated into or on the scaffold, or included as an additive of the present invention include, but are not limited to, collagen (including cross-linked collagen), adhesion molecules, fibronectin, laminin, elastin (including cross-linked elastin), osteopontin, osteonectin, bone sialoproteins (Bsp), alpha-2HS-glycoproteins, bone Gla-protein (Bgp), matrix Gla-protein, bone phosphoglycoprotein, bone phosphoprotein, bone proteoglycan, protolipids, bone morphogenetic protein, cartilage induction factor, skeletal growth factor, enzymes, or combinations and biologically active fragments thereof. Adjuvants that diminish an immune response can also be used in conjunction with the composite of the subject invention.

Other molecules useful as compounds or substances in the present invention include, but are not limited to, growth hormones, leptin, leukemia inhibitory factor (LIF), tumor necrosis factor alpha and beta, endostatin, angiostatin, thrombospondin, osteogenic protein-1, bone morphogenetic proteins 2 and 7, osteonectin, somatomedin-like peptide, osteocalcin, interferon alpha, interferon alpha A, interferon beta, interferon gamma, interferon 1 alpha, and interleukins 2, 3, 4, 5 6, 7, 8, 9, 10, 11, 12, 13, 15, 16, 17 and 18. Embodiments involving amino acids, peptides, polypeptides, and proteins may include any type of such molecules of any size and complexity as well as combinations of such molecules.

The types of injuries, disease, and disorders encompassed by the methods of the invention therefore include, bone trauma, diseases and disorders, burns, chronic wounds, and surgical procedures such as microvascular surgery, skin flaps and skin grafts, and tissue injury resulting from, for example, a burn, scrape, cut, incision, laceration, ulcer, body piercing, bite wound, trauma, stab wound, gunshot wound, surgical wound, stretch injury, crush wound, compression wound, fracture, sprain, strain, stroke, infarction, aneurysm, herniation, ischemia, fistula, dislocation, radiation, cell, tissue or organ grafting and transplantation, injuries sustained during medical procedures, or cancer.

Such injuries include, but are not limited to, bone injury, skin injury, muscle injury, brain injury, eye injury, or spinal cord injury. Tissue injury can include joint injury, back injury, heart injury, vascular system injury, soft tissue injury, cartilage injury, lymphatic system injury, tendon injury, ligament injury, or abdominal injury.

While it is important to treat any condition in which the potential for cell or tissue damage exists immediately (e.g., an acute wound), it is essential that certain conditions be treated before they become chronic conditions. Chronic diseases are a challenge to the patient, the health care professional, and to the health care system. They significantly impair the quality of life for millions of people in the United States. Intensive treatment is required with a high cost to society in terms of lost productivity and health care dollars. The management of chronic diseases can place an enormous strain on health care resources. Diseases or conditions, for example, wounds that were once acute but have progressed to chronic often do so because the diseases cannot be controlled or treated with known therapies. Therefore, there is a need for improved therapies for treating chronic diseases and conditions characterized by cell and tissue damage.

Other non-limiting examples of wounds suitable for treatment in accordance with the present disclosure include trauma, fractures, animal bites, arterial disease, insect stings and bites, bone infections, compromised skin/muscle grafts, gangrene, skin tears or lacerations, surgical incisions, including slow or non-healing surgical wounds, and post-operation infections. It is understood, that the listed wounds are non-limiting and that only a portion of wounds suitable for treatment in accordance with the present disclosure are listed herein.

Examples of additional additives include but are not limited to: (a) antimicrobials, (b) steroids (e.g., hydrocortisone, triamcinolone); (c) pain medications (e.g., aspirin, an NSAID, and a local anesthetic); (d) anti-inflammatory agents; (e) growth factors; (f) cytokines; (g) hormones; and (h) combinations thereof.

The types of drugs and specific drugs within categories which are encompassed within the invention are intended to be non-limiting examples.

In one embodiment, a formulation of the invention contains an antimicrobial agent. The antimicrobial agent may be provided at, for example, a standard therapeutically effective amount. A standard therapeutically effective amount is an amount that is typically used by one of ordinary skill in the art or an amount approved by a regulatory agency (e.g., the FDA or its European counterpart). Antimicrobial agents useful for the invention include those directed against the spectra of gram positive organisms, gram negative organisms, fungi, and viruses.

The present invention provides for the use of anesthetics. According to the topical anesthetic embodiment of the present invention, in one aspect, suitable local anesthetic agents having a melting point of 30° to 70° C. are prilocaine, tetracaine, butanilcaine, trimecaine, benzocaine, lidocaine, bupivocaine, dibucaine, mepivocaine, and etidocaine.

The present invention further encompasses the use of at least two anesthetics.

The local anesthetic composition of the present invention may further comprise suitable additives, such a pigment, a dye, an anti-oxidant, a stabilizer or a fragrance provided that addition of such an additive does not destroy the single phase of the anesthetic composition.

By selecting different materials for combining with electrospun layers and scaffolds, or combinations thereof, many characteristics of the electroprocessed material can be manipulated. The properties of a matrix comprised of electrospun laminin may be adjusted. Electroprocessed materials can provide a therapeutic effect when applied. In addition, selection of matrix materials can affect the permanency of an implanted matrix. Use of matrices made of natural materials such as proteins also minimize rejection or immunological response to an implanted matrix. Accordingly, selection of materials for electroprocessing and use in substance delivery is influenced by the desired use. In one embodiment, an electrospun implant for delivery of pancreatic islets may be constructed. In embodiments in which the matrix contains substances that are to be released from the matrix, incorporating electroprocessed synthetic components, such as biocompatible substances, can modulate the release of substances from an electroprocessed composition. For example, layered or laminate structures can be used to control the substance release profile. Unlayered structures can also be used, in which case the release is controlled by the relative stability of each component of the construct. For example, layered structures composed of alternating electroprocessed materials are prepared by sequentially electroprocessing different materials onto a target. The outer layers are, for example, tailored to dissolve faster or slower than the inner layers. Multiple agents can be delivered by this method, optionally at different release rates. Layers can be tailored to provide a complex, multi-kinetic release profile of a single agent over time. Using combinations of the foregoing provides for release of multiple substances released, each with a complex profile.

In embodiments in which the substances or compounds are molecules, any molecule can be used. Molecules may, for example, be organic or inorganic and may be in a solid, semisolid, liquid, or gas phase. Molecules may be present in combinations or mixtures with other molecules, and may be in solution, suspension, or any other form. Examples of classes of molecules that may be used include human or veterinary therapeutics, cosmetics, nutraceuticals, agriculturals such as herbicides, pesticides and fertilizers, vitamins, salts, electrolytes, amino acids, peptides, polypeptides, proteins, carbohydrates, lipids, nucleic acids, glycoproteins, lipoproteins, glycolipids, glycosaminoglycans, proteoglycans, growth factors, hormones, neurotransmitters, pheromones, chalones, prostaglandins, immunoglobulins, monokines and other cytokines, humectants, metals, gases, minerals, plasticizers, ions, electrically and magnetically reactive materials, light sensitive materials, anti-oxidants, molecules that may be metabolized as a source of cellular energy, antigens, and any molecules that can cause a cellular or physiological response. Any combination of molecules can be used, as well as agonists or antagonists of these molecules.

Several preferred embodiments include use of any therapeutic molecule including, without limitation, any pharmaceutical or drug. Examples of pharmaceuticals include, but are not limited to, anesthetics, hypnotics, sedatives and sleep inducers, antipsychotics, antidepressants, antiallergics, antianginals, antiarthritics, antiasthmatics, antidiabetics, antidiarrheal drugs, anticonvulsants, antigout drugs, antihistamines, antipruritics, emetics, antiemetics, antispasmodics, appetite suppressants, neuroactive substances, neurotransmitter agonists, antagonists, receptor blockers and reuptake modulators, beta-adrenergic blockers, calcium channel blockers, disulfiram and disulfiram-like drugs, muscle relaxants, analgesics, antipyretics, stimulants, anticholinesterase agents, parasympathomimetic agents, hormones, anticoagulants, antithrombotics, thrombolytics, immunoglobulins, immunosuppressants, hormone agonists/antagonists, vitamins, antimicrobial agents, antineoplastics, antacids, digestants, laxatives, cathartics, antiseptics, diuretics, disinfectants, fungicides, ectoparasiticides, antiparasitics, heavy metals, heavy metal antagonists, chelating agents, gases and vapors, alkaloids, salts, ions, autacoids, digitalis, cardiac glycosides, antiarrhythmics, antihypertensives, vasodilators, vasoconstrictors, antimuscarinics, ganglionic stimulating agents, ganglionic blocking agents, neuromuscular blocking agents, adrenergic nerve inhibitors, anti-oxidants, vitamins, cosmetics, anti-inflammatories, wound care products, antithrombogenic agents, antitumoral agents, antiangiogenic agents, anesthetics, antigenic agents, wound healing agents, plant extracts, growth factors, emollients, humectants, rejection/anti-rejection drugs, spermicides, conditioners, antibacterial agents, antifungal agents, antiviral agents, antibiotics, tranquilizers, cholesterol-reducing drugs, antitussives, histamine-blocking drugs, monoamine oxidase inhibitor. All substances listed by the U.S. Pharmacopeia are also included within the substances of the present invention.

Other preferred embodiments involve the use of growth factors, including more than one growth factor, as described herein.

Embodiments involving amino acids, peptides, polypeptides, and proteins may include any type of such molecules of any size and complexity as well as combinations of such molecules. Examples include, but are not limited to, structural proteins, enzymes, and peptide hormones. These compounds can serve a variety of functions. In some embodiments, the matrix may contain peptides containing a sequence that suppresses enzyme activity through competition for the active site. In other applications, antigenic agents that promote an immune response and invoke immunity can be incorporated into a construct.

For substances such as nucleic acids, any nucleic acid can be present. Examples include, but are not limited to deoxyribonucleic acid (DNA), ent-DNA, oligonucleotides, aptamers, and ribonucleic acid (RNA). Embodiments involving DNA include, but are not limited to, cDNA sequences, natural DNA sequences from any source, and sense or anti-sense oligonucleotides. For example, DNA can be naked (e.g., U.S. Pat. Nos. 5,580,859; 5,910,488) or complexed or encapsulated (e.g., U.S. Pat. Nos. 5,908,777; 5,787,567). DNA can be present in vectors of any kind, for example in a viral or plasmid vector. In some embodiments, nucleic acids used will serve to promote or to inhibit the expression of genes in cells inside and/or outside the electroprocessed matrix. The nucleic acids can be in any form that is effective to enhance uptake into cells.

Substances or compounds in the electrospun compositions of the present invention also comprise objects. Examples of objects include, but are not limited to, cell fragments, cell debris, organelles and other cell components, tablets, and viruses as well as vesicles, liposomes, capsules, nanoparticles, and other structures that serve as an enclosure for molecules. In some embodiments, the objects constitute vesicles, liposomes, capsules, or other enclosures that contain compounds that are released at a time after electroprocessing, such as at the time of implantation or upon later stimulation or interaction. In one illustrative embodiment, transfection agents such as liposomes contain desired nucleotide sequences to be incorporated into cells that are located in or on the electroprocessed material or mesh. In other embodiments, cell fragments, specific cell fractions or cell debris are incorporated into the mesh. The presence of cell fragments is known to promote healing in some tissues.

Compounds and substances that can provide favorable matrix or mesh characteristics also include drugs and other substances that can produce a therapeutic or other physiological effect on cells and tissues within or surrounding an implant. Any substance may be used. In some embodiments, substances are included in the electrospun matrix that will improve the performance of the implanted electrospun matrix. Examples of substances that can be used include but are not limited to peptide growth factors, antibiotics, and/or anti-rejection drugs. Chemicals that affect cell function, such as oligonucleotides, promoters or inhibitors of cell adhesion, hormones, and growth factor are additional examples of substances that can be incorporated into the electroprocessed collagen material and the release of those substances from the electroprocessed material can provide a means of controlling expression or other functions of cells in the electroprocessed material.

Alternatively, cells that are engineered to manufacture desired compounds can be included. The entire construct is, for example, cultured in a bioreactor or conventional culture or placed directly in vivo. For example, neovascularization can be stimulated by angiogenic and growth-promoting factors, administered, as peptides, proteins or as gene therapy.

Angiogenic agents can be incorporated into the electroprocessed matrix. Alternatively, where neovascularization is not desired, antiangiogenic materials, such as angiostatin, may be included in the electroprocessed matrix. Nerve growth factors can be electrospun into the electrospun matrix to promote growth of neurons into the matrix and tissue. In a degradable electrospun matrix, the gradual degradation/breakdown of the matrix will release these factors and accelerate growth of desired tissues. Substances can be incorporated into the electrospun matrix to regulate differentiation of cells in the matrix. Oligonucleotides and peptides drugs such as retinoic acid are examples of such compounds and substances. Oligonucleotide DNA or messenger RNA sequences coding for specific proteins in the sense and antisense direction can also be used. For example, where expression of a protein is desired, sense oligonucleotides can be provided for uptake by cells and expression. Antisense oligonucleotides can be released, for example, to suppress the expression gene sequences of interest. Implants can be designed such that the substances affect cells contained within the matrix, outside the matrix or both.

Several methods exist for studying and quantifying specific characteristics of the matrix materials of the present invention.

In the most fundamental sense, the electroprocessing apparatus for electroprocessing material includes an electrodepositing mechanism and a target. The present invention allows forming matrices that have a predetermined shape.

In one embodiment, the electrospun materials form a matrix. The term "matrix" refers to any structure comprised of electroprocessed materials. Matrices are comprised of fibers, or droplets of materials, or blends of fibers and droplets of any size or shape, including the layers as disclosed herein. Matrices are single structures or groups of structures and can be formed through one or more electroprocessing methods using one or more materials. Matrices are engineered to possess specific porosities. Substances can be deposited within, or anchored to or placed on matrices. Cells are substances which can be deposited within or on matrices.

Any solvent can be used that allows delivery of the material or substance to the orifice, tip of a syringe, or other site from which the material will be electrospun. In one aspect, the electrospun material must maintain an activity as indicated. In one aspect, an appropriate solvent for a protein is HFP. The solvent may be used for dissolving or suspending the material or the substance to be electroprocessed. Solvents useful for dissolving or suspending a material or a substance depend on the material or substance. Electrospinning techniques often require more specific solvent conditions.

One of ordinary skill in the art recognizes that changes in the concentration of materials or substances in the solutions requires modification of the specific voltages to obtain the formation and streaming of droplets from the tip of a pipette or device being used.

The electrospinning process can be manipulated to meet the specific requirements for any given application of the electrospun compositions made with these methods.

In the electrospinning process, the stream or streams can branch out to form fibers. The degree of branching can be varied by many factors including, but not limited to, voltage, ground geometry, distance from micropipette tip (such as a needle or syringe) to the collector surface, diameter of micropipette tip, and concentration of materials or compounds that will form the electroprocessed materials. This process can be varied by many factors including, but not limited to, voltage (for example ranging from about 0 to 30,000 volts), distance from micropipette tip to the substrate (for example from 0-40 cm), the relative position of the micropipette tip and target (i.e. above, below, aside etc.), and the diameter of micropipette tip (approximately 0-2 mm).

The geometry of the grounded target can be modified to produce a desired matrix. By varying the ground geometry, for instance having a planar or linear or multiple points ground, the direction of the streaming materials can be varied and customized to a particular application.

The compositions and substances of the invention are also useful for preparing engineered tissue. Once the electroengineered tissue containing electrospun materials and cells is assembled, the tissue can be inserted into a recipient. Alternatively, the structure can be placed into a culture to enhance the cell growth. Different types of nutrients and growth factors can be added to a culture (or administered to a recipient) in order to promote a specific type of growth of the engineered tissue.

In some embodiments, the stem cells or other cells used to construct the implant are isolated from the subject, or other compatible donor requiring tissue reconstruction. This provides the advantage of using cells that will not induce an immune response, because they originated with the subject (autologous tissue) requiring the reconstruction. Relatively small biopsies can be used to obtain a sufficient number of cells to construct the implant. This minimizes functional deficits and damage to endogenous tissues that serve as the donor site for the cells.

The electrospun compositions of the present invention have a broad array of potential uses. Uses include, but are not limited to, manufacture of engineered tissue and organs, including structures such as patches or plugs of tissues or matrix material, prosthetics, and other implants, tissue scaffolding, repair or dressing of wounds, hemostatic devices, devices for use in tissue repair and support such as sutures, surgical and orthopedic screws, and surgical and orthopedic plates, natural coatings or components for synthetic implants, cosmetic implants and supports, repair or structural support for organs or tissues, substance delivery, bioengineering platforms, platforms for testing the effect of substances upon cells, cell culture, and numerous other uses. This discussion of possible uses is not intended to be exhaustive and many other embodiments exist.

The ability to combine cells in an electrospun composition, whether comprising, one, two, or more layers, provides the ability to use the compositions of the present invention to build tissue, organs, or organ-like tissue. Cells included in such tissues or organs can include cells that serve a function of delivering a substance, seeded cells that will provide the beginnings of replacement tissue, or both. Many types of cells can be used to create tissue or organs. Stem cells, committed stem cells, and/or differentiated cells are used in various embodiments.

The peptides of the present invention may be readily prepared by standard, well-established techniques, such as solid-phase peptide synthesis (SPPS) as described by Stewart et al. in Solid Phase Peptide Synthesis, 2nd Edition, 1984, Pierce Chemical Company, Rockford, Ill.; and as described by Bodanszky and Bodanszky in The Practice of Peptide Synthesis, 1984, Springer-Verlag, New York. At the outset, a suitably protected amino acid residue is attached through its carboxyl group to a derivatized, insoluble polymeric support, such as cross-linked polystyrene or polyamide resin. "Suitably protected" refers to the presence of protecting groups on both the α-amino group of the amino acid, and on any side chain functional groups. Side chain protecting groups are generally stable to the solvents, reagents and reaction conditions used throughout the synthesis, and are removable under conditions which will not affect the final peptide product. Stepwise synthesis of the oligopeptide is carried out by the removal of the N-protecting group from the initial amino acid, and couple thereto of the carboxyl end of the next amino acid in the sequence of the desired peptide. This amino acid is also suitably protected. The carboxyl of the incoming amino acid can be activated to react with the N-terminus of the support-bound amino acid by formation into a reactive group such as formation into a carbodiimide, a symmetric acid anhydride, or an "active ester" group such as hydroxybenzotriazole or pentafluorophenly esters.

Examples of solid phase peptide synthesis methods include the BOC method which utilized tert-butyloxcarbonyl as the α-amino protecting group, and the FMOC method which utilizes 9-fluorenylmethyloxcarbonyl to protect the α-amino of the amino acid residues, both methods of which are well known by those of skill in the art.

Incorporation of N- and/or C-blocking groups can also be achieved using protocols conventional to solid phase peptide synthesis methods. For incorporation of C-terminal blocking groups, for example, synthesis of the desired peptide is typically performed using, as solid phase, a supporting resin that has been chemically modified so that cleavage from the resin results in a peptide having the desired C-terminal blocking group. To provide peptides in which the C-terminus bears a primary amino blocking group, for instance, synthesis is performed using a p-methylbenzhydrylamine (MBHA) resin so that, when peptide synthesis is completed, treatment with hydrofluoric acid releases the desired C-terminally amidated peptide. Similarly, incorporation of an N-methylamine blocking group at the C-terminus is achieved using N-methylaminoethyl-derivatized DVB, resin, which upon HF treatment releases a peptide bearing an N-methylamidated C-terminus. Blockage of the C-terminus by esterification can also be achieved using conventional procedures. This entails use of resin/blocking group combination that permits release of side-chain peptide from the resin, to allow for subsequent reaction with the desired alcohol, to form the ester function. FMOC protecting group, in combination with DVB resin derivatized with methoxyalkoxybenzyl alcohol or equivalent linker, can be used for this purpose, with cleavage from the support being effected by TFA in dicholoromethane. Esterification of the suitably activated carboxyl function e.g. with DCC, can then proceed by addition of the desired alcohol, followed by deprotection and isolation of the esterified peptide product.

Incorporation of N-terminal blocking groups can be achieved while the synthesized peptide is still attached to the resin, for instance by treatment with a suitable anhydride and nitrile. To incorporate an acetyl-blocking group at the N-terminus, for instance, the resin-coupled peptide can be treated with 20% acetic anhydride in acetonitrile. The N-blocked peptide product can then be cleaved from the resin, deprotected and subsequently isolated.

To ensure that the peptide obtained from either chemical or biological synthetic techniques is the desired peptide, analysis of the peptide composition should be conducted. Such amino acid composition analysis may be conducted using high-resolution mass spectrometry to determine the molecular weight of the peptide. Alternatively, or additionally, the amino acid content of the peptide can be confirmed by hydrolyzing the peptide in aqueous acid, and separating, identifying and quantifying the components of the mixture using HPLC, or an amino acid analyzer. Protein sequenators, which sequentially degrade the peptide and identify the amino acids in order, may also be used to determine definitely the sequence of the peptide. Prior to its use, the peptide is purified to remove contaminants. In this regard, it will be appreciated that the peptide will be purified so as to meet the standards set out by the appropriate regulatory agencies. Any one of a number of a conventional purification procedures may be used to attain the required level of purity including, for example, reversed-phase high-pressure liquid chromatography (HPLC) using an alkylated silica column such as C4-, C8- or C18-silica. A gradient mobile phase of increasing organic content is generally used to achieve purification, for example, acetonitrile in an aqueous buffer, usually containing a small amount of trifluoroacetic acid. Ion-exchange chromatography can be also used to separate peptides based on their charge.

It will be appreciated, of course, that the peptides or antibodies, derivatives, or fragments thereof may incorporate amino acid residues which are modified without affecting activity. For example, the termini may be derivatized to include blocking groups, i.e. chemical substituents suitable to protect and/or stabilize the N- and C-termini from "undesirable degradation", a term meant to encompass any type of enzymatic, chemical or biochemical breakdown of the compound at its termini which is likely to affect the function of the compound, i.e. sequential degradation of the compound at a terminal end thereof.

Blocking groups include protecting groups conventionally used in the art of peptide chemistry which will not adversely affect the in vivo activities of the peptide. For example, suitable N-terminal blocking groups can be introduced by alkylation or acylation of the N-terminus. Examples of suitable N-terminal blocking groups include $C_1$-$C_5$ branched or unbranched alkyl groups, acyl groups such as formyl and acetyl groups, as well as substituted forms thereof, such as the acetamidomethyl (Acm) group. Desamino analogs of amino acids are also useful N-terminal blocking groups, and can either be coupled to the N-terminus of the peptide or used in place of the N-terminal reside. Suitable C-terminal blocking groups, in which the carboxyl group of the C-terminus is either incorporated or not, include esters, ketones or amides. Ester or ketone-forming alkyl groups, particularly lower alkyl groups such as methyl, ethyl and propyl, and amide-forming amino groups such as primary amines (—$NH_2$), and mono- and di-alkylamino groups such as methylamino, ethylamino, dimethylamino, diethylamino, methylethylamino and the like are examples of C-terminal blocking groups. Descarboxylated amino acid analogues such as agmatine are also useful C-terminal blocking groups and can be either coupled to the peptide's C-terminal residue or used in place of it. Further, it will be appreciated that the free amino and carboxyl groups at the termini can be removed altogether from the peptide to yield desamino and descarboxylated forms thereof without affect on peptide activity.

Other modifications can also be incorporated without adversely affecting the activity and these include, but are not limited to, substitution of one or more of the amino acids in the natural L-isomeric form with amino acids in the D-isomeric form. Thus, the peptide may include one or more D-amino acid resides, or may comprise amino acids which are all in the D-form. Retro-inverso forms of peptides in accordance with the present invention are also contemplated, for example, inverted peptides in which all amino acids are substituted with D-amino acid forms.

Acid addition salts of the present invention are also contemplated as functional equivalents. Thus, a peptide in accordance with the present invention treated with an inorganic acid such as hydrochloric, hydrobromic, sulfuric, nitric, phosphoric, and the like, or an organic acid such as an acetic, propionic, glycolic, pyruvic, oxalic, malic, malonic, succinic, maleic, fumaric, tataric, citric, benzoic, cinnamie, mandelic, methanesulfonic, ethanesulfonic, p-toluenesulfonic, salicyclic and the like, to provide a water soluble salt of the peptide is suitable for use in the invention.

The present invention also provides for homologs of proteins and peptides. Homologs can differ from naturally occurring proteins or peptides by conservative amino acid sequence differences or by modifications which do not affect sequence, or by both.

For example, conservative amino acid changes may be made, which although they alter the primary sequence of the protein or peptide, do not normally alter its function. To that end, depending on the size of the peptide, 10 or more conservative amino acid changes typically have no effect on peptide function.

Modifications (which do not normally alter primary sequence) include in vivo, or in vitro chemical derivatization of polypeptides, e.g., acetylation, or carboxylation. Also included are modifications of glycosylation, e.g., those made by modifying the glycosylation patterns of a polypeptide during its synthesis and processing or in further processing steps; e.g., by exposing the polypeptide to enzymes which affect glycosylation, e.g., mammalian glycosylating or deglycosylating enzymes. Also embraced are sequences which have phosphorylated amino acid residues, e.g., phosphotyrosine, phosphoserine, or phosphothreonine.

Substantially pure protein obtained as described herein may be purified by following known procedures for protein purification, wherein an immunological, enzymatic or other assay is used to monitor purification at each stage in the procedure. Protein purification methods are well known in the art, and are described, for example in Deutscher et al. (ed., 1990, Guide to Protein Purification, Harcourt Brace Jovanovich, San Diego).

The present invention also provides nucleic acids encoding peptides, proteins, and antibodies of the invention. By "nucleic acid" is meant any nucleic acid, whether composed of deoxyribonucleosides or ribonucleosides, and whether composed of phosphodiester linkages or modified linkages such as phosphotriester, phosphoramidate, siloxane, carbonate, carboxymethylester, acetamidate, carbamate, thioether, bridged phosphoramidate, bridged methylene phosphonate, bridged phosphoramidate, bridged phosphoramidate, bridged methylene phosphonate, phosphorothioate, methylphosphonate, phosphorodithioate, bridged phosphorothioate or sulfone linkages, and combinations of such linkages. The term nucleic acid also specifically includes nucleic acids composed of bases other than the five biologically occurring bases (adenine, guanine, thymine, cytosine and uracil).

It is not intended that the present invention be limited by the nature of the nucleic acid employed. The target nucleic acid may be native or synthesized nucleic acid. The nucleic acid may be from a viral, bacterial, animal or plant source.

The nucleic acid may be DNA or RNA and may exist in a double-stranded, single-stranded or partially double-stranded form. Furthermore, the nucleic acid may be found as part of a virus or other macromolecule. See, e.g., Fasbender et al., 1996, J. Biol. Chem. 272:6479-89 (polylysine condensation of DNA in the form of adenovirus).

Nucleic acids useful in the present invention include, by way of example and not limitation, oligonucleotides and polynucleotides such as antisense DNAs and/or RNAs; ribozymes; DNA for gene therapy; viral fragments including viral DNA and/or RNA; DNA and/or RNA chimeras; mRNA; plasmids; cosmids; genomic DNA; cDNA; gene fragments; various structural forms of DNA including single-stranded DNA, double-stranded DNA, supercoiled DNA and/or triple-helical DNA; Z-DNA; and the like. The nucleic acids may be prepared by any conventional means typically used to prepare nucleic acids in large quantity. For example, DNAs and RNAs may be chemically synthesized using commercially available reagents and synthesizers by methods that are well-known in the art (see, e.g., Gait, 1985, OLIGONUCLEOTIDE SYNTHESIS: A PRACTICAL APPROACH (IRL Press, Oxford, England)). RNAs may be produce in high yield via in vitro transcription using plasmids such as SP65 (Promega Corporation, Madison, Wis.).

In some circumstances, as where increased nuclease stability is desired, nucleic acids having modified internucleoside linkages may be preferred. Nucleic acids containing modified internucleoside linkages may also be synthesized using reagents and methods that are well known in the art. For example, methods for synthesizing nucleic acids containing phosphonate phosphorothioate, phosphorodithioate, phosphoramidate methoxyethyl phosphoramidate, formacetal, thioformacetal, diisopropylsilyl, acetamidate, carbamate, dimethylene-sulfide (—CH2-S—CH2), diinethylene-sulfoxide (—CH2-SO—CH2), dimethylene-sulfone (—CH2-SO2-CH2), 2'-O-alkyl, and 2'-deoxy2'-fluoro phosphorothioate internucleoside linkages are well known in the art (see Uhlmann et al., 1990, Chem. Rev. 90:543-584; Schneider et al., 1990, Tetrahedron Lett. 31:335 and references cited therein).

The nucleic acids may be purified by any suitable means, as are well known in the art. For example, the nucleic: acids can be purified by reverse phase or ion exchange HPLC, size exclusion chromatography or gel electrophoresis. Of course, the skilled artisan will recognize that the method of purification will depend in part on the size of the DNA to be purified.

The term nucleic acid also specifically includes nucleic acids composed of bases other than the five biologically occurring bases (adenine, guanine, thymine, cytosine and uracil).

Pharmaceutical compositions comprising the present compounds are administered to an individual in need thereof by any number of routes including, but not limited to, topical, oral, intravenous, intramuscular, intra-arterial, intramedullary, intrathecal, intraventricular, transdermal, subcutaneous, intraperitoneal, intranasal, enteral, topical, sublingual, or rectal means.

The invention also encompasses the use pharmaceutical compositions of an appropriate compound, homolog, fragment, analog, or derivative thereof to practice the methods of the invention, the composition comprising at least one appropriate compound, homolog, fragment, analog, or derivative thereof and a pharmaceutically-acceptable carrier.

The invention also includes a kit comprising a compound or materials of the invention and an instructional material which describes administering the composition to a cell or a tissue of a subject, or the preparation of a structure described herein.

Other techniques useful for the practice of the present invention can be found in PCT Publication WO 03/099230, U.S. Pat. Publications 2007/0225631 (Bowlin et al.), 2007/0275458 (Gouma), 2007/0269481 (Li et al.), 2004/0058887 (Bowlin et al.), 2002/0042128 (Bowlin et al.), 2005/0095695 (Shindler), 2002/0094514 (Bowlin et al.), 2002/0081732 (Bowlin et al.), 2008/0038352 (Simpson et al.), Ma et al., 2005, Tissue Engineering, 11:101, and Stegemann et al., 2007, Tissue Engineering, 13:2601. Without further description, it is believed that one of ordinary skill in the art can, using the preceding description and the following illustrative examples, make and utilize the compounds of the present invention and practice the claimed methods.

Examples

The invention is now described with reference to the following examples. These examples are provided for the purpose of illustration only and the invention should in no way be construed as being limited to these examples, but rather should be construed to encompass any and all variations which become evident as a result of the teachings provided herein.

Methods

Electrospinning of Dye-Blend Nanofibers

The luminescent difluoroboron iodo-dibenzoylmethane dye ($BF_2dbm(I)OH$) was synthesized following previously published protocols[32]. Nanofiber meshes containing $BF_2dbm(I)(OH)$ (referred to as dye) were fabricated by blending with polylactide-coglycolide (PLAGA, Lakeshore Biomaterials in two formulations: 50:50 PLAGA ($M_w$=65 kDa, PDI=1.6) and 85:15 PLAGA ($M_w$=109 kDa, PDI=1.5)) and electrospinning. PLAGA (20% (w/v)) with the addition of 5% (w/w) of the dye were dissolved in equal parts tetrahydrofuran (THF) and dimethylformamide (DMF) (Fisher Scientific). This solution was loaded into a syringe, mounted into a programmable syringe pump (Aladdin-1000, World Precision Instruments, Sarasota, Fla.), and dispensed at a flow rate of 1 mL/hr. A driving voltage of 15 kV was supplied to an 18G needle by a high voltage power source (Gamma High Voltage Research, Ormond Beach, Fla.) across a 15 cm collecting distance to a grounded aluminum collector plate. For imaging purposes, some fibers were collected on plasma-treated glass coverslips. Control PLAGA fibers were fabricated by the same methods, with an additional 5% (w/w) PLAGA to take the place of the dye in solution.

Electrospinning PHBV/PCL Fibers

Poly(hydroxylbutyrate-co-valerate) (PHBV, PHB 95/PHV 5; Carbomer, part #80181-31-3, lot #11-SD658) and poly(caprolactone) (PCL; Sigma) were dissolved in equivalent amounts in 1:3 methanol:chloroform (Fisher Scientific) to yield an 18% weight-to-volume solution. The solution was loaded into a syringe mounted in a syringe pump (1 mL/hr) suspended above an aluminum foil collecting plate in a sealed case. The metal blunt ended syringe tip was charged to 19 kV relative to ground and placed 14 cm above the collecting plate. The fibers were dried in a lyophilizer (Labconco, Kansas City, Mo.).

Electrospinning $BF_2Dbm(I)PLA$ Fibers $BF_2dbm(I)PLA$ (synthesized according to a previously published technique[32], 13 kDa PLA) was dissolved in a solution of 10% pyridinium formate (PF; equimolar amounts of formic acid and pyridine), 20% ethanol, and 70% methylene chloride (Fisher Scientific, Waltham, Mass.) to yield a 30% weight-to-volume solution. The aluminum foil with dried PHBV/PCL fibers was used as the collecting plate for fabricating the dual-layer fibers while a clean aluminum foil sheet was used to collect only $BF_2dbm(I)PLA$ fibers. The $BF_2dbm(I)PLA$ polymer solution was loaded into a syringe as described above and displaced at 1 mL/hr. The metal syringe tip was charged to 25 kV relative to ground and placed 14.5 cm above the collecting plate. The fibers were dried in a lyophilizer.

Diameter Characterization

To image fibers, samples were mounted on ½ cm-diameter aluminum mounts. Mounted samples were gold-coated with a BAL-TEC SCD 005 Sputter Coater (BAL-TEC AG, Liechtenstein) for 210 seconds and observed under a scanning electron microscope (JEOL JSM-6400 SEM; Advanced Microscopy Facility, University of Virginia) at an accelerating voltage of 15 kV and magnification of 2000×. SEM images were acquired using ORION software to assess nanofiber morphology.

The diameters of the fibers were measured using ImageJ software available at the NIH's website. SEM images from each group were opened in ImageJ and a line was drawn across the center of the image. 50 diameter measurements were taken from nanofibers intercepting the line.

Hydrophobicity Characterization

Hydrophobicity of each nanofiber condition was quantified through contact angle measurements. A drop of deionized water was placed on top of the nanofibers for each condition. A goniometer (Rame-Hart Standard Contact Angle Goniometer, Model 200; Rame-Hart Instrument Co., Succasunna, N.J.) and DROPimage Standard software were used to measure the contact angle between the fiber and the liquid. Contact angle measurements were repeated three times for each type of nanofiber.

Strength Characterization

To characterize nanofiber strength, three samples from each nanofiber condition (except $BF_2dbm(I)PLA$) were subjected to tensile strength testing using an Instron materials testing instrument (Instron Model 5543; Instron Worldwide Headquarters, Norwood, Mass.). The BlueHill2 Program Software (version 2.14) was used to obtain force-displacement graphs for each sample. Dimensions of each sample (length, width, thickness) were measured prior to testing. The force-displacement curve data was used to calculate engineering stress and strain; stress (MPa) was calculated by dividing load (N) by cross-sectional area (width×thickness; $mm^2$) of the sample at each time point. Strain was calculated by evaluating the percent extension, or extension (mm) divided by length (mm), at each time point. Stress-strain curves were plotted for each sample. Ultimate Tensile Strength (UTS) was determined by the highest point on the stress-strain curve. Young's Modulus (E) was determined by regression fitting the linear region on the stress-strain curve and evaluating the slope. Values for E and UTS were averaged across samples for each condition. An independent means t-test was conducted to assess the strength differences between the two conditions. $BF_2dbm(I)PLA$ fibers were not subjected to strength testing due to the inability to remove fibers from collecting foil.

Ratiometric Imaging

To test the oxygen-sensing capabilities of the dual-layer fibers ($BF_2dbm(I)PLA$ fibers on PHBV/PCL fibers), a section of the fibers was cut from collecting foil. The dual-layer fibers were then peeled from the foil after soaking in EtOH and air-dried. Then the dual-layer section was taped to the bottom of a plastic, non-tissue-culture petri dish. To image the BF$_2$dbm(I)PLA fiber layer, the dual-layer fibers were exposed to UV light (395-415 nm) from a fluorescence lamp (X-Cite 120Q; Lumen Dynamics Group, Inc., Ontario, Canada). Then the fluorescence and phosphorescence modes of emission were collected with a Beta-Lactamase Filter 1 (440-480 nm) and Beta-Lactamase Filter 2 (485-515 nm) (Chroma Technology Corp; Bellows Falls, Vt.), respectively, for the same area at a constant exposure time (4.5 ms or 25 ms for boron dye side facing objective or support layer facing objective respectively) and lamp intensity level (lowest setting). Images were taken at 10× magnification on an inverted microscope (Microscope Axio Observer.A1; Carl Zeiss, Bulgaria) with an AxioCam HSM camera (Carl Zeiss). Once an area was imaged while air-exposed, nitrogen was blown into the petri dish through a pipette tip for five minutes before imaging the same area. Then, a new area was chosen and the petri dish was exposed to only air for five minutes before being imaged. This was repeated for five different areas.

To generate the ratiometric images, the separate fluorescence and phosphorescence intensity images for a single area were loaded into MATLAB. The phosphorescence-to-fluorescence intensity ratio was calculated at each pixel (pixels with zero fluorescence intensity were skipped in all calculations). To quantify the phosphorescence-to-fluorescence ratio for an entire condition (air-exposed vs. nitrogen-exposed), all five sets of fluorescence and phosphorescence images were loaded into MATLAB. The average intensity was calculated for each image, and then the phosphorescence-to-fluorescence ratio was calculated by dividing average phosphorescence by average fluorescence intensities for each field of view imaged. Finally, the five phosphorescence-to-fluorescence ratios were averaged and compared between conditions.

Standard Curves

A section of the dual-layer fibers were cut, removed from the foil, and taped to the bottom of a petri dish. Two holes were cut into opposite sides of the dish and one hole was cut into the cover. The petri dish was placed onto the stage of an inverted microscope and gas inlet and outlet hoses were attached to the holes on the side of the dish. The probe of an oxygen sensor (Oxygen Analyzer Model 600; Engineered Systems & Designs, Inc, Newark, Del.) was placed over the hole in the top of the petri dish. The gas inlet hose was connected to a mixing chamber, which was connected to an oxygen tank and a nitrogen tank. The gas outlet was connected to a flask open to the atmosphere. The entire setup is depicted in Supporting FIG. 5. The outputs of the oxygen and nitrogen tanks were adjusted such that the reading on the oxygen sensor was stable at the following oxygen concentrations: 1.0%, 2.0%, 4.0%, 8.0%, 12.0%, 16.0%, 20.0%, 25.0%, 30.0%, 40.0%, 50.0%, 60.0%, 70.0%, 80.0%, and 90.0%. When the oxygen concentration was stable, fluorescence and phosphorescence images were taken for five different spots. The imaging procedure was the same for the various conditions except that the exposure time for direct imaging of the BF$_2$dbm(I)PLA side was 31.8 milliseconds and for indirect imaging was 68.8 milliseconds. The images were then loaded into MATLAB. For each oxygen concentration and spot imaged, the average phosphorescence intensity was divided by the average fluorescence intensity to obtain the phosphorescence-to-fluorescence ratio. Then the five ratios were averaged for each oxygen concentration.

Oxygen Tension of Adherent Cells

D1 cells (ATCC, CRL-12424) were cultured in DMEM (Invitrogen, Grand Island, N.Y.) supplemented with fetal bovine serum, penicillin, and streptomycin. Sections (1 cm×1 cm) of dual-layer fibers were cut and removed from the collecting foil and placed in multi-well non-tissue culture plates (BD, Franklin Lakes, N.J.). Cells were stained with DiD and were placed on the center of the fiber section in a 10-uL droplet (5×10$^6$ cells). The well-plates were placed in the incubator for 1 hour to allow the cells to adhere to the fibers, followed by flooding with media and being placed back in the incubator. Next fiber sections were placed on glass slides and covered and sealed with a glass coverslip, which not only accelerated the time required for the cells to consume a measurable amount of the oxygen available to them, but also flattened the nanofibers so that reasonably focused images could be obtained. One spot was chosen for each section and imaged at 0, 5, 10, and 15 min after sealing. DiD, oxygen sensor fluorescence, and oxygen sensor phosphorescence images were captured at 4× magnification with a Cy5 filter, Beta-Lactamase Filter 1, and Beta-Lactamase Filter 2, respectively.

The phosphorescence-to-fluorescence ratio was calculated for each pixel. Ratio measurements along radial traces were captured using ImageJ. Five lines were drawn which radiated from the lower right corner of the images at 0, 5, 10, and 15 minutes. Data was then averaged from these 5 traces and displayed in 50 μm length bins with standard deviation to indicate the spatial variability. A two way ANOVA was used to test for significance.

Degradation Study

Sections (1 cm×1 cm) of dual-layer fibers were cut and removed from the collecting foil and placed in PBS in polycarbonate vials. The vials were incubated at 37° C. in a water bath with circular agitation for 0, 7, 14 or 21 days. After being removed from the water bath and PBS, the fibers were dried in a lyophilizer. Then, six samples from each time point were placed and sealed in glass scintillation vials with Teflon lids under nitrogen in a glove box. The emission spectrum (400-700 nm) of each sample was obtained using a UV-Vis spectrophotometer (Hewlett Packard 8452A diode-array). All emission spectra were normalized to the fluorescence peak and the six spectra from each time point were averaged together.

Gel Permeation Chromatography

Samples were dissolved in HPLC-grade tetrahydrofuran (THF), filtered through a 0.2 um filter, and loaded into vials with a septum for gel permeation chromatography analysis (GPC). Molecular weight was measured by GPC (THF, 20° C., 1.0 mL/min) against polystyrene standards on a Hewlett-Packard instrument (series 1100 HPLC) equipped with Polymer Laboratories 5 μm mixed-C columns and connected to a refractive index (Viscotek LR 40) detector. Data were processed with the OmniSEC software (version 4.2, Viscotek Corp).

Pancreatic Islet Isolation

Pancreatic islets were isolated from C57BL/6 mice (Jackson Laboratories, Bar Harbor, Me.) that were sacrificed immediately prior to the procedure. After confirmation of euthanasia, a lateral incision exposed the peritoneal cavity and two lobes of the liver were placed onto sterile gauze over the animal's ribcage. The common bile duct was occluded by tying off with suture at the entrance to the intestine and was cannulated with a 30G needle for injection of 2-3 mL of 1.4 mg/mL collagenase P (Roche) dissolved in Hank's Balanced Salt Solution (HBSS, Thermo Scientific) supplemented with 10 mg/L heat treated bovine serum albumin and 0.35 g/L sodium bicarbonate (supplemented HBSS). The pancreas was carefully removed from the animal after distension and placed in 1 mL of supplemented HBSS on ice to which 4 mL of enzyme solution was added in individual 15 mL centrifuge tubes for each mouse. Incubation in a 37° C. water bath (15 min was selected with this batch of enzyme) was followed by vigorous shaking by hand to disrupt tissue structure. Next, the tubes were placed immediately on ice and the balance of the 15 mL was filled with supplemented HBSS. Two washes in supplemented HBSS were followed by a filtering through a steel mesh and density separation with Histopaque 1077 (Sigma #10771). Two more washes and a wash in fully supplemented culture media (RPMI 1640+10% FBS, 2% Penicillin Streptomycin+ 2.5% 1×HEPES) completed the isolation. The islets were placed onto ice in 50 mL tubes containing 10 mL of media and transported to another building for the in vivo experiment 4 h after isolation completion.

Dorsal Skinfold Window Chamber Experiments

All surgeries were performed according to a protocol approved by the Institutional Animal Care Committee at the University of Virginia. Eighteen C57BL/6 mice (Jackson Laboratories, Bar Harbor, Me.) were used. Anesthesia was induced with isoflurane gas (2-3%) and the surgical plane was maintained throughout the procedure with a nose cone (1-2%) equipped with a scavenging apparatus. Briefly, dorsal skin was attached to a corkboard with 26 gauge needles and the top layer of skin corresponding with the window portion of the chamber (10 mm diameter) was removed to expose the cutaneous microcirculation of the panniculus carnosus. Ringer's solution was added throughout the process to keep the area hydrated. The top titanium chamber was secured with sutures and the screws were tightened to hold the chamber together. Ringer's solution was used to fill the cavity before implanting two 6 mm diameter nanofiber scaffold hemispheres and applying the glass coverslip. Postoperative bupronex was administered to the animals every 12 h for 48 h.

Microscopy color CCD images (Nikon, Melville, N.Y.) were taken on Days 0, 1, 2, 7, and 14 after surgery using unfiltered brightfield light or UV excitation with a color CCD camera mounted on a stereomicroscope. Excitation was from a handheld UV lamp.

For the two weeks following implants, the entire window chamber was imaged and the implant area was manually cropped and quantified to produce a mean value for each of eight mice, bars show standard error of the mean. Cold type 1 rat tail collagen (Becton-Dickinson), with or without islets, was placed on the exposed tissue and nanofibers at t=0 min. At two weeks a transient ischemia in 3 separate mice was created by placing clamps on the skin which is tented up outside the two pieces of the dorsal skinfold window chamber at t=0 min. These mice had fibers collected on the coverslip that closes the window chamber rather than the dual layer fiber scaffold. Exposure time was 1 ms for the color images.

In Vivo Image Analysis

Because no filters were used during the in vivo experiments, the two sensor emissions were distinguished solely on the basis of the green (phosphorescence) and blue (fluorescence) channels of color images. The basic image reading and ratio calculations that were used for the in vitro experiments were used for the in vivo experiments, with the exception being that it was channels of a single color image rather than two separate grayscale images as the inputs. For quantification, areas of the images that did not include sensor nanofibers were excluded from the analysis. Pixels that had an undefined ratio (due to a lack of fluorescence) were also excluded from the analysis. To correct for reductions in phosphorescence intensity due to degradation of the fibers in aqueous environments, a time-dependent scaling factor was applied to all data collected after day 0. Scaling factor was determined based on the change in the max intensity phosphorescence signal over time from the in vitro degradation and spectral analysis (FIG. 4b). Curve fitting to the degradation data provides scaling factors specific to each time point.

In addition, a correction factor was applied to all images where the glass was present during imaging (1.56 for all time points with glass cover slip applied). The glass correction factor was determined by imaging unused fibers, laying a glass coverslip over the fibers and immediately imaging a second time. When the glass covered image average was multiplied by the glass correction factor of 1.56 (s.d. 0.06, n=4) the measured ratio was increased back to that found without the glass covering the area. In this way all in vivo ratio values were scaled to be comparable to Day 0 values without the glass coverslip over the window chamber.

Statistics

The student's t-test or two way ANOVA are used for determining significance at a $p<0.05$.

Results and Discussion

PLAGA and Boron Dye Blend Nanofibers

While biodegradable electrospun polymer nanofibers have been characterized in the literature,[38] the performance of the boron dye when blended with PLAGA or conjugated to a polymer in a nanofiber scaffold had not been investigated. The oxygen sensitive dye was first blended with the aqueous degradable 50:50 PLAGA (lactic:glycolic subunits) formulation to make electrospun nanofibers. Oxygen sensing capability was assessed after incubation in phosphate buffered saline (PBS) filled microtubes at 37° C. in a shaking water bath, by comparing phosphorescence and fluorescence signals (peaks at 525 and 450 nm respectively). The 50:50 PLAGA dye blend nanofiber scaffold exhibited a reduced oxygen sensing ability after a week which could be a result of polymer degradation (FIG. 1A).[39] To address this issue, we hypothesized that replacing the 50:50 PLAGA with the slower degrading 85:15 PLAGA would protect the oxygen sensing ability of the dye in the electrospun nanofiber scaffold over time.[40] Gel-permeation chromatography was conducted after one, two, or three weeks of incubation in PBS by lyophilizing the sample which could then be dissolved in an organic solvent. In comparison to the 50:50 ratio, the 85:15 ratio indeed degraded more slowly and the addition of the dye had little effect on polymer chain shortening (Table S1). The microstructure of the 85:15 scaffolds was maintained following incubation in aqueous media for 14 days (FIG. 1B and Supporting FIG. 2A-G). Shifts in the room temperature phosphorescence peak suggest changes in the dye microenvironment. We observed the phosphorescence peak blue-shifted twice as much in the 50:50 co-polymer ratio compared to the 85:15 co-polymer ratio (Table S2, Supporting FIG. 1A-C), suggesting better preservation of dye microenvironment with the slower degrading polymer. Despite the slower degradation properties of 85:15 PLAGA, the scaffold phosphorescence peak was weak in comparison to the fluorescence peak after fabrication (Day 0) and after weeks of in vitro aqueous exposure (FIG. 1C), which reduces the utility of the scaffold for ratiometric imaging in tissue engineering applications. Therefore, the boron dye polymer blend scaffolds were not investigated further in this study.

Supporting Table 1: 85:15 PLGA degraded slower without an observed effect of the addition of dye.

| | 50:50 PLGA | | | | 85:15 PLGA | | | |
|---|---|---|---|---|---|---|---|---|
| | unloaded | | dye-loaded | | unloaded | | dye-loaded | |
| Day | $M_n$ | PDI | $M_n$ | PDI | $M_n$ | PDI | $M_n$ | PDI |
| 0 | 25000 | 1.85 | 25000 | 1.80 | 32000 | 1.86 | 37000 | 1.54 |
| 7 | 21000 | 1.96 | 24000 | 1.83 | 37000 | 1.95 | 38000 | 1.84 |
| 14 | 15000 | 2.29 | 16000 | 2.09 | 32000 | 1.93 | 41000 | 1.87 |
| 21 | 14000 | 1.85 | 15000 | 1.77 | 34000 | 1.73 | 33000 | 1.60 |

SUPPORTING TABLE 2

85:15 PLGA reduced the blue shift of the phosphorescent peak.

| | 50:50 PLGA | | 85:15 PLGA | |
|---|---|---|---|---|
| Day | $l_{RTP}$ (nm) | $t_{RTP/x2}$ (ms) | $l_{RTP}$ (nm) | $t_{RTP/x2}$ (ms) |
| 0 | 531 | 4.68 ms/1.32 | 525 | 4.16 ms/1.25 |
| 7 | 522 | 5.12 ms/1.08 | 520 | 3.24 ms/1.04 |
| 14 | 520 | 5.13 ms/1.10 | 520 | 3.11 ms/1.11 |

Dual Layer Scaffold Construction for Tissue Engineering

In the blended PLAGA and dye nanofibers, diffusion of the dye in the polymer matrix and enhanced dye degradation by hydrolysis may contribute to the loss of scaffold oxygen sensing function over time in aqueous media. To reduce diffusional loss of dye to the surrounding aqueous media and to preserve sensor function, a form of the dye that is chemically conjugated to a PLA polymer[41] replaced the physical mixture of dye and polymer for scaffold fabrication. The PLA-conjugated boron dye selected for this study, which had been synthesized previously,[42] has a relatively low molecular weight for electrospinning (13 kDa) requiring extra parameter adjustment to produce fibers of consistent morphology. Optimization of the electrospinning process yielded final parameters of 30% (w/v) dye-polymer in 10% (v/v) pyridinium formate, 20% (v/v) ethanol, in dichloromethane at a 25 kV applied voltage, 14.5 cm working distance, and 1 mL/hr solution flow rate applied to the 13 kDa PLA alone and the boron dye-polymer conjugate (Supporting FIG. 3A-G).

The dye-polymer conjugate (BF2dbm(I)PLA) nanofiber mat was fragile in handling for experiments. It was therefore necessary to reinforce the mat with a structural support layer. Blended poly(3-hydroxybutyrate-co-3-hydroxyvalerate) and polycaprolactone (PHBV and PCL) nanofibers were employed (Supporting FIG. 3A-G) as the structural layer to create a dual layer tissue engineering scaffold. The boron dye nanofibers were electrospun onto the dry PHBV and PCL nanofibers attached to the grounded collector plate (Supporting FIG. 3A-G), allowing for the simultaneous removal and handling of the supporting and sensing nanofiber layers.

Figure 2A:
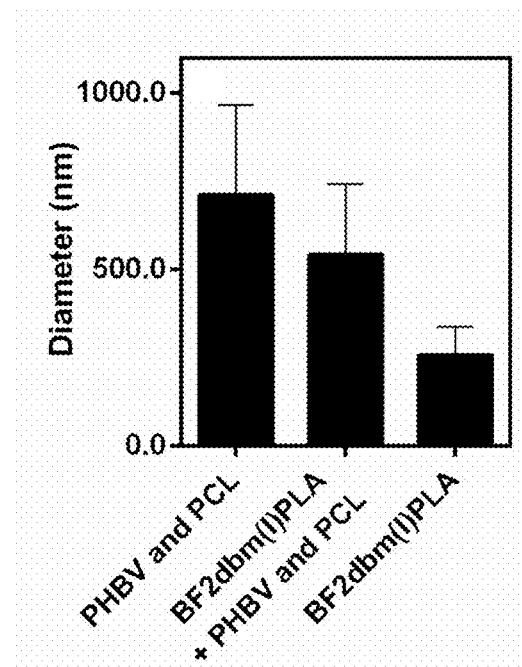
Figure 2B:
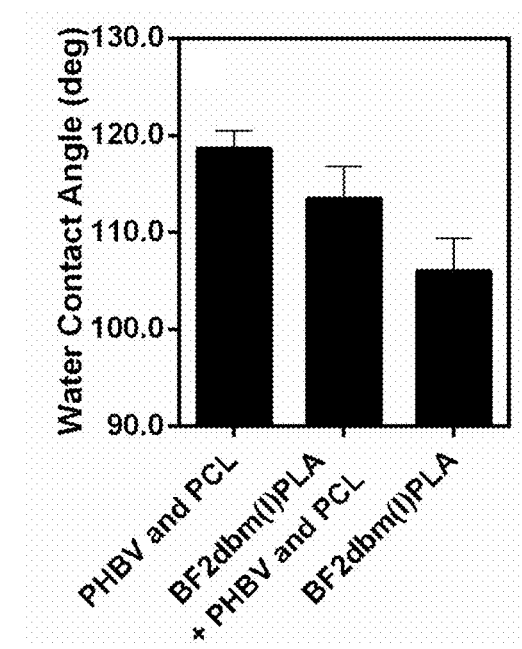

The dual layer scaffold had an intermediate nanofiber diameter between the mean diameter of the support layer or the dye layer alone (FIG. 2A). The water contact angle of the dye layer was significantly lower than the support layer and the dual layer scaffold had an intermediate value between either individual layer (FIG. 2B-E). Fluorescence confocal microscopy of the surface of the dual layer scaffold demonstrate both layers have surface exposure as evidenced by only partial surface coverage of green (dye) over the red (PHBV and PCL) fluorescence (FIG. 2F). Therefore, cells growing on the scaffold are expected to experience the material properties of both layers.

Figure 2G:
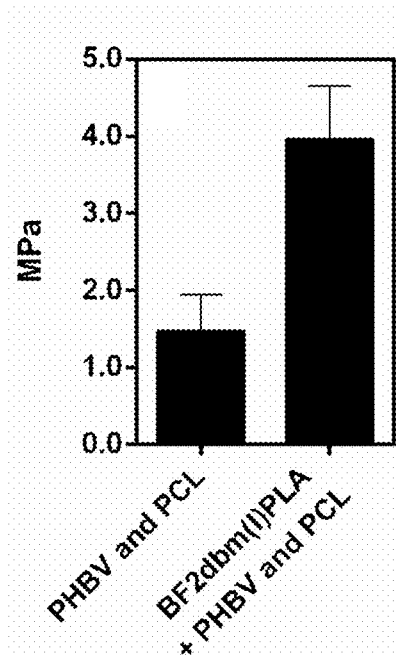
Figure 2H:
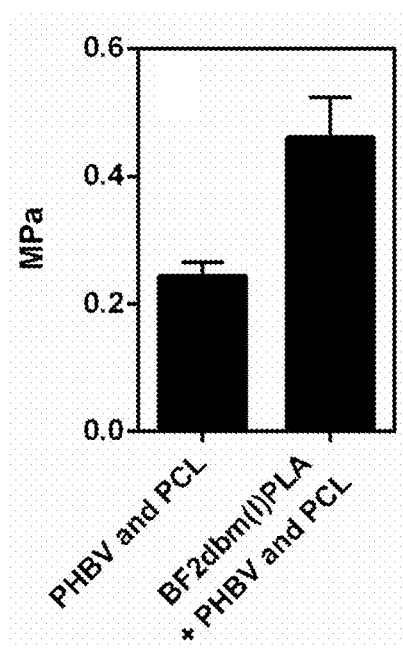

The Young's Modulus of the nanofiber substrate can affect the phenotype of cells cultured on the material.[43-45] To test the tensile properties of the dye nanofiber mat, we compared the dual layer scaffold to the PHBV and PCL support layer alone. The Young's Modulus of the dual layer scaffold was greater than the support layer alone (FIG. 2G). Cells that are grown on the dual layer scaffold are therefore expected to experience two stiffnesses. Tissue engineering applications exert various forces on scaffolds including tensile loads. The addition of the dye layer caused the ultimate tensile strength to be slightly greater than the PHBV and PCL scaffold alone (FIG. 2H). The inability to handle the dye fibers alone then may result from the thin nature of the layer and perhaps bending forces applied during peeling rather than a lack of strength of the material. Being attached to a thicker, lower Young's Modulus layer endows the ability to handle the dye scaffold and gives two cell substrates to the scaffold.

To test whether the dye can register changes in oxygen levels in different environments, ratiometric imaging was conducted in dry atmosphere (FIG. 3A-B) or PBS (FIG. 3C). The scaffold was exposed to an oxygen rich or oxygen poor environment with the dye side imaged directly (FIG. 3A,C) or through the support layer (FIG. 3B). The increase from an oxygen rich P/F ratio to oxygen poor P/F ratio was still detected when imaging through the dual layer scaffold, confirming that the scaffold can be used in either orientation if the changes in ratio are all that is desired. Further, similar ratios were measured when the scaffold was submersed in PBS (FIG. 3C), confirming signal generation in a hydrated environment. Fiber morphology is obscured when imaging through the support layer, therefore in the validation experiments the dye side is imaged directly to ensure that the best possible spatial resolution was obtained.

Performance Stability of Boron Dye Conjugate Nanofibers

In order to understand the effects of long term exposure to aqueous media which is critical to cell culture and in vivo applications, the spectral response of the polymer-dye conjugated dual layer scaffold was measured after 0, 7, 14 and 21 days of incubation in PBS at physiological temperature. The intensity of the phosphorescence peak of the chemically conjugated fiber scaffold decreased with increasing aqueous media exposure time when normalized to the fluorescence peak (FIG. 4A) following an exponential decay (FIG. 4B). The phosphorescence peak (525 nm) of the polymer conjugate fibers was distinct compared to the dye polymer blend 85:15 PLAGA nanofibers (FIG. 1C) after aqueous media exposure and did not see the same decrease during the first 7 days as the 50:50 PLAGA blend fibers (FIG. 1A). This trend is expected based on known dye loading effects; gradual dye degradation in aqueous environments corresponds to lower dye to polymer loading and a decreased P/F ratio.[46] Scanning electron microscopy imaging showed that the slowly degrading support layer of the dual layer scaffold maintained consistent morphology over the three weeks and that the dye layer fibers swelled with time in aqueous media (FIG. 4C-J). Unlike the blended dye polymer fibers, the phosphorescence peak of the conjugated dye-polymer fibers was more distinct from the low wavelength fluorescence signal (450 nm). Partial dye and polymer degradation did occur during the 21 day aqueous incubation, however the peaks were still detectable in the dye-conjugate system (FIG. 4A). In order to correct for reductions in phosphorescence intensity due to degradation of the fibers in aqueous environments, a time-dependent scaling factor was applied to all data collected after day 0. The scaling factors were empirically defined from the degradation of the spectral signal after incubation of the dye in aqueous media for given durations of time (FIG. 4A,B).

Figure 5A:
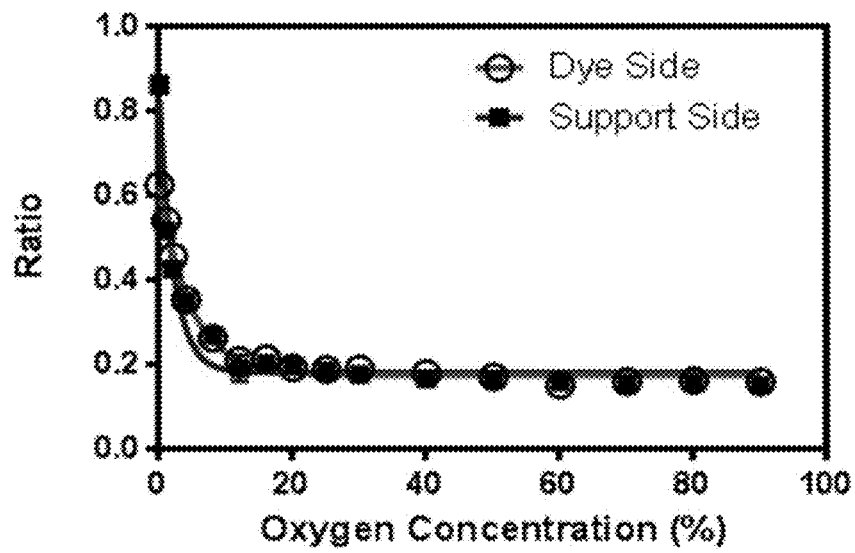
FIG. 5A-D. The calibration of the boron dye fibers is not affected by imaging through the support layer (FIG. 5A). Standard curves in the presence of aqueous media including PBS (FIG. 5B) or DMEM (FIG. 5C) or DMEM+FBS (FIG. 5D) demonstrate function in physiological media. Oxygen concentration measured by percent for dry gas and parts per million (PPM) for aqueous conditions.
Figure 5B:
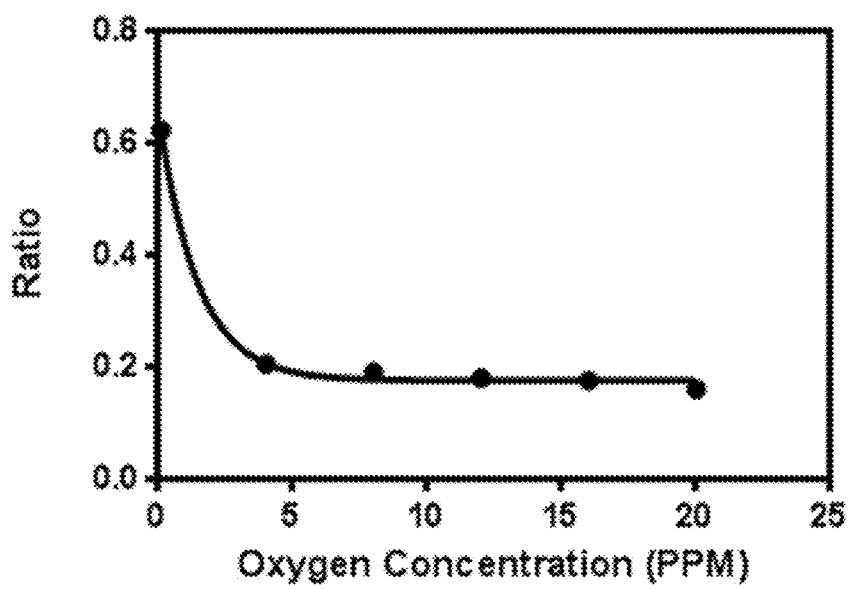
Figure 5C:
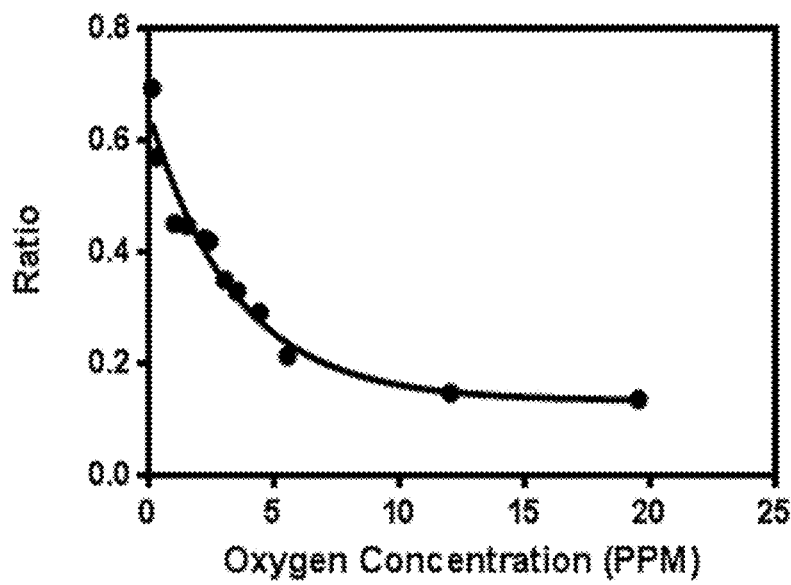
Figure 5D:
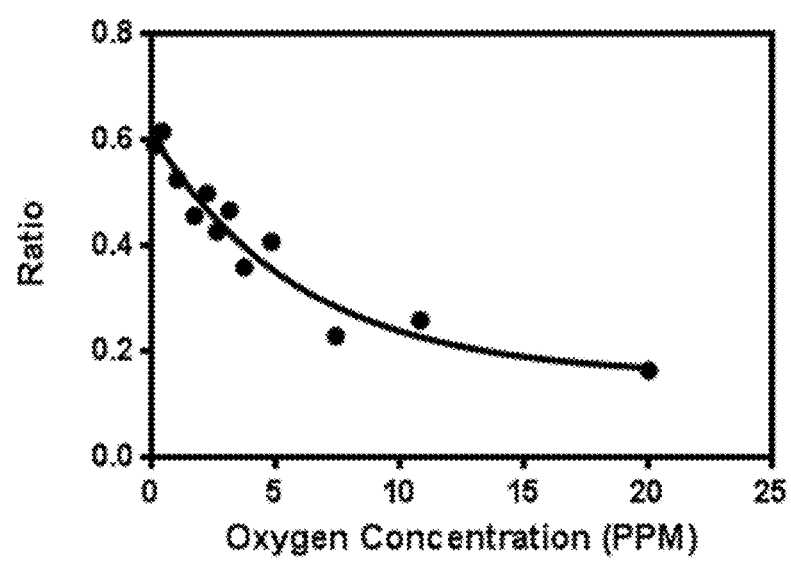

Controlled low oxygen conditions help sensitive cells, such as stem cells, maintain their native phenotype longer in culture[47,48] or enhance differentiation in vitro.[49,50] In order to utilize the boron dye dual layer scaffold to detect hypoxia, the dependence of the P/F ratio on the oxygen tension was explored. The ability to measure oxygen, rather than simply sense a low oxygen condition, is desired since different cell types initiate hypoxic signaling at differing levels of oxygen.[51,52] Standard curves that relate the measured P/F ratio to known oxygen concentrations were constructed in dry and aqueous environments. The shape of the standard curves was similar regardless of whether data collection was performed directly at the sensor layer, through the support layer or in PBS (FIG. 5A,B). Ratiometric readings were shifted in standard cell culture media (Dulbecco's Modified Eagle Medium, DMEM) compared to PBS (FIG. 5C) likely due to the presence of phenol red, which has broad spectrum absorption, or may also be attributed in part to solvatochromism from the additional inorganic components that are not in PBS. The addition of fetal bovine serum (FBS) (FIG. 5D) to DMEM demonstrates that biological entities (proteins, growth factors, etc.) do not change the curve shape, suggesting that the enhanced sensitivity below 10 ppm may be similar across tissue types and is attributable to the sensor material properties. Therefore, the hypoxia sensing scaffold signal would behave the same regardless of the tissue since the physiological conditions (salinity, pH) are similar across tissue types while differing protein content does not affect the signal.

Spatiotemporal Oxygen Variations in Cell Culture

To ensure that the dye sensor response is rapid enough in living systems, a moving stream of low oxygen gas was passed over dry fibers. The fibers in the nitrogen stream both activated (increased P/F ratio) and returned to baseline very quickly suggesting that the fibers could measure dynamic changes in local oxygen (data not shown). Biocompatibility of the nanofiber constructs was tested by culturing adherent NIH3T3 cells on the dye nanofiber layer. Tests showed no evidence of cytotoxicity as the majority of cells stained viable by fluorescein diacetate (FDA) (FIG. 6A,C) and were not stained by propidium iodide (PI) (FIG. 6B,C).

In vitro validation was conducted by seeding membrane stained D1 cells (adherent mouse bone marrow stem cell line) onto the scaffold. High-density layers of cells in culture are expected to consume oxygen in their local environment and therefore should create a scaffold level oxygen gradient. A corresponding spatial change in the P/F reading of the boron dye nanofiber scaffold with increased time in a closed environment would be expected. A cellular membrane stain was used to visualize the area of the nanofiber mat covered by cells (FIG. 6D). The nanofiber scaffold with cells attached was mounted on a glass slide and sealed from the environment with a cover slip immediately prior to imaging to provide a barrier to diffusion of oxygen from the atmosphere. In the absence of this diffusion barrier, the P/F ratio did not change over time (data not shown). At time 0, lower P/F ratio (greater scaffold oxygen levels) were detected farthest away from the central cell mass (FIG. 6F, blue line) and the P/F ratio increased (oxygen levels decreased) over time in the areas adjacent to the cells. As time increased from 0 to 15 minutes the area experiencing higher P/F ratio (lower oxygen) grew outward from the center of the adherent cells (FIG. 6D-F). Non-uniform cell distribution upon the scaffold produces substantial variation in measurements and therefore measurements were binned by radial distance intervals of 50 um to make comparisons between time and distance from the center of the cell-covered region (Supplementary FIG. 4A). Oxygen depletion is significant at 5 and 15 minutes from 50 to 300 um. These data provide a biological proof of concept with spatial and temporal scaffold level variations observed.

Re-Oxygenation of Tissue after Injury

Figure 7A:
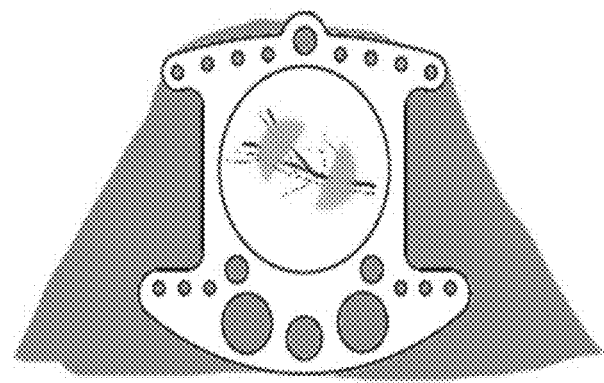
FIG. 7A-E. Oxygenation varied with time (FIG. 7B-C) following implant of the dorsal skinfold window chamber (FIG. 7A, standard error of the mean shown, n=8, *indicates p<0.05 by student's t-test verses days 0 thru 2). Nanofibers show temporal variation in oxygen tension in transient in vivo ischemia (FIG. 7D and FIG. 7E experiment conducted at two weeks window chamber implant duration with a large thin polymer conjugate dye layer only scaffold, n=3).
Figure 7B:
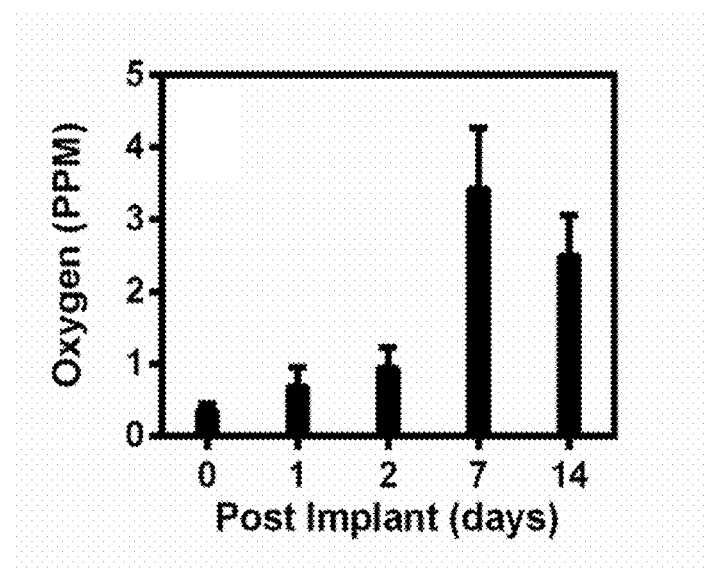
Figure 7C:
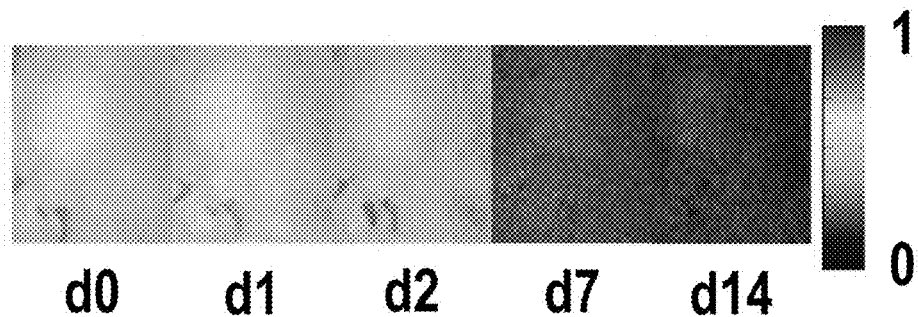
Figure 7D:
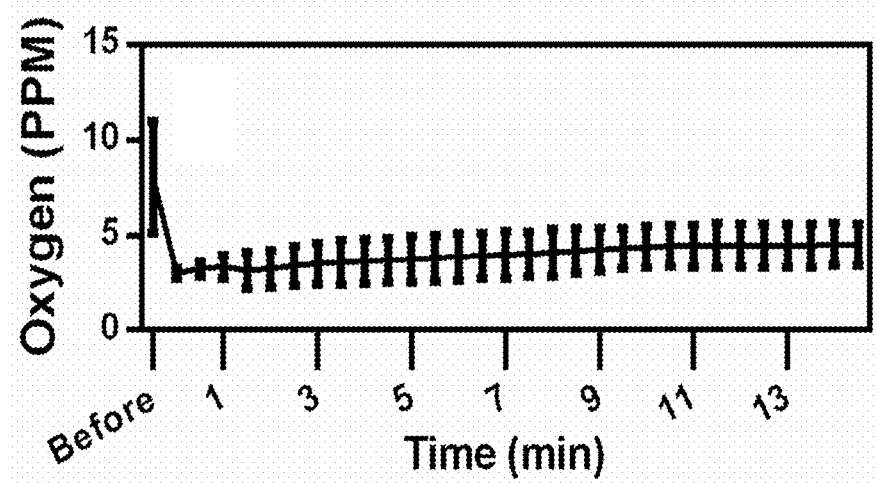
Figure 7E:
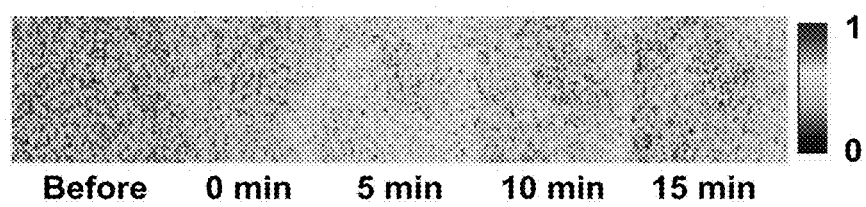

The dorsal skinfold window chamber (FIG. 7A) was selected for in vivo validation as it provides a planar tissue surface that lends itself to intra-vital microscopy. The oxygen sensor scaffold was implanted and monitored in the window chamber for 14 days. The measured oxygen tension increased up to day 7 as the tissue recovered from the surgical procedure (FIG. 7B,C) and oxygen gradients could be sensed in proximity to blood vessels (Supplementary FIG. 4B,C). Tissue oxygenation following ischemia initiated at t=0 min initially decreased and then remained reduced (FIG. 7D,E), showing the scaffold is tuned to a relevant range of dissolved oxygen in vivo.

Oxygenation of Islet Implants In Vivo

Figure 8A:
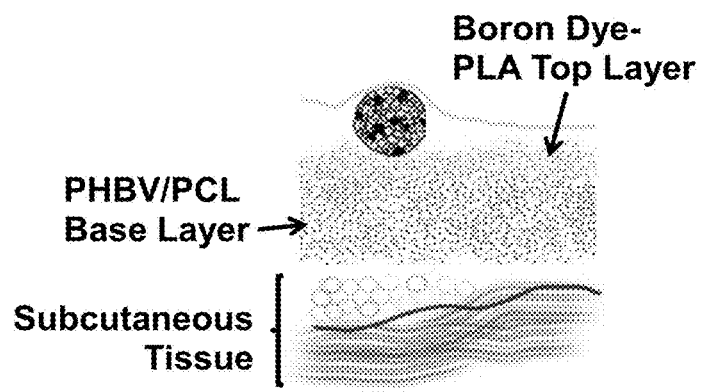
FIG. 8A-C. Testing Pancreatic Islets In Vivo. Pancreatic islets were placed on top of nanofibers in a gel in the dorsal skinfold window chamber (FIG. 8A, cross-section schematic). A slightly reduced oxygen tension at steady state when islets were present in the gel was observed compared to the cell devoid gels (FIG. 8B, n=3 for each group, conducted on different days with correction to account for differing dye performance, p>0.05). Representative ratiometric images (higher ratio indicates lower oxygen) of mice from each group are shown (FIG. 8C). Hypoxia developed quickly following replacement of glass coverslip.
Figure 8B:
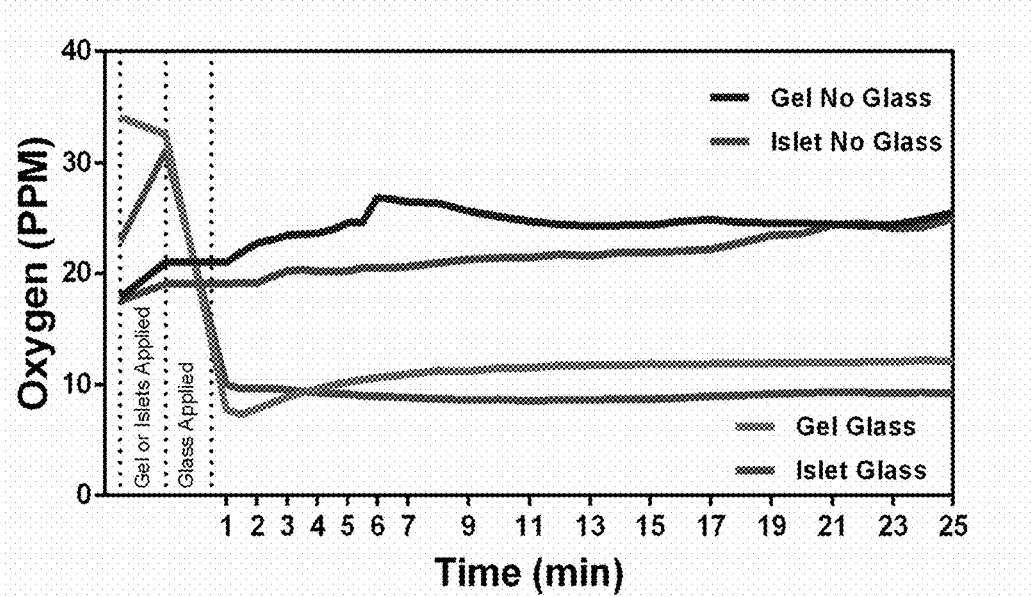
Figure 8C:
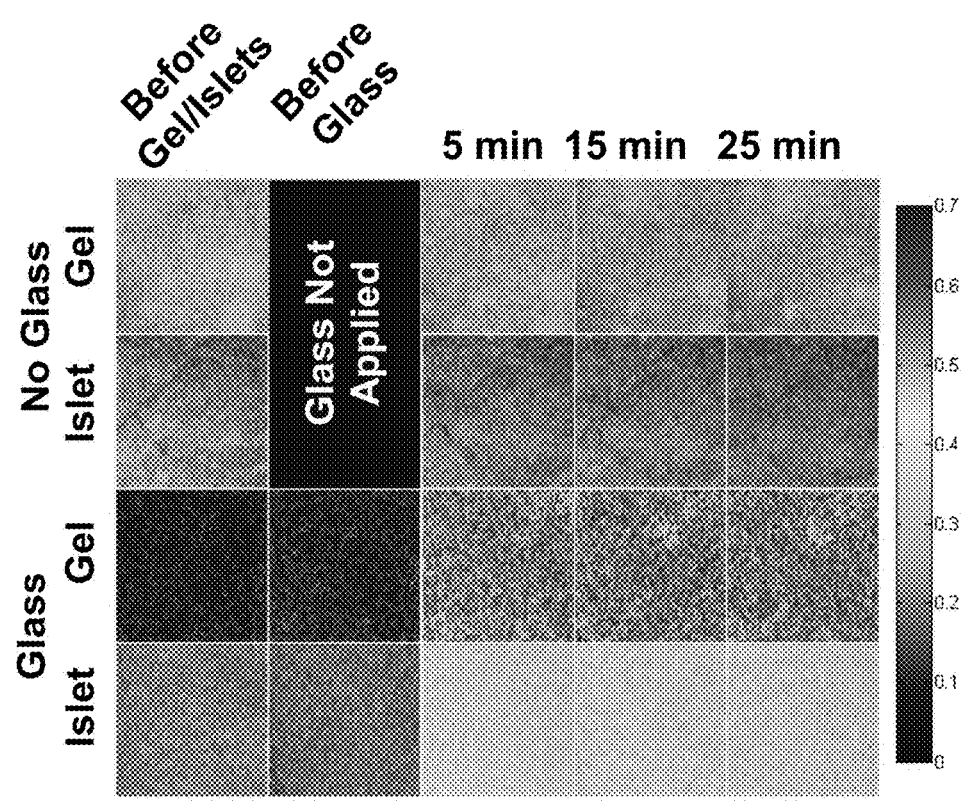
Figure 9A:
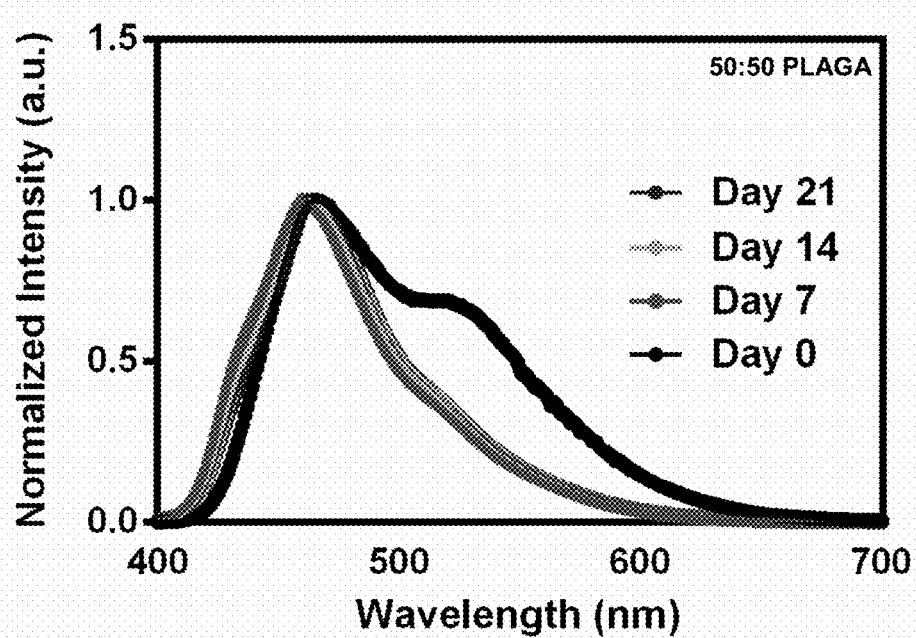
Figure 9B:
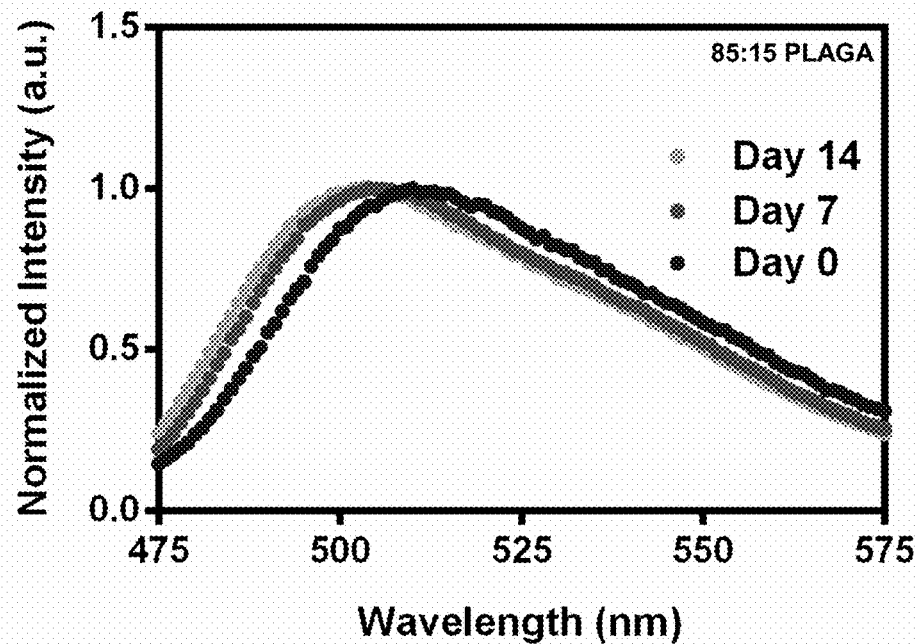
Figure 13:
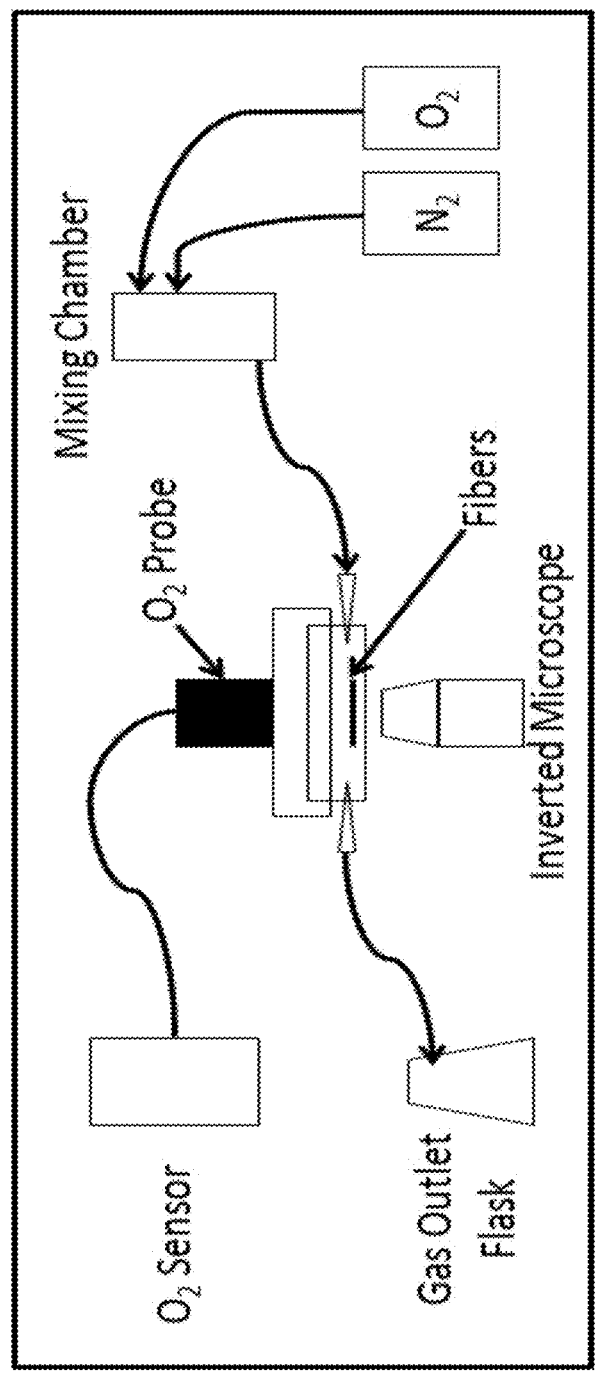

Pancreatic islets are known to suffer from hypoxia due to their avascular multicellular spheroid shape.[53-56] To test the ability of the boron dye-conjugate nanofibers to detect acute changes in oxygenation of implanted islets, syngeneic pancreatic islets were isolated and directly transferred in a type 1 collagen gel onto the dual layer scaffold in the window chamber (FIG. 8A). The P/F ratio demonstrates that lowest oxygen level developed between seven and ten minutes following the delivery of the islets (FIG. 8B-C). As in the in vitro cell experiments, the use of glass to seal the tissue compartment from contact with the open air was critical to see the effect of islet oxygen consumption to the end of the experiment. In both cases, the islet containing gel was slightly more hypoxic than the acellular collagen gel. Based on these results, it is concluded that the dye-polymer conjugated fibers are well suited to a range of oxygen concentrations that arise in cell culture and in vivo models where hypoxia occurs.

CONCLUSION

Tissue engineering techniques have the potential to stimulate regeneration of damaged or diseased tissues; however, a major challenge is preventing cell death within thick constructs due to low oxygen tension. Although it is possible to study oxygen gradients in constructs or tissues using insertion of probes,[57] this disturbs the organization of growing cells and impedes the goal of monitoring scaffold cell interactions.[58] Scaffold based oxygen sensing is investigated here with a boron dye that emits a phosphorescence and fluorescence signal whose ratio changes with oxygen concentration, to overcome this drawback for construct study. Importantly, the nanofiber morphology, obtained with careful parameter adjustments for the low molecular weight polymer, is an excellent substrate for cell attachment and growth. Cells attached to the scaffold in vitro cause spatial increases in the sensor output, suggesting oxygen tension variation on the millimeter scale as time increases. The first 2-3 weeks after a tissue engineering scaffold is implanted are crucial for successful implant integration, including vascularization. We showed increases in oxygenation as the tissue healed following dorsal skinfold chamber placement, with measurements out to 14 days. In conclusion, we have shown that this oxygen-sensing scaffold is a platform for scientific investigation of changes in oxygenation within regenerative tissue engineering scaffolds and for use in monitoring diseased tissue and tissue transplants.

The disclosures of each and every patent, patent application, and publication cited herein are hereby incorporated by reference herein in their entirety.

Headings are included herein for reference and to aid in locating certain sections. These headings are not intended to limit the scope of the concepts described therein under, and these concepts may have applicability in other sections throughout the entire specification.

While this invention has been disclosed with reference to specific embodiments, it is apparent that other embodiments and variations of this invention may be devised by others skilled in the art without departing from the true spirit and scope of the invention.

BIBLIOGRAPHY

1. Semenza, G. L. Oxygen Sensing, Homeostasis, and Disease. N. Engl. J. Med. 2011, 365, 537-547.
2. Franke, K.; Gassmann, M.; Wielockx, B. Erythrocytosis: The HIF Pathway in Control. Blood 2013, 122, 1122-1128.
3. Pietrocola, F.; Izzo, V.; Niso-Santano, M.; Vacchelli, E.; Galluzzi, L.; Maiuri, M. C.; Kroemer, G. Regulation of Autophagy by Stress-Responsive Transcription Factors. Semin. Cancer Biol. 2013, 23, 310-322.
4. Ratcliffe, P. J. Oxygen Sensing and Hypoxia Signalling Pathways in Animals: The Implications of Physiology for Cancer. J. Physiol. (Oxford, U. K.) 2013, 591, 2027-2042.
5. Escribese, M. M.; Casas, M.; Corbi, A. L. Influence of Low Oxygen Tensions on Macrophage Polarization. Immunobiology 2012, 217, 1233-1240.
6. Phelps, E. A.; Garcia, A. J. Engineering More Than a Cell: Vascularization Strategies in Tissue Engineering. Curr. Opin. Biotechnol. 2010, 21, 704-709.
7. Kannan, R. Y.; Salacinski, H. J.; Sales, K.; Butler, P.; Seifalian, A. M. The Roles of Tissue Engineering and Vascularisation in the Development of Micro-Vascular Networks: a Review. Biomaterials 2005, 26, 1857-1875.
8. Xu, H.; Aylott, J. W.; Kopelman, R.; Miller, T. J.; Philbert, M. A. A Real-Time Ratiometric Method for the Determination of Molecular Oxygen Inside Living Cells Using Sol-Gel-Based Spherical Optical Nanosensors with Applications to Rat C6 Glioma. Anal. Chem. 2001, 73, 4124-4133.
9. Koo, Y.-E. L.; Cao, Y.; Kopelman, R.; Koo, S. M.; Brasuel, M.; Philbert, M. A. Real-Time Measurements of Dissolved Oxygen Inside Live Cells by Organically Modified Silicate Fluorescent Nanosensors. Anal. Chem. 2004, 76, 2498-2505.
10. Pfister, A.; Zhang, G.; Zareno, J.; Horwitz, A. F.; Fraser, C. L. Boron Polylactide Nanoparticles Exhibiting Fluorescence and Phosphorescence in Aqueous Medium. ACS Nano 2008, 2, 1252-1258.
11. Kersey, F. R.; Zhang, G.; Palmer, G. M.; Dewhirst, M. W.; Fraser, C. L. Stereocomplexed Poly(lactic Acid)-Poly (ethylene Glycol) Nanoparticles with Dual-Emissive Boron Dyes for Tumor Accumulation. ACS Nano 2010, 4, 4989-4996.
12. Mosinger, J.; Lang, K.; Plistil, L.; Jesenská, S.; Hostomský, J.; Zelinger, Z.; Kubát, P. Fluorescent Polyurethane Nanofabrics: a Source of Singlet Oxygen and Oxygen Sensing. Langmuir 2010, 26, 10050-10056.
13. Songzhu, L.; Xiangting, D.; Jinxian, W.; Guixia, L.; Wenshen, Y.; Ruokun, J. Fabrication of Eu(III) Complex Doped Nanofibrous Membranes and Their Oxygen-Sensing Properties. Spectrochim. Acta, Part A 2010, 77, 885-889.
14. Wen, C.; Tao, G.; Xu, X.; Feng, X.; Luo, R. A Phosphorescent Copper(I) Complex: Synthesis, Characterization, Photophysical Property, and Oxygen-Sensing Behavior. Spectrochim. Acta, Part A 2011, 79, 1345-1351.
15. Zhang, H.; Lei, B.; Dong, H.; Liu, Y. Oxygen Sensing Properties of Cu(I) Complex/Polystyrene Composite Nanofibers Prepared by Electrospinning. J. Nanosci. Nanotechnol. 2011, 11, 9840-9845.
16. Hong, H.; Zhu, L.; Wang, A.; Lu, H. Re(I) Complex Doped Nanofibers for Oxygen Optical Sensing. Spectrochim. Acta, Part A 2012, 98, 466-473.
17. Xue, R.; Behera, P.; Viapiano, M. S.; Lannutti, J. J. Rapid Response Oxygen-Sensing Nanofibers. Mater. Sci. Eng., C 2013, 33, 3450-3457.
18. Dahlin, R. L.; Kasper, F. K.; Mikos, A. G. Polymeric Nanofibers in Tissue Engineering. Tissue Engineering, Part B: Reviews 2011, 17, 349-364.
19. Ren, Y.-J.; Zhang, S.; Mi, R.; Liu, Q.; Zeng, X.; Rao, M.; Hoke, A.; Mao, H.-Q. Enhanced Differentiation of Human Neural Crest Stem Cells Towards the Schwann Cell Lineage by Aligned Electrospun Fiber Matrix. Acta Biomater. 2013, 9, 7727-7736.
20. Mukhatyar, V. J.; Salmerón-Sánchez, M.; Rudra, S.; Mukhopadaya, S.; Barker, T. H.; Garcia, A. J.; Bellamkonda, R. V Role of Fibronectin in Topographical Guidance of Neurite Extension on Electrospun Fibers. Biomaterials 2011, 32, 3958-3968.
21. Lee, S.; Leach, M. K.; Redmond, S. A.; Chong, S. Y. C.; Mellon, S. H.; Tuck, S. J.; Feng, Z.-Q.; Corey, J. M.; Chan, J. R. A Culture System to Study Oligodendrocyte Myelination Processes Using Engineered Nanofibers. Nat. Methods 2012, 9, 917-922.
22. Silva, G. A.; Czeisler, C.; Niece, K. L.; Beniash, E.; Harrington, D. A.; Kessler, J. A.; Stupp, S. I. Selective Differentiation of Neural Progenitor Cells by High-Epitope Density Nanofibers. Science (Washington, D.C., U. S.) 2004, 303, 1352-1355.
23. Xie, J.; Willerth, S. M.; Li, X.; Macewan, M. R.; Rader, A.; Sakiyama-Elbert, S. E.; Xia, Y. The Differentiation of Embryonic Stem Cells Seeded on Electrospun Nanofibers into Neural Lineages. Biomaterials 2009, 30, 354-362.
24. Neal, R. A.; Tholpady, S. S.; Foley, P. L.; Swami, N.; Ogle, R. C.; Botchwey, E. A. Alignment and Composition of Laminin-Polycaprolactone Nanofiber Blends Enhance Peripheral Nerve Regeneration. J. Biomed. Mater. Res., Part A 2011, 100A, 406-423.
25. Hsiao, C.-W.; Bai, M.-Y.; Chang, Y.; Chung, M.-F.; Lee, T.-Y.; Wu, C.-T.; Maiti, B.; Liao, Z.-X.; Li, R.-K.; Sung, H.-W. Electrical Coupling of Isolated Cardiomyocyte Clusters Grown on Aligned Conductive Nanofibrous Meshes for Their Synchronized Beating. Biomaterials 2013, 34, 1063-1072.
26. Yeo, M.; Lee, H.; Kim, G. Three-Dimensional Hierarchical Composite Scaffolds Consisting of Polycaprolactone, β-Tricalcium Phosphate, and Collagen Nanofibers: Fabrication, Physical Properties, and in Vitro Cell Activity for Bone Tissue Regeneration. Biomacromolecules 2011, 12, 502-510.
27. Kumbar, S. G.; Nukavarapu, S. P.; James, R.; Nair, L. S.; Laurencin, C. T. Electrospun Poly(lactic Acid-Co-Glycolic Acid) Scaffolds for Skin Tissue Engineering. Biomaterials 2008, 29, 4100-4107.

28. McClendon, M. T.; Stupp, S. I. Tubular Hydrogels of Circumferentially Aligned Nanofibers to Encapsulate and Orient Vascular Cells. Biomaterials 2012, 33, 5713-5722.
29. Yamazoe, T.; Shiraki, N.; Toyoda, M.; Kiyokawa, N.; Okita, H.; Miyagawa, Y.; Akutsu, H.; Umezawa, A.; Sasaki, Y.; Kume, K.; et al. A Synthetic Nanofibrillar Matrix Promotes in Vitro Hepatic Differentiation of Embryonic Stem Cells and Induced Pluripotent Stem Cells. J. Cell Sci. 2013, 126, 5391-5399.
30. Thibault, R. A.; Scott Baggett, L.; Mikos, A. G.; Kasper, F. K. Osteogenic Differentiation of Mesenchymal Stem Cells on Pregenerated Extracellular Matrix Scaffolds in the Absence of Osteogenic Cell Culture Supplements. Tissue Eng., Part A 2010, 16, 431-440.
31. Gershovich, J. G.; Dahlin, R. L.; Kasper, F. K.; Mikos, A. G. Enhanced Osteogenesis in Cocultures with Human Mesenchymal Stem Cells and Endothelial Cells on Polymeric Microfiber Scaffolds. Tissue Eng. Part A 2013, 19, 2565-2576.
32. Cohen-Karni, T.; Jeong, K. J.; Tsui, J. H.; Reznor, G.; Mustata, M.; Wanunu, M.; Graham, A.; Marks, C.; Bell, D. C.; Langer, R.; et al. Nanocomposite Gold-Silk Nanofibers. Nano Lett. 2012, 12, 5403-5406.
33. Das, A.; Segar, C. E.; Hughley, B. B.; Bowers, D. T.; Botchwey, E. A. The Promotion of Mandibular Defect Healing by the Targeting of S1P Receptors and the Recruitment of Alternatively Activated Macrophages. Biomaterials 2013, 34, 9853-9862.
34. Nur-E-Kamal, A.; Ahmed, I.; Kamal, J.; Schindler, M.; Meiners, S. Three-Dimensional Nanofibrillar Surfaces Promote Self-Renewal in Mouse Embryonic Stem Cells. Stem Cells 2006, 24, 426-433.
35. Hashemi, S. M.; Soudi, S.; Shabani, I.; Naderi, M.; Soleimani, M. The Promotion of Stemness and Pluripotency Following Feeder-Free Culture of Embryonic Stem Cells on Collagen-Grafted 3-Dimensional Nanofibrous Scaffold. Biomaterials 2011, 32, 7363-7374.
36. Kingham, E.; Oreffo, R. O. C. Embryonic and Induced Pluripotent Stem Cells: Understanding, Creating, and Exploiting the Nano-Niche for Regenerative Medicine. ACS Nano 2013, 7, 1867-1881.
37. Ardeshirylajimi, A.; Hosseinkhani, S.; Parivar, K.; Yaghmaie, P.; Soleimani, M. Nanofiber-Based Polyethersulfone Scaffold and Efficient Differentiation of Human Induced Pluripotent Stem Cells into Osteoblastic Lineage. Mol. Biol. Rep. 2013, 40, 4287-4294.
38. Liu, W.; Thomopoulos, S.; Xia, Y. Electrospun Nanofibers for Regenerative Medicine. Adv. Healthcare Mater. 2012, 1, 10-25.
39. Murray, R. A.; Zhang, G.; Harmata, D.; Neal, R. A.; Botchwey, E. A.; Fraser, C. L. Fabrication and Degradation of Nanofibers Based on Luminescent Boron Dye-PLGA Blends. In Biomaterials; American Chemical Society: Washington D.C., 2010; pp. 33-42.
40. Miller, R. A.; Brady, J. M.; Cutright, D. E. Degradation Rates of Oral Resorbable Implants (Polylactates and Polyglycolates): Rate Modification with Changes in PLA/PGA Copolymer Ratios. J. Biomed. Mater. Res. 1977, 11, 711-719.
41. Sun, H.; Scharff-Poulsen, A. M.; Gu, H.; Almdal, K. Synthesis and Characterization of Ratiometric, pH Sensing Nanoparticles with Covalently Attached Fluorescent Dyes. Chem. Mater. 2006, 18, 3381-3384.
42. Zhang, G.; Palmer, G. M.; Dewhirst, M. W.; Fraser, C. L. A Dual-Emissive-Materials Design Concept Enables Tumour Hypoxia Imaging. Nat. Mater. 2009, 8, 747-751.
43. Nam, J.; Johnson, J.; Lannutti, J. J.; Agarwal, S. Modulation of Embryonic Mesenchymal Progenitor Cell Differentiation via Control Over Pure Mechanical Modulus in Electrospun Nanofibers. Acta Biomater. 2011, 7, 1516-1524.
44. Kai, D.; Prabhakaran, M. P.; Stahl, B.; Eblenkamp, M.; Wintermantel, E.; Ramakrishna, S. Mechanical Properties and in Vitro Behavior of Nanofiber-Hydrogel Composites for Tissue Engineering Applications. Nanotechnology 2012, 23, 095705.
45. Jiang, X.; Nai, M. H.; Lim, C. T.; Visage, C. Le; Chan, J. K. Y.; Chew, S. Y. Polysaccharide Nanofibers with Variable Compliance for Directing Cell Fate. J. Biomed. Mater. Res., Part A 2014.
46. Zhang, G.; Kooi, S. E.; Demas, J. N.; Fraser, C. L. Emission Color Tuning with Polymer Molecular Weight for Difluoroboron Dibenzoylmethane-Polylactide. Adv. Mater. (Weinheim, Ger.) 2008, 20, 2099-2104.
47. Forristal, C. E.; Christensen, D. R.; Chinnery, F. E.; Petruzzelli, R.; Parry, K. L.; Sanchez-Elsner, T.; Houghton, F. D. Environmental Oxygen Tension Regulates the Energy Metabolism and Self-Renewal of Human Embryonic Stem Cells. PLoS One 2013, 8, e62507.
48. Grayson, W. L.; Zhao, F.; Izadpanah, R.; Bunnell, B.; Ma, T. Effects of Hypoxia on Human Mesenchymal Stem Cell Expansion and Plasticity in 3D Constructs. J. Cell. Physiol. 2006, 207, 331-339.
49. Bath, C.; Yang, S.; Muttuvelu, D.; Fink, T.; Emmersen, J.; Vorum, H.; Hjortdal, J.; Zachar, V. Hypoxia Is a Key Regulator of Limbal Epithelial Stem Cell Growth and Differentiation. Stem Cell Res. 2013, 10, 349-360.
50. Stacpoole, S. R. L.; Webber, D. J.; Bilican, B.; Compston, A.; Chandran, S.; Franklin, R. J. M. Neural Precursor Cells Cultured at Physiologically Relevant Oxygen Tensions Have a Survival Advantage Following Transplantation. Stem Cells Transl. Med. 2013, 2, 464-472.
51. McKeown, S. R. Defining Normoxia, Physoxia and Hypoxia in Tumours-Implications for Treatment Response. Br. J. Radiol. 2014, 87, 20130676.
52. Carreau, A.; Hafny-Rahbi, B. El; Matejuk, A.; Grillon, C.; Kieda, C. Why Is the Partial Oxygen Pressure of Human Tissues a Crucial Parameter? Small Molecules and Hypoxia. J. Cell. Mol. Med. 2011, 15, 1239-1253.
53. Buchwald, P.; Theor. Biol. Med. Model. 2009, 6, 5.
54. Ludwig, B.; Rotem, A.; Schmid, J.; Weir, G. C.; Colton, C. K.; Brendel, M. D.; Neufeld, T.; Block, N. L.; Yavriyants, K.; Steffen, A.; et al. Improvement of Islet Function in a Bioartificial Pancreas by Enhanced Oxygen Supply and Growth Hormone Releasing Hormone Agonist. Proc. Natl. Acad. Sci. U.S.A 2012, 109, 5022-5027.
55. Pedraza, E.; Coronel, M. M.; Fraker, C. A.; Ricordi, C.; Stabler, C. L. Preventing Hypoxia-Induced Cell Death in Beta Cells and Islets via Hydrolytically Activated, Oxygen-Generating Biomaterials. Proc. Natl. Acad. Sci. U.S.A 2012, 109, 4245-4250.
56. Wilson, J. T.; Cui, W.; Chaikof, E. L. Layer-by-Layer Assembly of a Conformal Nanothin PEG Coating for Intraportal Islet Transplantation. Nano Lett. 2008, 8, 1940-1948.
57. Duling, B. R.; Berne, R. M. Longitudinal Gradients in Periarteriolar Oxygen Tension. A Possible Mechanism for the Participation of Oxygen in Local Regulation of Blood Flow. Circ. Res. 1970, 27, 669-678.
58. Allen, J.; Liu, Y.; Kim, Y. L.; Turzhitsky, V. M.; Backman, V.; Ameer, G. A. Spectroscopic Translation of Cell-Material Interactions. Biomaterials 2007, 28, 162-174.
59. U.S. Pat. No. 7,955,861 (Fraser et al.)

60. U.S. patent application Ser. No. 13/512,052 (Fraser et al.)
61. U.S. Pat. No. 8,728,817 (Ogle et al.).

The invention claimed is:

1. A dual layered scaffold for measuring oxygen levels in tissues or cells, said dual layered scaffold comprising an electrospun boron dye-polymer conjugate nanofiber layer and an electrospun structural support nanofiber layer, wherein said polymer is poly(lactic acid) (PLA), wherein difluoroboron dibenzoylmethane ($BF_2$dbmOH) or iodide substituted difluoroboron dibenzoylmethane ($BF_2$dbm(I)OH) are used to prepare said boron dye-polymer conjugate, wherein said electrospun structural support layer comprises poly(3-hydroxybutyrate-co-3-hydroxyvalerate) (PHBV) and polycaprolactone (PCL), wherein the boron dye emits a phosphorescence signal and a fluorescence signal and the ratio of the signals is dependent on the oxygen levels present.

2. The dual layered scaffold of claim 1, wherein electrospinning process parameters for said dye-polymer conjugate nanofiber layer are 30% (weight/volume) dye-polymer in 10% (volume/volume) pyridinium formate, 20% (volume/volume) ethanol, in dichloromethane at a 25 kV applied voltage, 14.5 cm working distance, and a solution flow rate of 1 mL/hr, further wherein said dye-polymer conjugate nanofibers are electrospun onto said structural support nanofiber layer, further wherein said structural support nanofiber layer is dry when said dye-polymer conjugate nanofibers are electrospun onto it.

3. The dual layered scaffold of claim 1, wherein said boron dye-polymer conjugate nanofiber layer is electrospun onto said electrospun structural support nanofiber layer.

4. The dual layered scaffold of claim 1, wherein said boron dye is dual emissive for fluorescence and phosphorescence.

5. The dual layered scaffold of claim 1, wherein said boron dye emits a phosphorescence signal and a fluorescence signal, further wherein the ratio of said signals changes when oxygen levels change.

6. The dual layered scaffold of claim 5, wherein the phosphorescence signal is oxygen sensitive and the fluorescence signal is oxygen insensitive.

7. A method of determining oxygen levels using a dual layer scaffold of claim 1, said method comprising contacting a cell, a tissue, or a tissue sample with said scaffold, measuring the emitted fluorescence and phosphorescence spectra and determining the oxygen levels.

8. The method of claim 7, wherein said contacting comprises attaching said cell or said tissue to said scaffold.

9. The method of claim 8, wherein said scaffold is implanted into a subject before said oxygen levels are determined.

10. The method of claim 9, wherein said tissue is selected from the group consisting of ischemic tissue, transplanted tissue, diseased tissue, and injured tissue.

11. The method of claim 10, wherein said transplanted tissue is pancreatic islet tissue.

12. The method of claim 11, wherein said oxygen levels are measured in said islet tissue.

13. The method of claim 7, wherein the method detects hypoxia.

14. The dual layered scaffold of claim 1, wherein said tissue is selected from the group consisting of pancreatic tissue, ischemic tissue, transplanted tissue, diseased tissue, and injured tissue.

15. The dual layered scaffold of claim 14, wherein said ischemic tissue is ischemic pancreatic islet tissue.

* * * * *